(12) United States Patent
Numata et al.

(10) Patent No.: US 8,895,966 B2
(45) Date of Patent: Nov. 25, 2014

(54) MATERIAL FOR ORGANIC ELECTROLUMINESCENCE ELEMENT, AND ORGANIC ELECTROLUMINESCENCE ELEMENT USING SAME

(75) Inventors: Masaki Numata, Chiba (JP); Hideaki Nagashima, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 240 days.

(21) Appl. No.: 13/638,317

(22) PCT Filed: Feb. 14, 2011

(86) PCT No.: PCT/JP2011/053056
§ 371 (c)(1),
(2), (4) Date: Dec. 3, 2012

(87) PCT Pub. No.: WO2011/122133
PCT Pub. Date: Oct. 6, 2011

(65) Prior Publication Data
US 2013/0092905 A1    Apr. 18, 2013

(30) Foreign Application Priority Data
Mar. 31, 2010 (JP) ................................. 2010-084477

(51) Int. Cl.
*H01L 35/24* (2006.01)

(52) U.S. Cl.
USPC .................................... 257/40; 257/E51.001

(58) Field of Classification Search
USPC ........................................... 257/40, E51.001
See application file for complete search history.

(56) References Cited

FOREIGN PATENT DOCUMENTS

| | | |
|---|---|---|
| JP | 2004 253298 | 9/2004 |
| WO | 2007 008459 | 1/2007 |
| WO | 2007 077810 | 7/2007 |
| WO | 2007 119816 | 10/2007 |
| WO | 2009 060757 | 5/2009 |
| WO | 2009 060779 | 5/2009 |
| WO | 2009 085344 | 7/2009 |

OTHER PUBLICATIONS

U.S. Appl. No. 13/637,988, filed Sep. 28, 2012, Numata, et al.
O'Brien, D. F., et al., "Improved energy transffer in electrophosphorescent devices," Applied Physics Letters, vol. 74, No. 3, pp. 442 to 444, (Jan. 18, 1999).
Baldo, M. A., et al., "Very high-efficiency green organic light-emitting devices based on electrophosphorescence," Applied Physics Letters, pp. 4 to 6, vol. 75, No. 1, (Jul. 5, 1999).
International Search Report Issued Apr. 26, 2011 in PCT/JP11/053056 Filed Feb. 14, 2011.

*Primary Examiner* — Anthony Ho
(74) *Attorney, Agent, or Firm* — Oblon, Spivak, McClelland, Maier & Neustadt, L.L.P.

(57) ABSTRACT

Provided is a material for an organic electroluminescence device, which further has a bulky carbazolyl group at each of the 3-position and 6-position of its central carbazole skeleton, and which has a dibenzofuran skeleton or a dibenzothiophene skeleton at the N atom of the central carbazole skeleton through a linking group as required. Also provided is an organic electroluminescence device, including one or more organic thin film layers including a light emitting layer between a cathode and an anode, in which at least one layer of the organic thin film layers contains the material for an organic electroluminescence device.

19 Claims, No Drawings

MATERIAL FOR ORGANIC ELECTROLUMINESCENCE ELEMENT, AND ORGANIC ELECTROLUMINESCENCE ELEMENT USING SAME

TECHNICAL FIELD

The present invention relates to a material for an organic electroluminescence device and an organic electroluminescence device using the material.

BACKGROUND ART

An organic electroluminescence device (hereinafter, "electroluminescence" may be abbreviated as "EL") is a spontaneous light emitting device which utilizes the principle that a fluorescent substance or a phosphorescent substance emits light by energy of recombination of holes injected from an anode and electrons injected from a cathode when an electric field is applied. Since an organic EL device of the laminate type driven under a low electric voltage was reported, many studies have been conducted on organic EL devices using organic materials as the constituent materials. The devices of the laminate type use tris(8-quinolinolato)aluminum for a light emitting layer and a tetraphenyldiamine derivative for a hole transporting layer. Advantages of the laminate structure are, for example, that the efficiency of hole injection into the light emitting layer can be increased, that the efficiency of forming excitons which are formed in the light emitting layer by blocking and recombining electrons injected from the cathode can be increased, and that excitons formed in the light emitting layer can be confined. As described above, for the structure of the organic EL device, a two-layered structure having a hole transporting (injecting) layer and an electron transporting light emitting layer and a three-layered structure having a hole transporting (injecting) layer, a light emitting layer, and an electron transporting (injecting) layer are well known. To increase the efficiency of recombination of injected holes and electrons in the devices of the laminate type, the structure of the device and the process for forming the device have been studied.

As a light emitting material for an organic EL device, there are known light emitting materials including a chelate complex such as a tris(8-quinolinolato)aluminum complex, a coumarin derivative, a tetraphenylbutadiene derivative, a distyrylarylene derivative, and an oxadiazole derivative. It is reported that light emission ranging from blue light to red light in a visible light region can be obtained by using those light emitting materials, and a device exhibiting color images was realized.

A fluorescent light emitting material that emits light by means of a singlet exciton has been conventionally used as a light emitting material for an organic EL device. In recent years, the utilization of a phosphorescent light emitting material that emits light by means of a triplet exciton as well as the fluorescent light emitting material has also been proposed (for example, Non Patent Literatures 1 and 2). An organic EL device using the phosphorescent light emitting material can achieve luminous efficiency three to four times as high as that of an organic EL device using only the fluorescent light emitting material because it is assumed that singlet excitons and triplet excitons are produced at a ratio of 1:3 upon recombination of electrons and holes in an organic EL device by virtue of a difference in spin multiplicity. In blue phosphorescent light emission, however, high efficiency and a long lifetime are hard to achieve, and hence the development of a host material that achieves the high efficiency and the long lifetime has been desired.

Although Patent Literatures 1 and 2 each describe a compound having a carbazole skeleton substituted with carbazole at each of its 3- and 6-positions through an N atom (3,6-dicarbazolylcarbazole skeleton), none of the documents describes a compound in which the dicarbazolylcarbazole skeleton is bonded to dibenzofuran or dibenzothiophene on its N atom through a single bond or a linking group. Patent Literature 3 does not describe the dicarbazolylcarbazole skeleton. In addition, a light emitting device using any one of the compounds described in Patent Literatures 1 to 3 has been insufficient in efficiency and lifetime of blue phosphorescent light emission.

CITATION LIST

Patent Literature

[PTL 1] WO 2007/108459 A1
[PTL 2] WO 2007/119816 A1
[PTL 3] WO 2007/077810 A1

Non Patent Literature

[NPL 1] Applied Physics letters Vol. 74 No. 3, pp 442-444
[NPL 2] Applied Physics letters Vol. 75 No. 1, pp-4-6

SUMMARY OF INVENTION

Technical Problem

The present invention has been made to solve the problems, and an object of the present invention is to provide an organic EL device that emits phosphorescence with high efficiency and a long lifetime, and a material for an organic EL device for realizing the device.

Solution to Problem

The inventors of the present invention have made extensive studies to achieve the object, and as a result, have found that the object is achieved with the following material for an organic electroluminescence device. The material further has a bulky carbazolyl group at each of the 3-position and 6-position of its central carbazole skeleton, and has a dibenzofuran skeleton or a dibenzothiophene skeleton at the N atom of the central carbazole skeleton through a linking group as required. Thus, the inventors have reached the present invention.

That is, the present invention provides a material for an organic electroluminescence device, which is represented by the following formula (1):

[Chem.1]

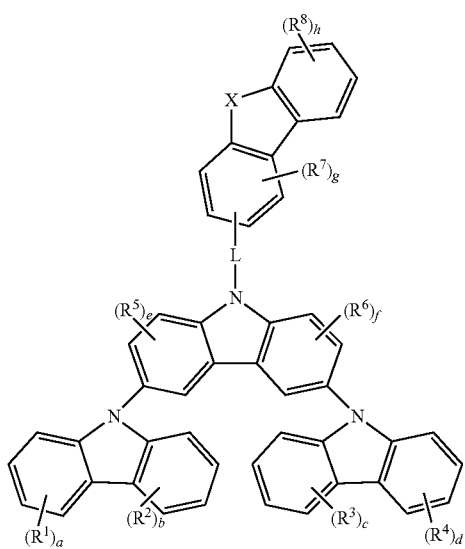

(1)

in the formula (1):
X represents an oxygen atom or a sulfur atom, $R^1$ to $R^8$ each independently represent an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group, or a cyano group, the substituents $R^1$ to $R^8$ may each be further substituted with any one of the substituents, and when a plurality of any one of $R^1$'s to $R^8$'s exist, the plurality of substituents may be identical to or different from each other;
a to d and h each independently represent an integer of any one of 0 to 4, e to g each independently represent an integer of any one of 0 to 3, and a total of a to h is 6 or less; and
L represents a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms, and may be substituted with any one of the substituents $R^1$ to $R^8$.

The present invention also provides an organic electroluminescence device, including one or more organic thin film layers including a light emitting layer between a cathode and an anode, in which at least one layer of the organic thin film layers contains the material for an organic electroluminescence device represented by the formula (1).

Advantageous Effects of Invention

According to the present invention, it is possible to provide the organic EL device that emits phosphorescence with high efficiency and a long lifetime, and the material for an organic EL device for realizing the device.

DESCRIPTION OF EMBODIMENTS

A material for an organic electroluminescence device of the present invention is represented by the following formula (1):

[Chem. 2]

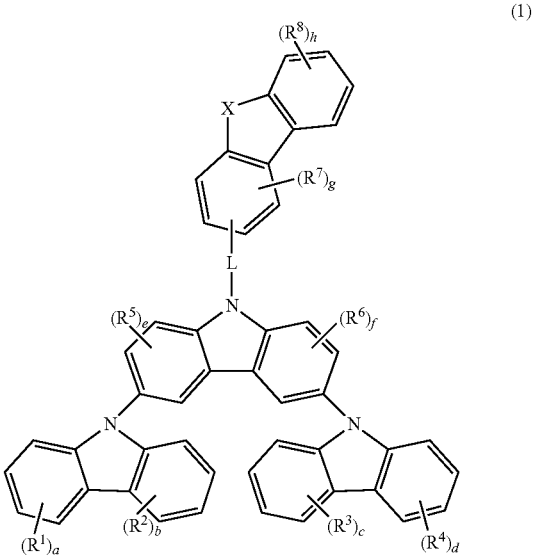

(1)

in the formula (1):
X represents an oxygen atom or a sulfur atom, $R^1$ to $R^8$ each independently represent an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group, or a cyano group, the substituents $R^1$ to $R^8$ may each be further substituted with any one of the substituents (hereinafter, sometimes collectively referred to as "substituent R"), and when a plurality of any one of $R^1$'s to $R^8$'s exist, the plurality of substituents may be identical to or different from each other;
a to d and h each independently represent an integer of any one of 0 to 4, e to g each independently represent an integer of any one of 0 to 3, and a total of a to h is 6 or less; and
L represents a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms, and may be substituted with any one of the substituents R's.

When the structure in which groups on both sides out of the three carbazolyl groups are bonded to the 3- and 6-positions of the central carbazolyl group through their N atoms as represented by the formula (1) is adopted, the following characteristics are achieved: (1) the material can have a high triplet energy level; (2) as the substituent at each of the 3- and 6-positions of the carbazole group is sterically bulky carbazole, the aggregation of its molecules upon formation of the material into a thin film is suppressed and hence a uniform thin film is formed; and (3) further, when the material for an organic EL device of the present invention is used as a host, the aggregated phase can serve as a deactivation site for light emission energy and hence a thin film in which the aggregation has been suppressed is advantageous for the production of a high-efficiency device.

In addition, the characteristics are additionally improved by the fact that the three carbazolyl groups and the one dibenzofuranyl group or the one dibenzothiophenyl group are used as essential constituents, and in particular, a dicarbazolylcarbazole group is used and the dibenzofuranyl group or the dibenzothiophenyl group is combined with the group on its N atom. On the other hand, the introduction of any more dibenzofuranyl group or dibenzothiophenyl group, or the introduction of a high-molecular weight substituent results in too large a molecular weight for the synthesized compound to be stably sublimated, which may be disadvantageous in terms of the productivity of the material.

Examples of the alkyl group represented by each of $R^1$ to $R^8$ include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group.

Examples of the cycloalkyl group represented by each of $R^1$ to $R^8$ include a cyclopropyl group, a cyclobutyl group, a cyclopentyl group, a cyclohexyl group, a cycloheptyl group, a norbornyl group, and an adamantyl group.

Examples of the alkoxy group represented by each of $R^1$ to $R^8$ include a methoxy group, an ethoxy group, a propoxy group, a butoxy group, a pentyloxy group, and a hexyloxy group, and groups having three or more carbon atoms may be linear, cyclic, or branched.

Examples of the cycloalkoxy group represented by each of $R^1$ to $R^8$ include a cyclopentoxy group and a cyclohexyloxy group.

Examples of the aryl group represented by each of $R^1$ to $R^8$ include a phenyl group, a tolyl group, a xylyl group, a mesityl group, an o-biphenyl group, a m-biphenyl group, a p-biphenyl group, an o-terphenyl group, a m-terphenyl group, a p-terphenyl group, a naphthyl group, and a phenanthryl group. Of those, a phenyl group and a mesityl group are preferred.

Examples of the aryloxy group represented by each of $R^1$ to $R^8$ include a phenoxy group and a biphenyloxy group.

Examples of the heteroaryl group represented by each of $R^1$ to $R^8$ include a carbazolyl group, a dibenzofuranyl group, a dibenzothiophenyl group, a pyrrolyl group, a furyl group, a thienyl group, a silolyl group, a pyridyl group, a quinolyl group, an isoquinolyl group, a benzofuryl group, an imidazolyl group, a pyrimidyl group, a selenophenyl group, an oxadiazolyl group, a triazolyl group, an indolyl group, and a benzimidazolyl group.

$R^1$ to $R^8$ may each represent an amino group that may have a substituent, or a silyl group that may have a substituent. The substituent which the amino group that may have a substituent may have has the same meaning as that of each of the alkyl group, the cycloalkyl group, and the aryl group.

The substituent which the silyl group that may have a substituent may have has the same meaning as that of each of the alkyl group, the cycloalkyl group, and the aryl group.

a to d and h each independently represent preferably an integer of any one of 0 to 3, more preferably an integer of any one of 0 to 2. In addition, e to g each independently represent preferably an integer of any one of 0 to 2, more preferably an integer of 0 or 1. The total of a to h is preferably 4 or less from the viewpoint of sublimation stability. In addition, the molecular weight of the material for an organic electroluminescence device of the present invention is preferably 1,500 or less by the same reason.

Examples of the alkylene group, the cycloalkylene group having 3 to 20 ring carbon atoms, the arylene group having 6 to 18 ring carbon atoms, the heteroarylene group having 5 to 18 ring atoms, the divalent amino group, and the divalent silyl group each represented by L include groups each obtained by replacing one hydrogen atom of any one of the substituents $R^1$ to $R^8$ with a bonding hand. In the present invention, a 9,9-fluorenylidene group is also included in the arylene group.

A p-phenylene group, a m-phenylene group, or a biphenylene group as well as a group to be described later is suitable as the arylene group, and a biphenylamino group as well as a group to be described later is suitable as the amino group.

The linking group represented by L may further have a substituent, and the substituent has the same meaning as that of a substituent described for the substituents $R^1$ to $R^8$.

It should be noted that dibenzofuran has a larger triplet energy than that of dibenzothiophene and hence the triplet energy of the entire compound using dibenzofuran is expected to enlarge. In this case, the applications of the material for an organic EL device can be selected from a widened range, and hence X in the general formula (1) preferably represents an oxygen atom.

In addition, the general formula (1) is preferably represented by the following general formula (2).

[Chem. 3]

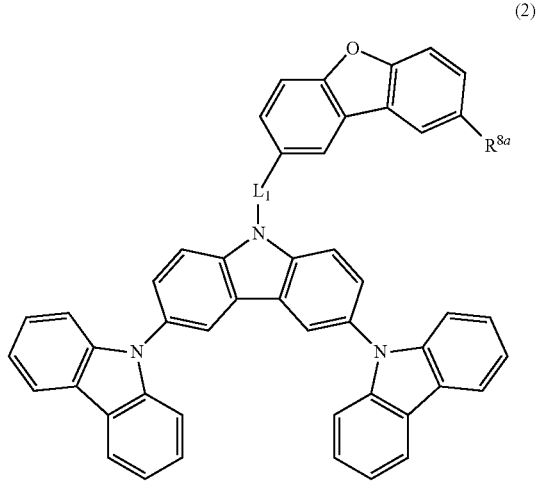

(2)

In the general formula (2), $L_1$ represents a single bond or an arylene group having 6 to 18 ring carbon atoms (preferably a phenylene group), and $R^{8a}$ represents a hydrogen atom, an aryl group having 6 to 18 ring carbon atoms (preferably a phenyl group), or a heteroaryl group having 5 to 18 ring atoms (preferably a carbazolyl group). It should be noted that the arylene group, the aryl group, and the heteroaryl group each have the same meaning as that in the description for the general formula (1).

The material for an organic EL device of the present invention is preferably a host material or a hole transporting material to be used together with a phosphorescent light emitting material. Further, the triplet energy level is preferably 2.0 eV or more, more preferably 2.5 eV or more.

Specific examples of the material for an organic EL device represented by the general formula (1) of the present invention are shown below. However, the present invention is not limited to these exemplified compounds. It should be noted that substituents shown in the following specific examples can be given as preferred substituents in the present invention.

[Chem. 4]

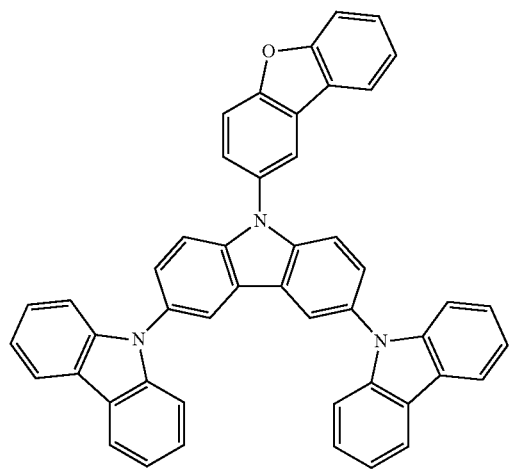

(1)

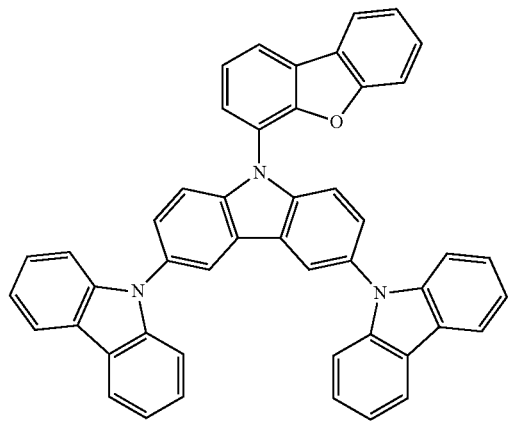

(3)

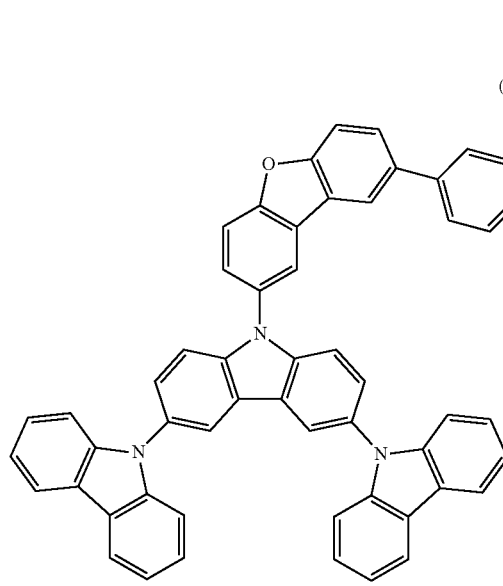

(2)

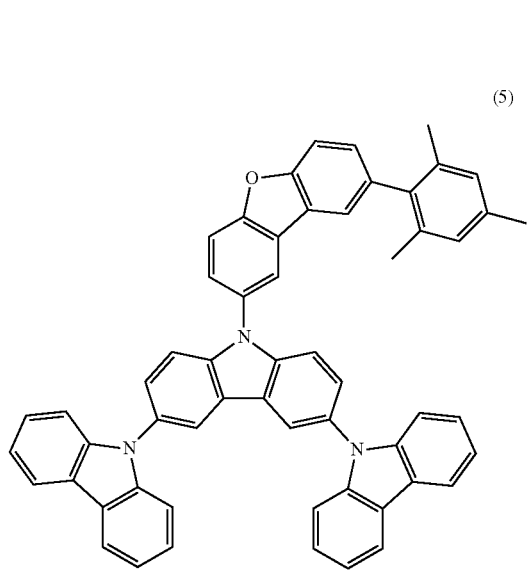

(4)

(5)

(6)
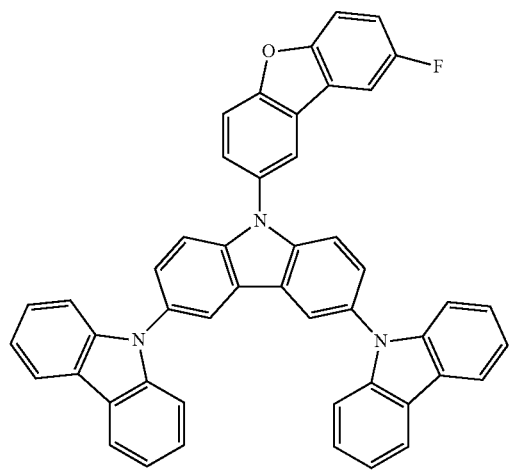
(9)
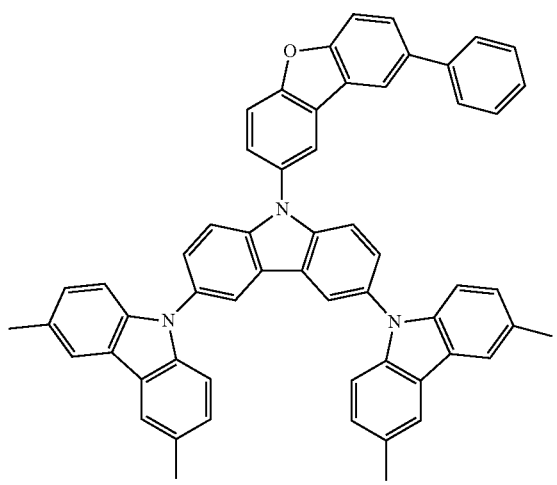
(7)
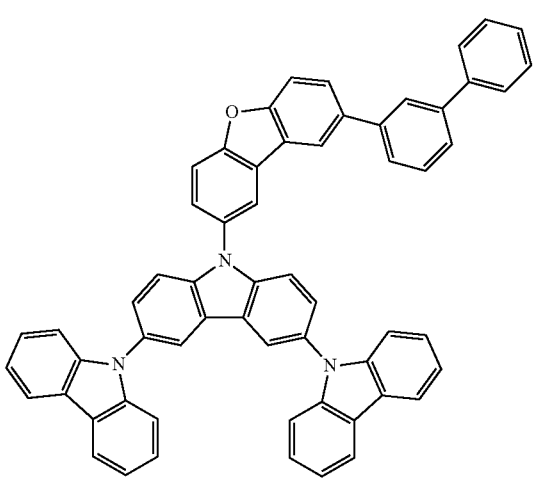
(10)
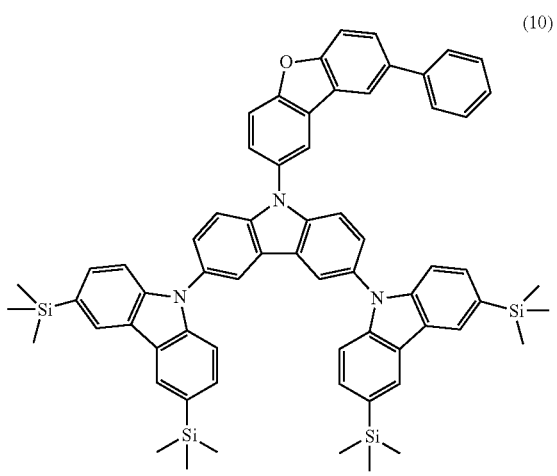
(8)
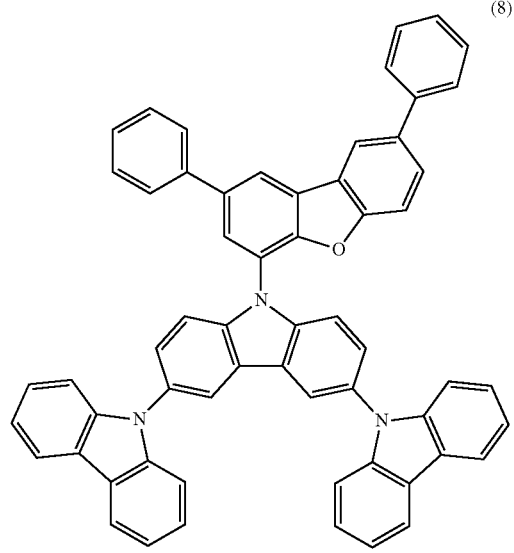
(11)
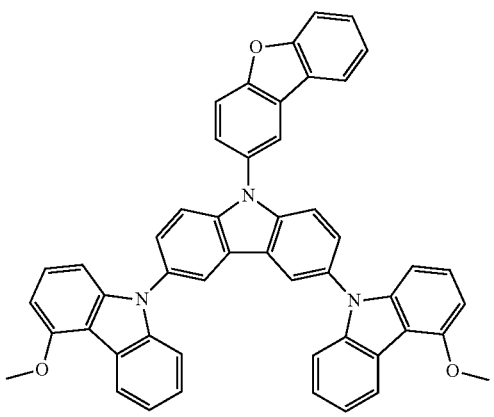

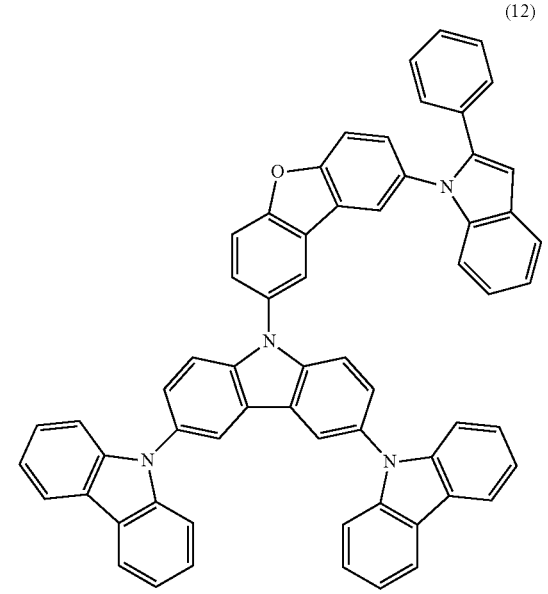
(12)
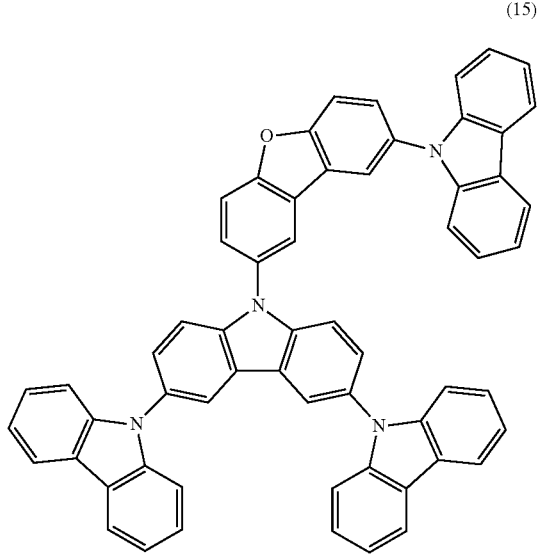
(15)
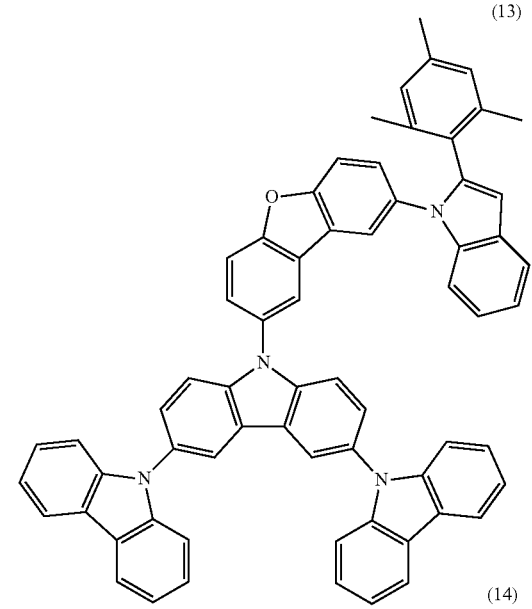
(13)
[Chem. 5]
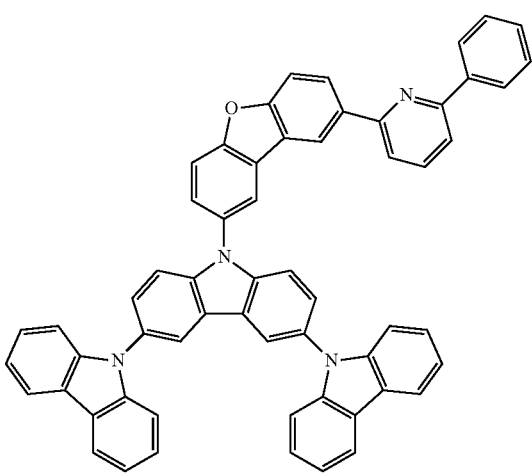
(16)
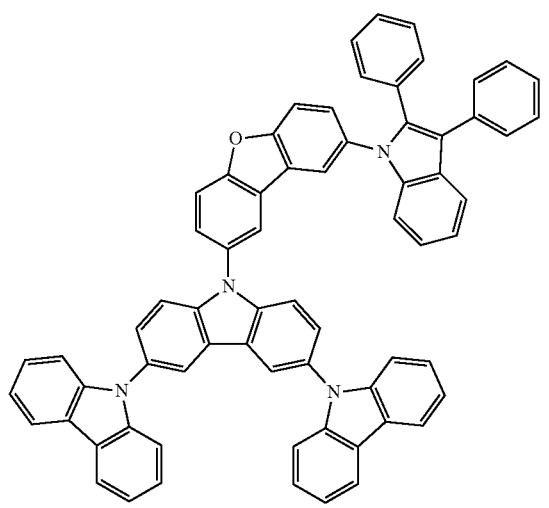
(14)
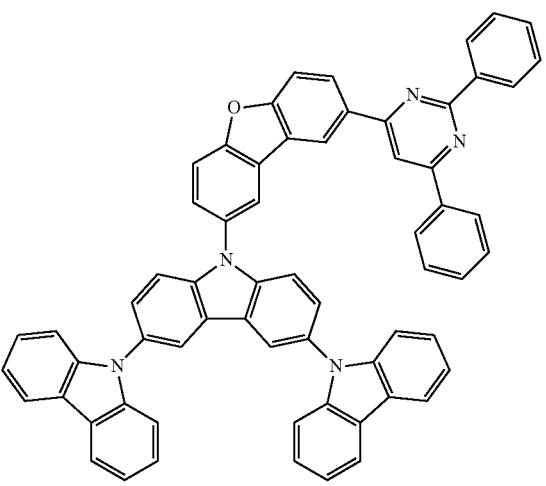
(17)

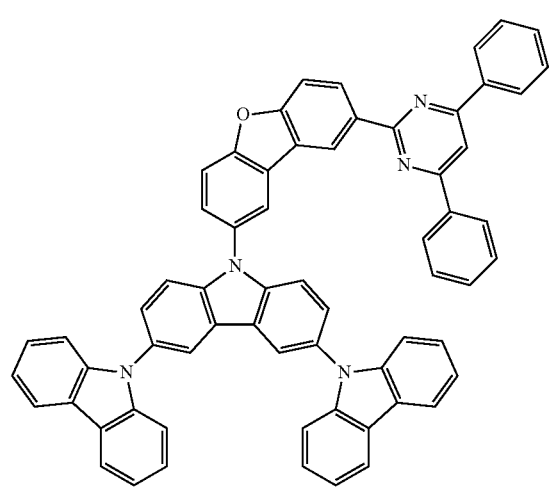
(18)
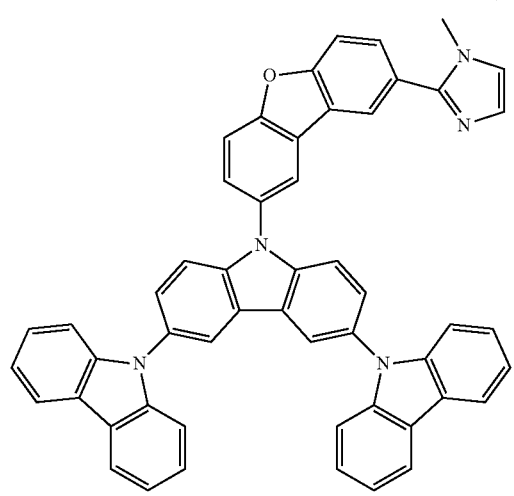
(19)
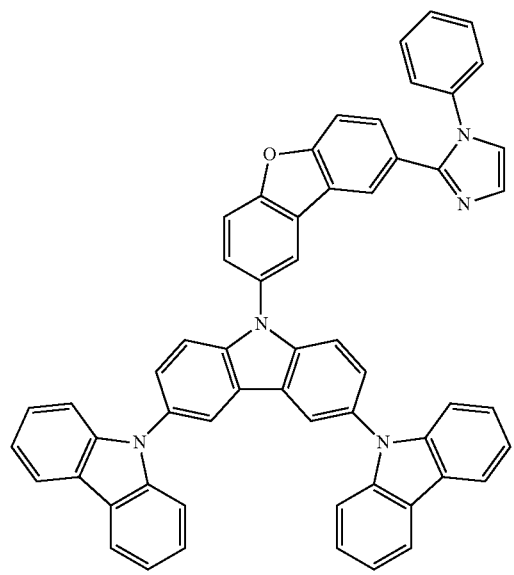
(20)
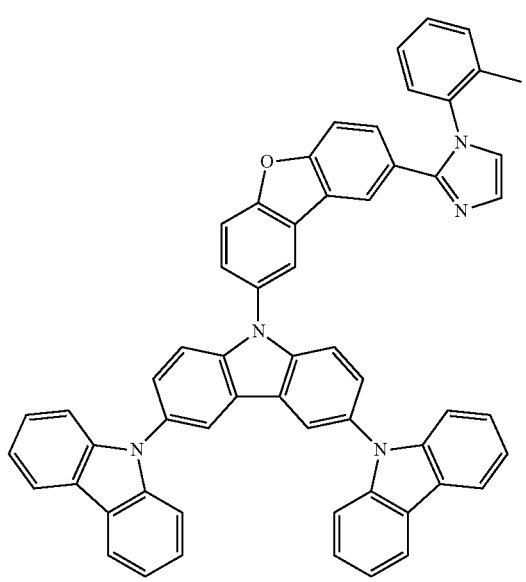
(21)
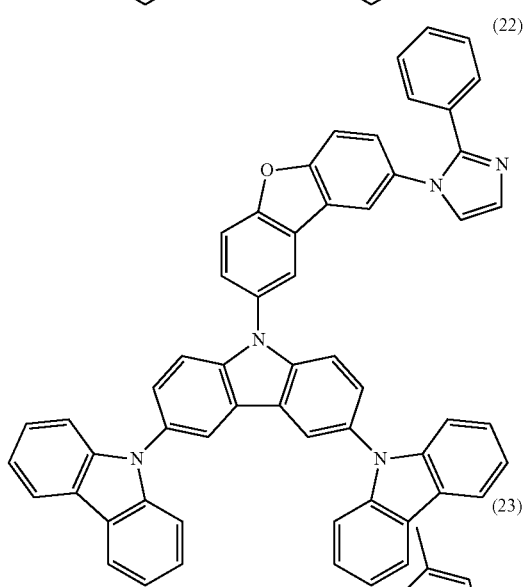
(22)
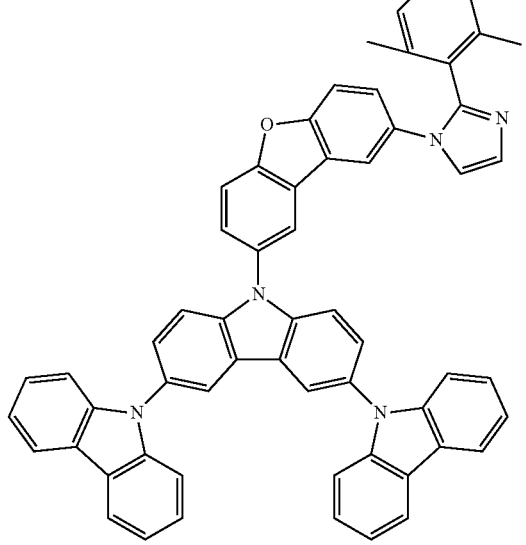
(23)

(24)
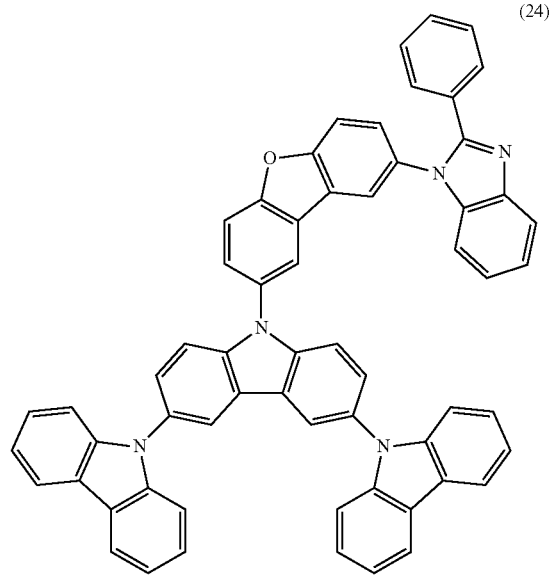
(25)
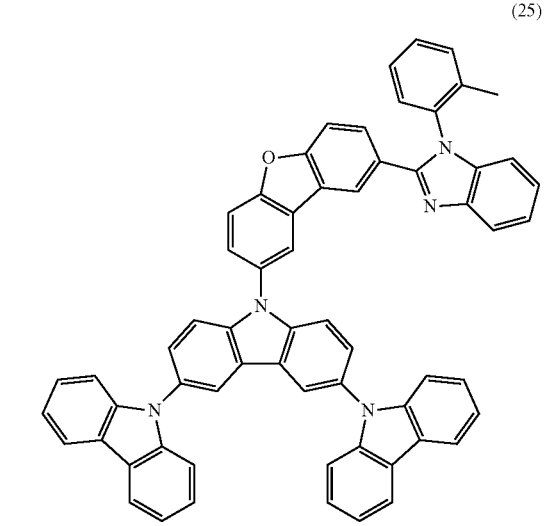
(26)
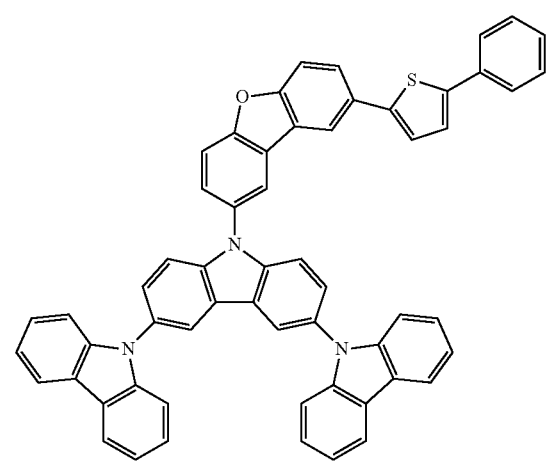
(27)
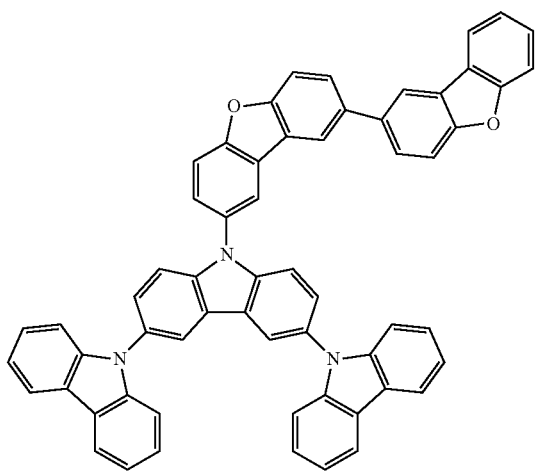
(28)
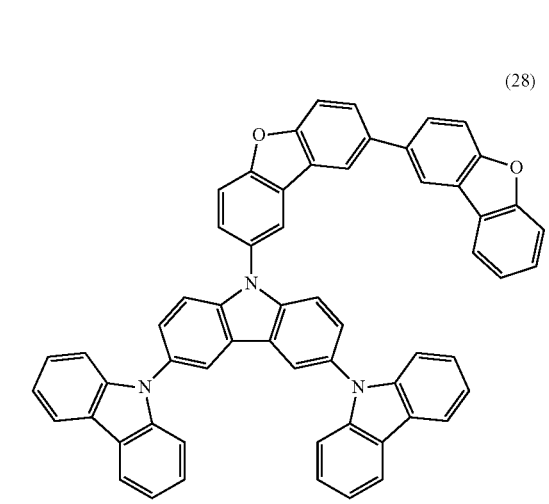
(29)
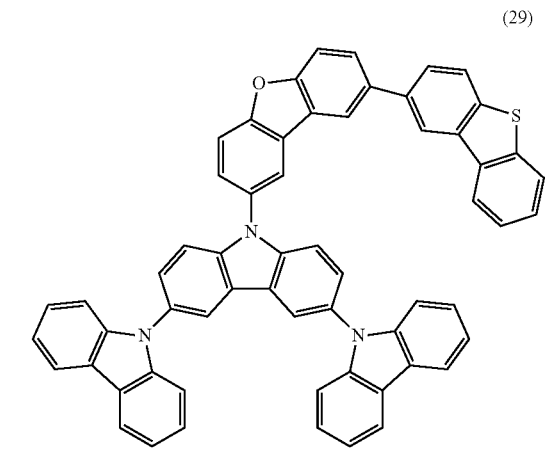

(30)
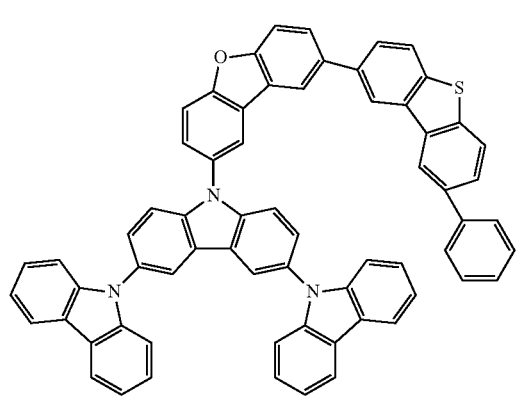
[Chem. 6]
(31)
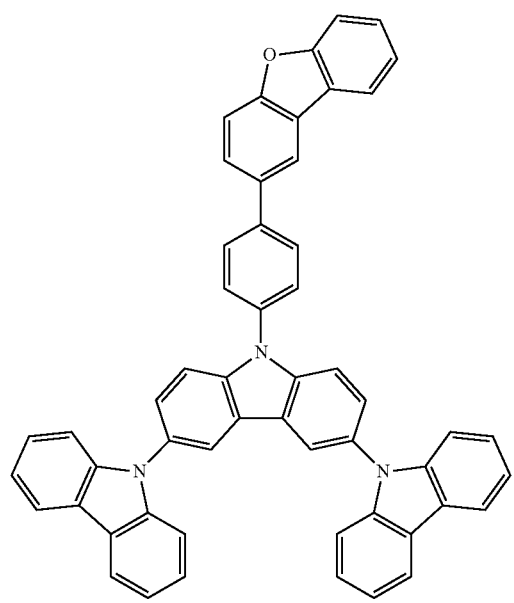
(32)
(33)
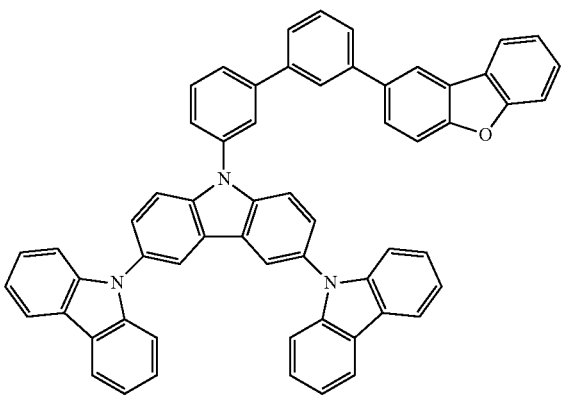
(34)
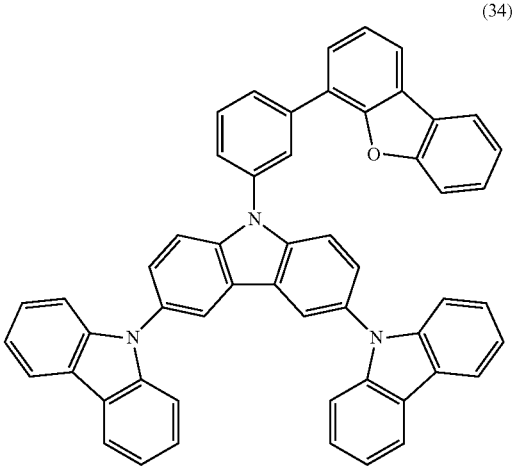
(35)
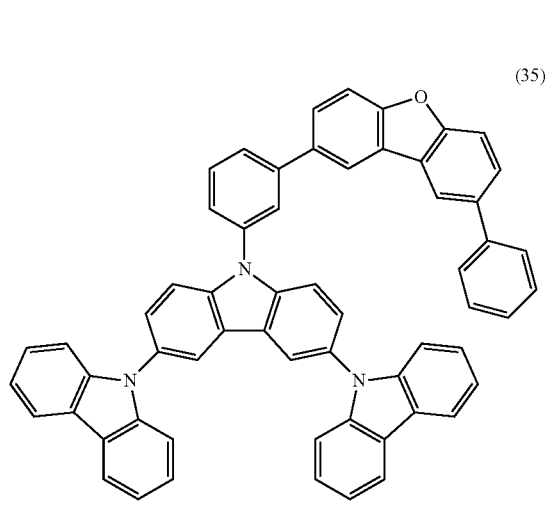

US 8,895,966 B2
19
-continued
(36)
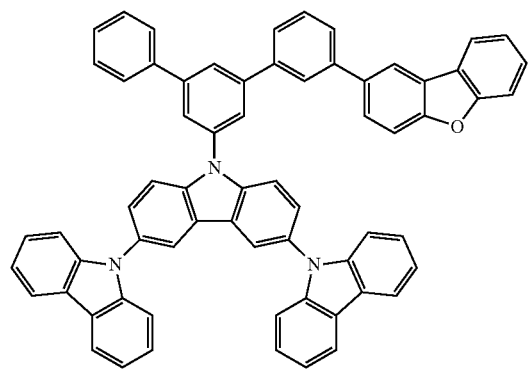
(37)
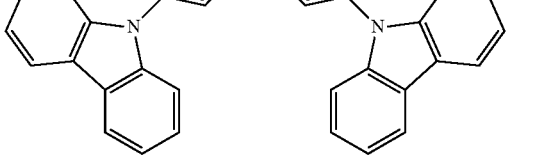
(38)
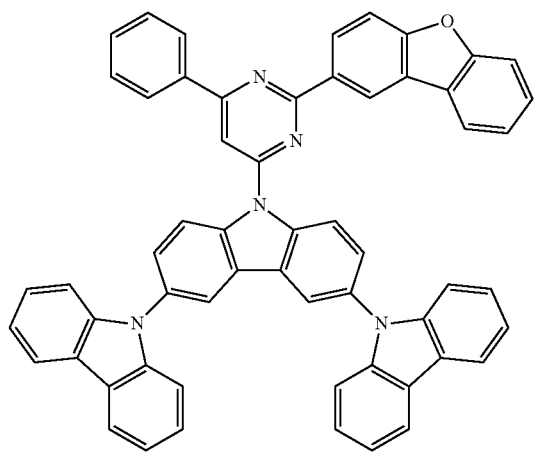
20
-continued
(39)
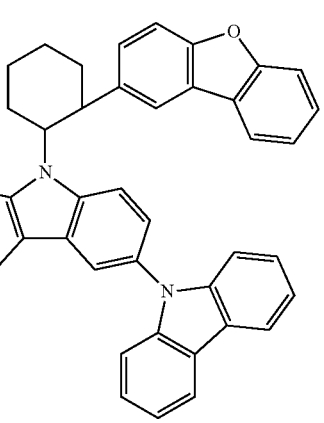
(40)
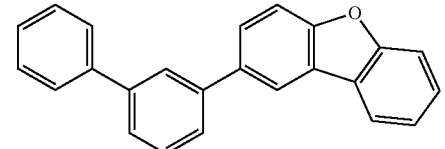
(41)

(42)
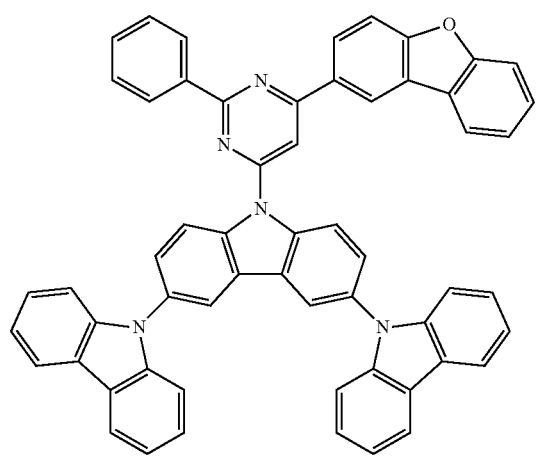
(43)
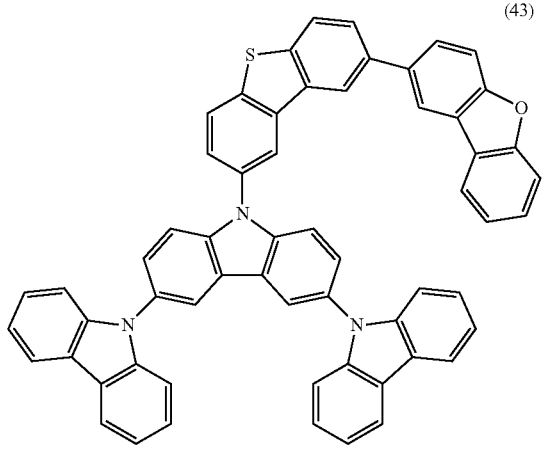
(44)
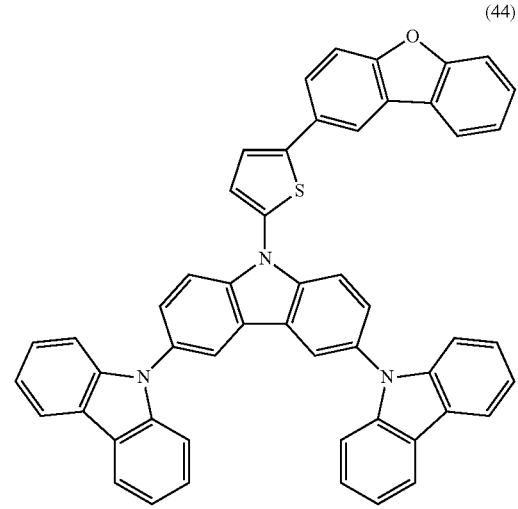
(45)
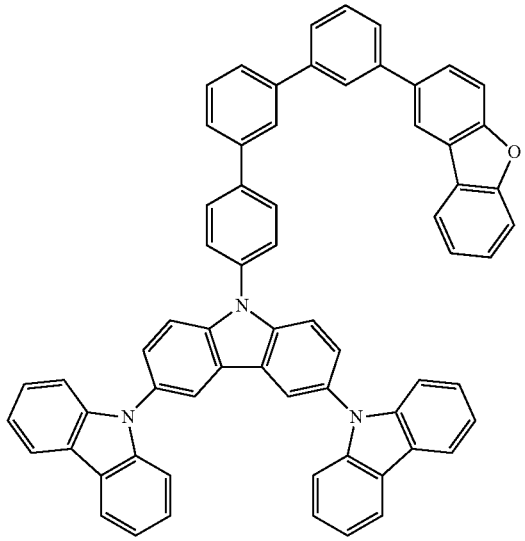
[Chem. 7]
(46)
(47)
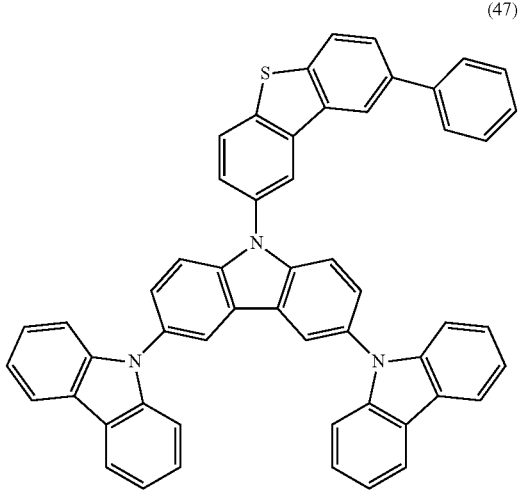

(48)
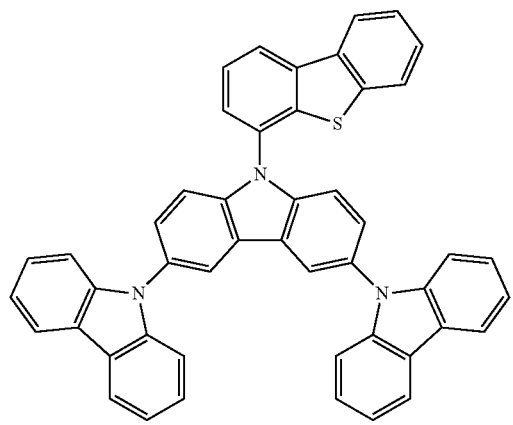
(49)
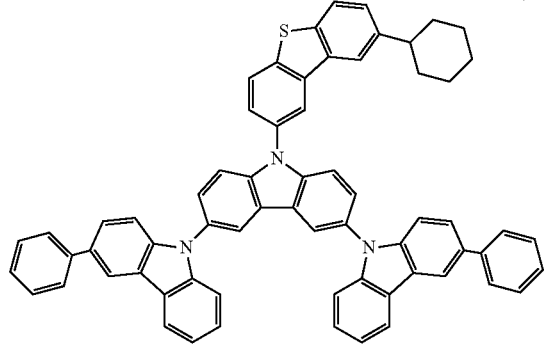
(50)
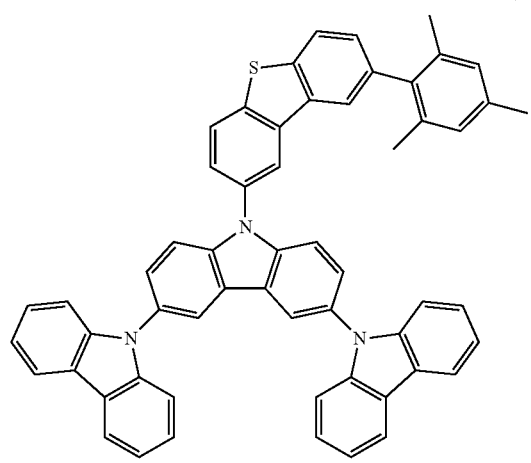
(51)
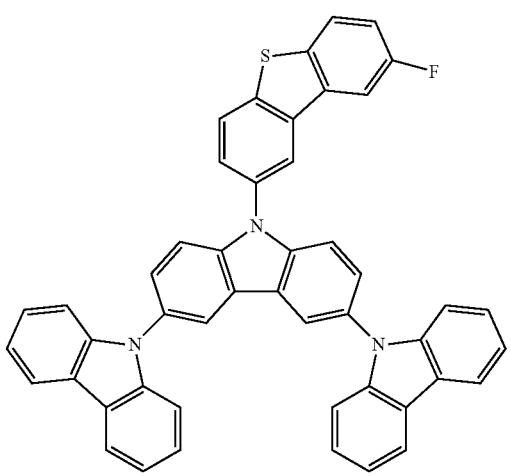
(52)
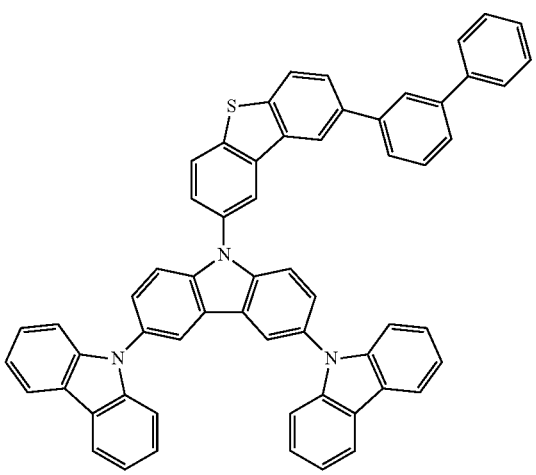
(53)
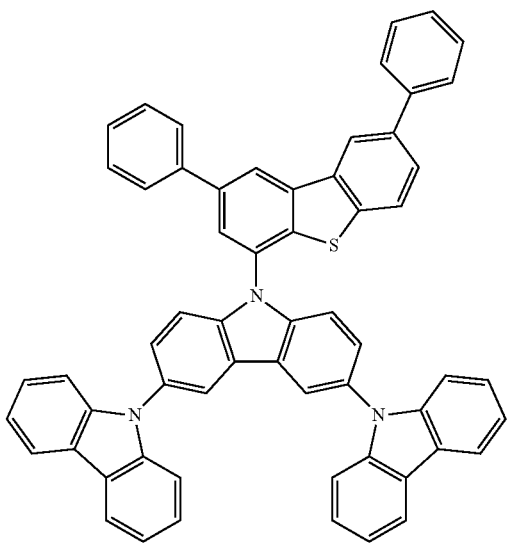

(54)
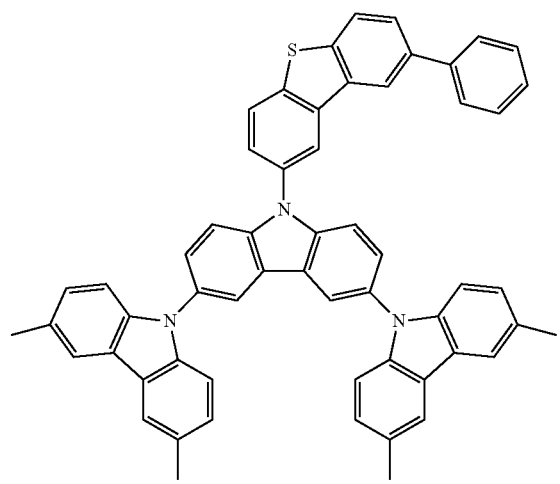
(55)
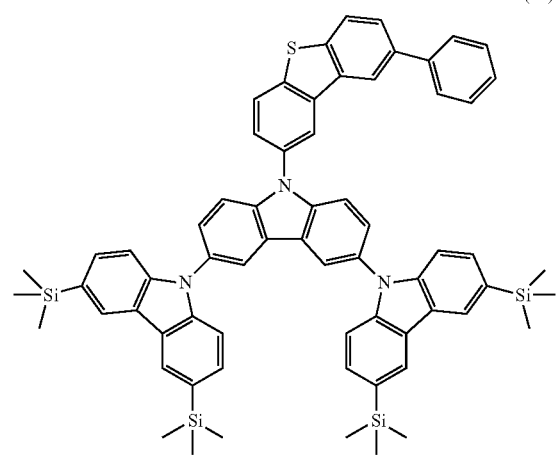
(56)
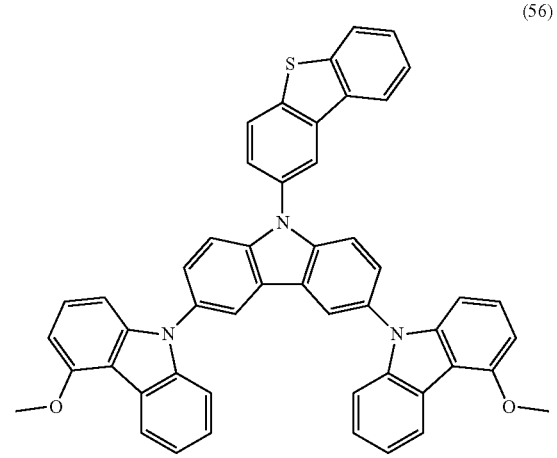
(57)
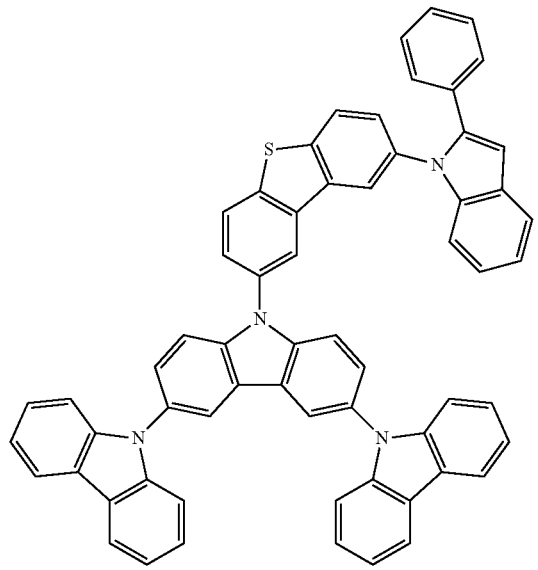
(58)
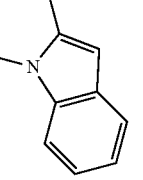
(59)
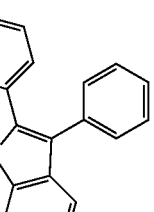

(60)
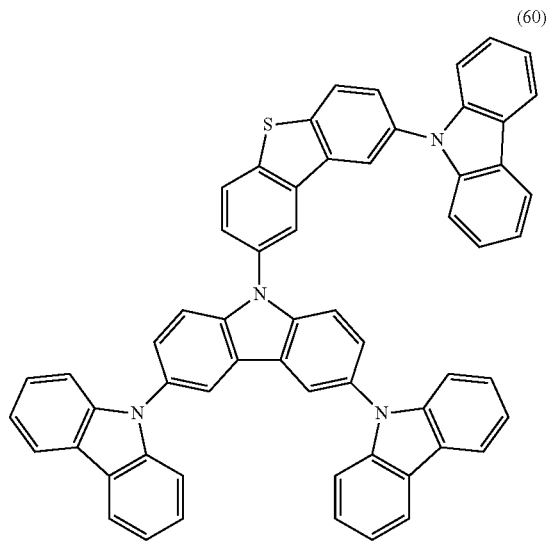
[Chem. 8]
(61)
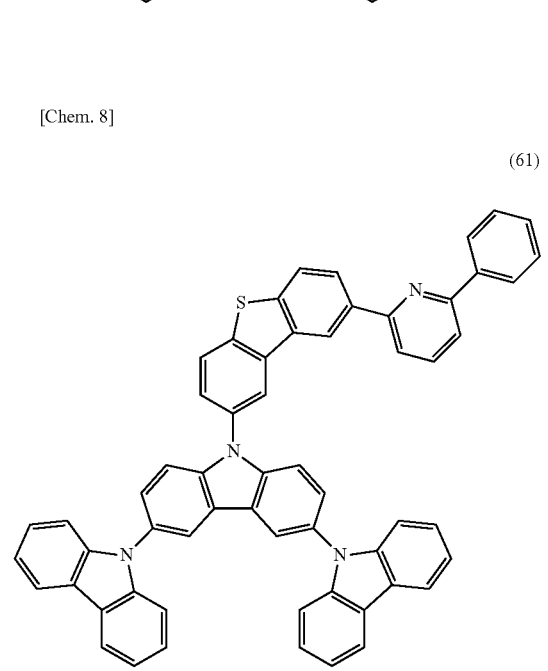
(62)
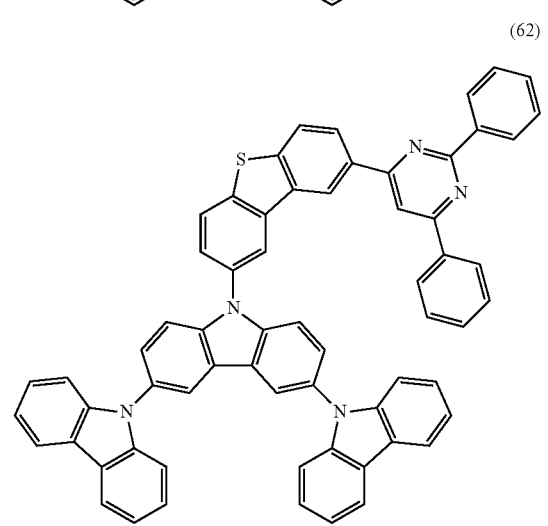
(63)
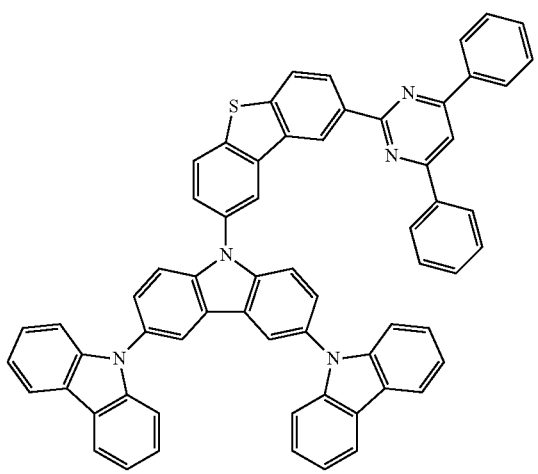
(64)
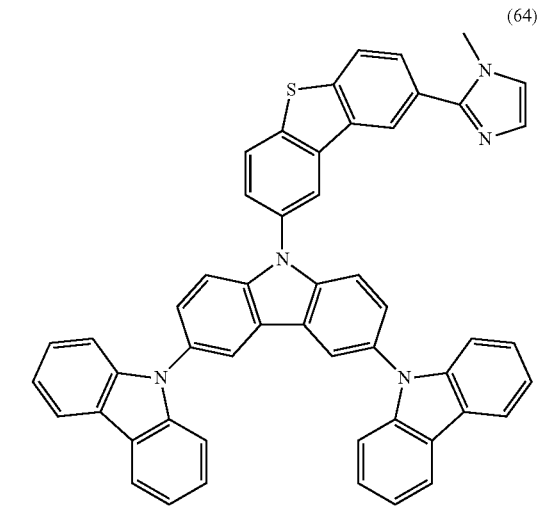
(65)
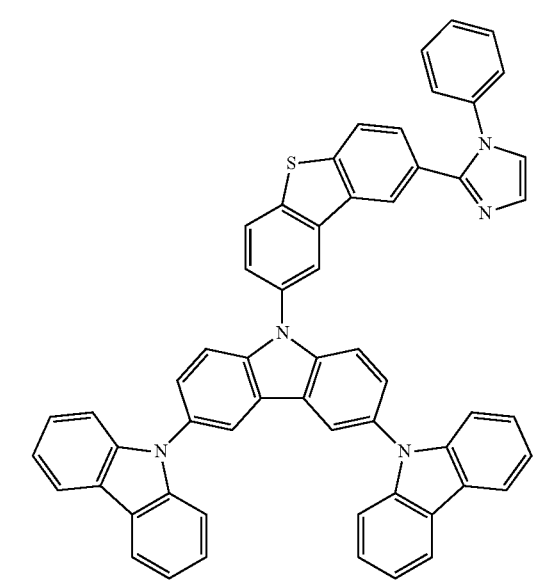

(66)
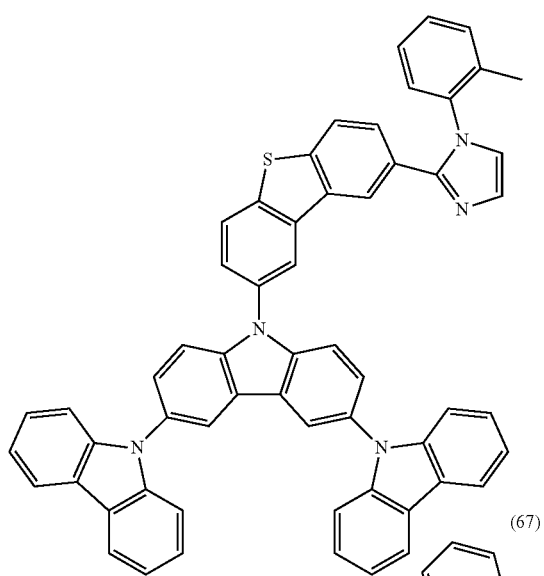
(67)
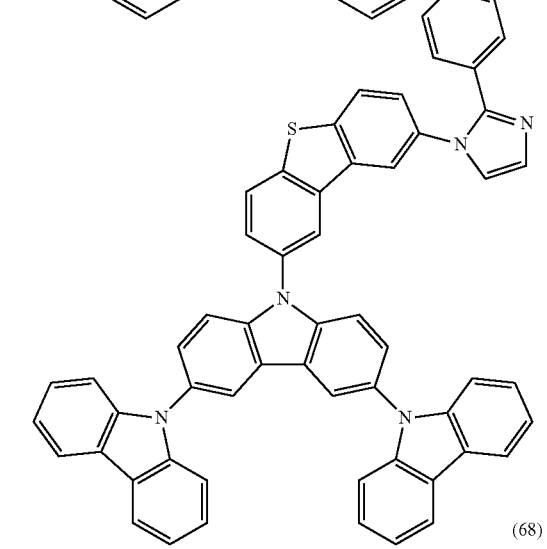
(68)
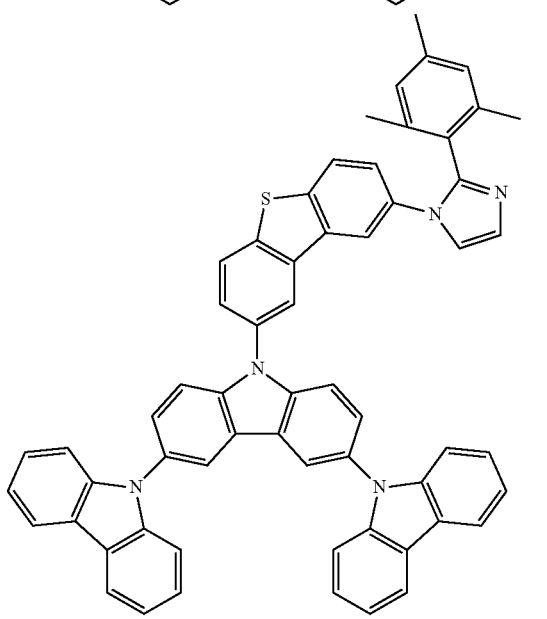
(69)
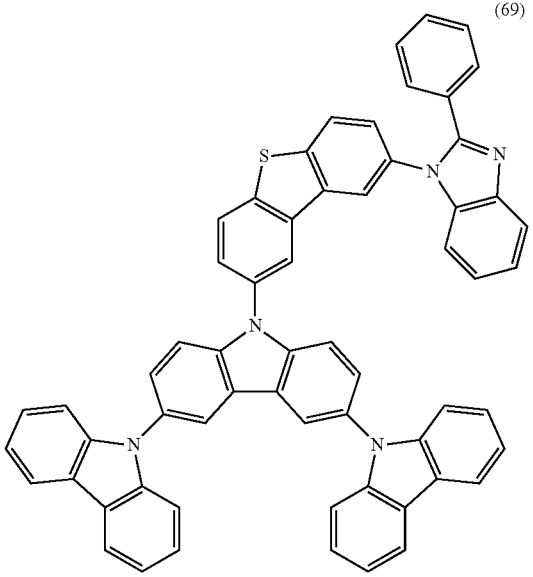
(70)
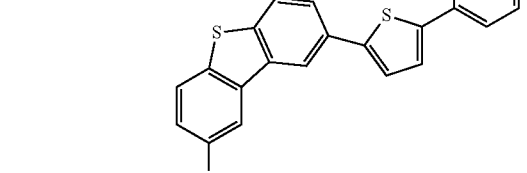
(71)
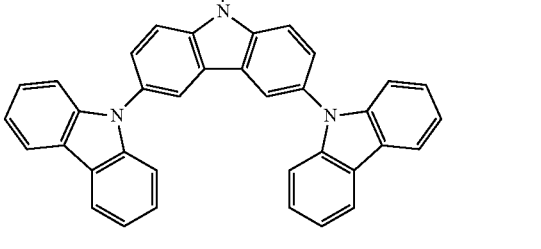

(72)
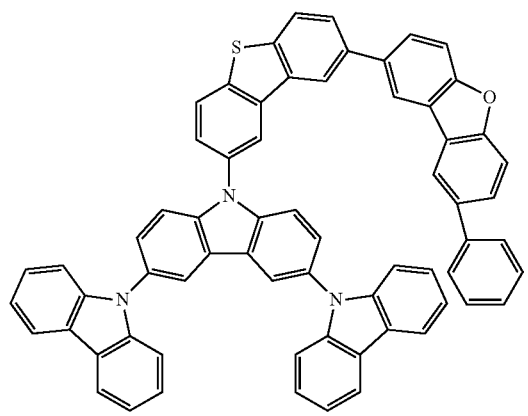
(73)
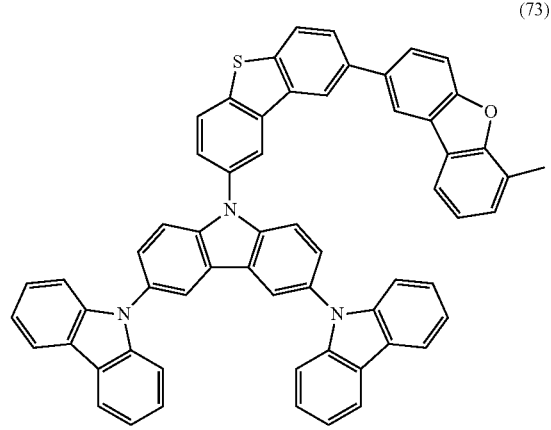
(74)
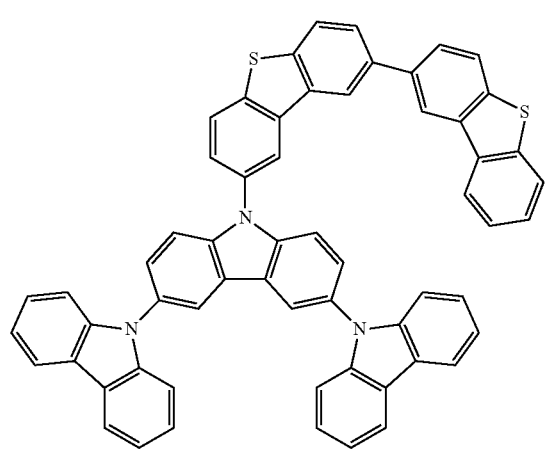
(75)
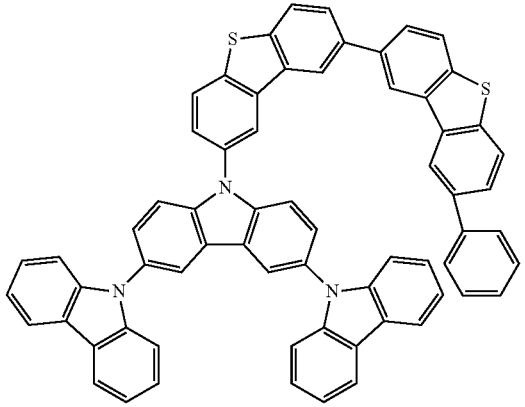
[Chem. 9]
(76)
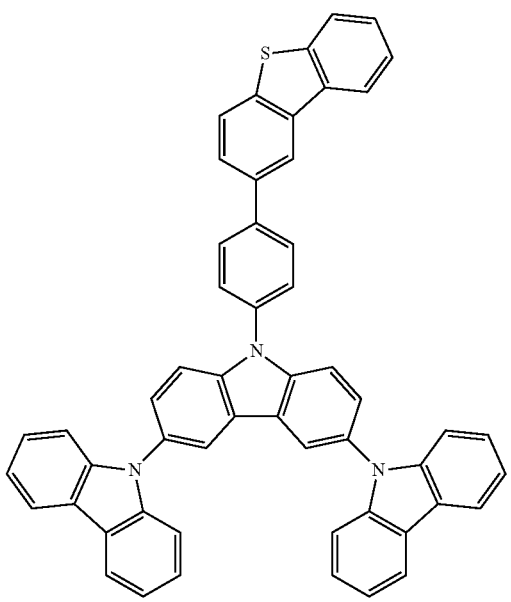
(77)
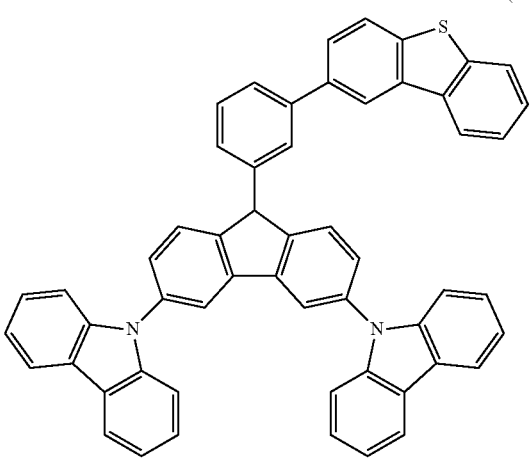

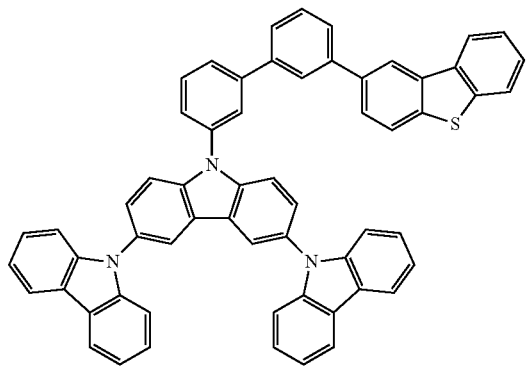
(78)
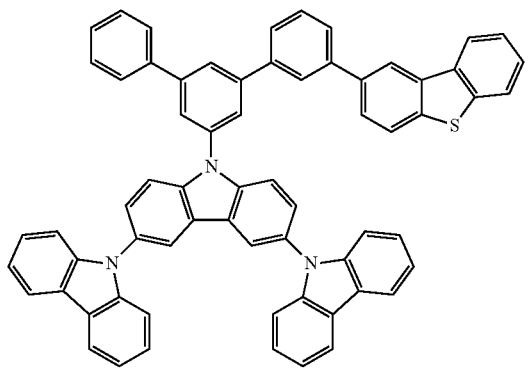
(81)
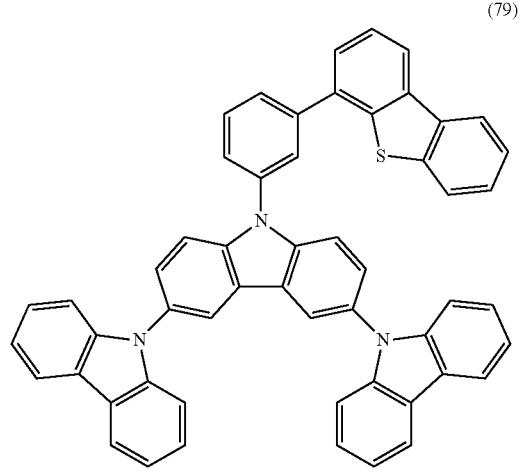
(79)
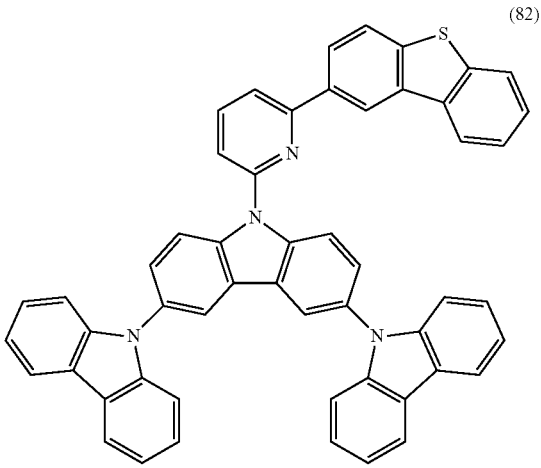
(82)
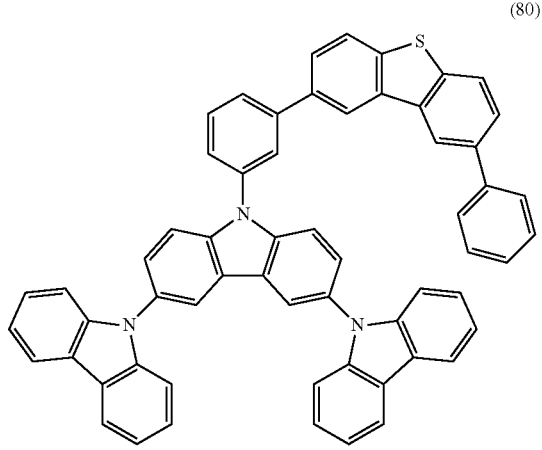
(80)
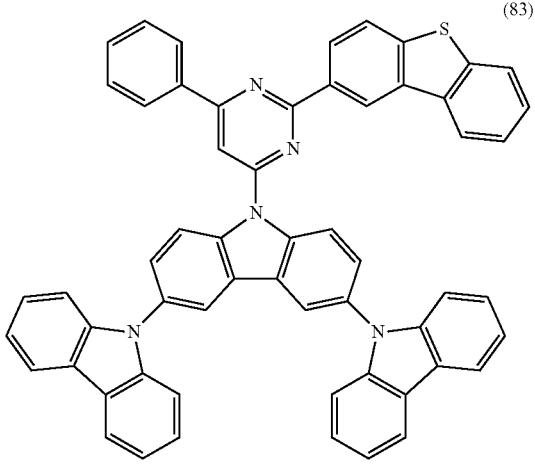
(83)

(84)
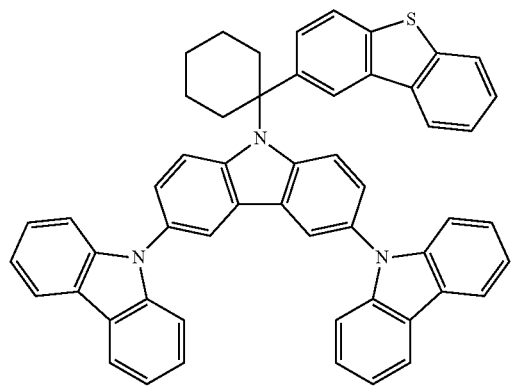
(85)
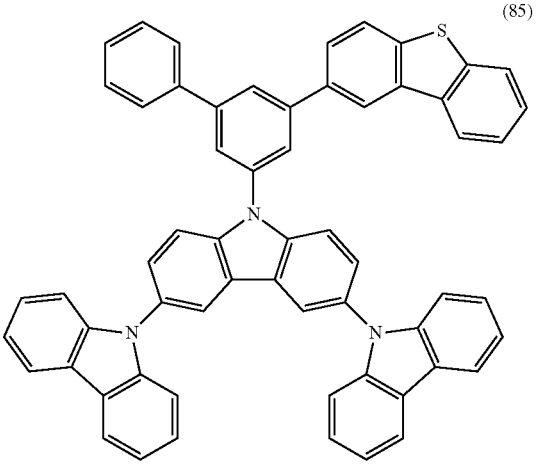
(86)
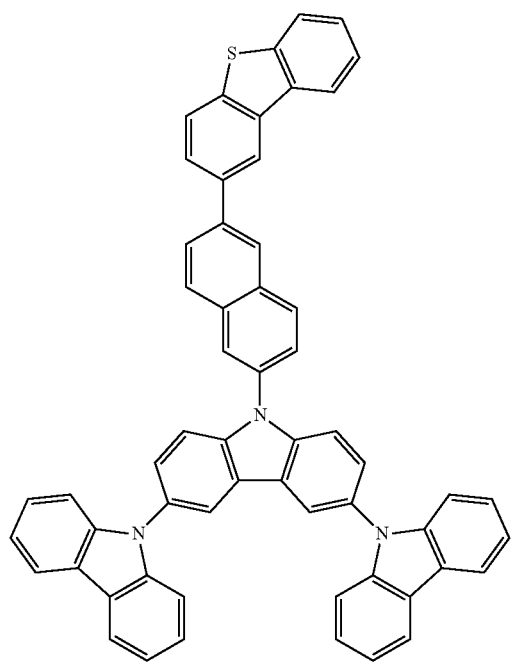
(87)
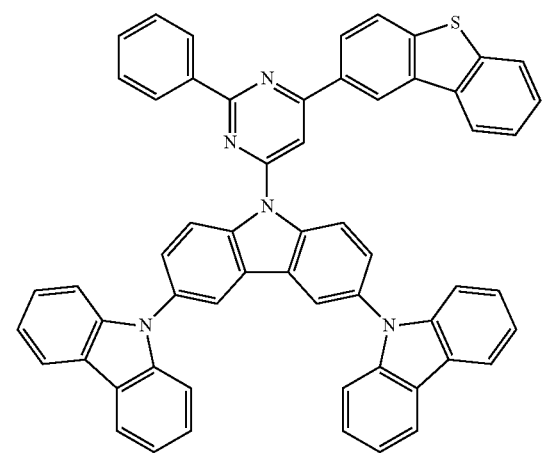
(88)
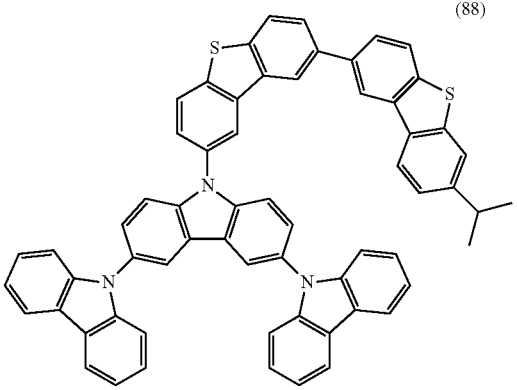
(89)
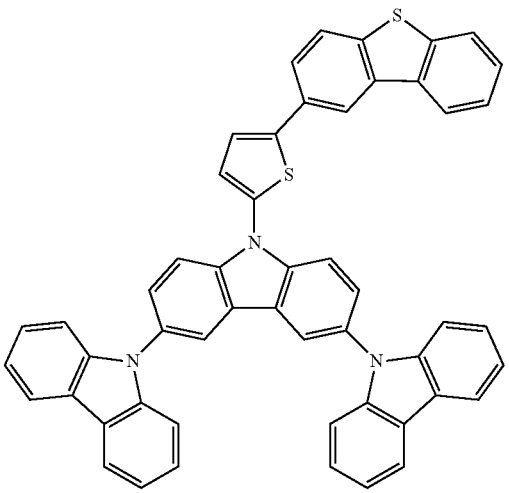

(90)

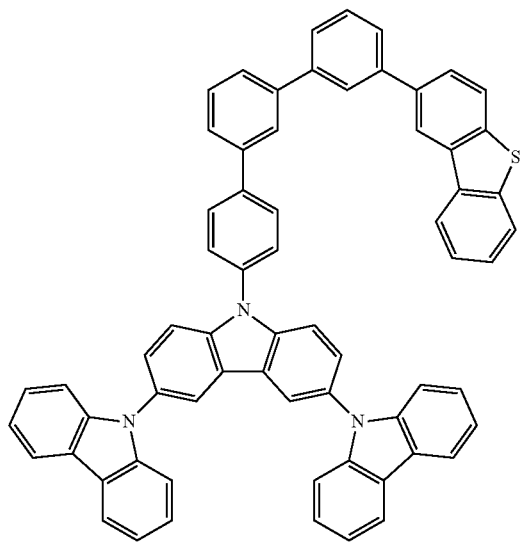

Of the above-mentioned compounds, preferred are Compounds (1), (2), (3), (5), (7), (15), (27), (28), (29), (30), (31), (32), (33), (35), (43), and (45), and more preferred are Compounds (1), (2), (5), (7), (15), (27), (28), (29), (30), (31), (32), (33), (35), and (43).

The material for an organic EL device of the present invention is preferably a host material to be incorporated into the light emitting layer of an organic EL device.

Next, the organic EL device of the present invention is described.

The organic EL device of the present invention includes one or more organic thin film layers including a light emitting layer between a cathode and an anode, in which at least one layer of the organic thin film layers contains the material for an organic electroluminescence device of the present invention.

A multi-layer type organic EL device is obtained by laminating a plurality of layers; for example, the device is formed of an anode, a hole transporting layer (a hole injecting layer), a light emitting layer, and a cathode, of an anode, a light emitting layer, an electron transporting layer (an electron injecting layer), and a cathode, of an anode, a hole transporting layer (a hole injecting layer), a light emitting layer, an electron transporting layer (an electron injecting layer), and a cathode, or of an anode, a hole transporting layer (a hole injecting layer), a light emitting layer, a hole blocking layer, an electron transporting layer (an electron injecting layer), and a cathode.

In the organic EL device of the present invention, the light emitting layer preferably contains the material for an organic EL device represented by the general formula (1) as a host material, and more preferably further contains a phosphorescent light emitting material. In addition, when the organic EL device of the present invention has a hole transporting layer (hole injecting layer), the material for an organic EL device of the present invention can be preferably incorporated into the hole transporting layer (hole injecting layer).

The phosphorescent light emitting material is preferably a compound containing a metal selected from iridium (Ir), osmium (Os), and platinum (Pt) because the compound has a high phosphorescent quantum yield, and can additionally improve the external quantum efficiency of the light emitting device. The material is more preferably a metal complex such as an iridium complex, an osmium complex, or a platinum complex. Of those, the iridium complex and the platinum complex are still more preferred. The metal complex is preferably an orthometalated metal complex in which a central metal atom and a carbon atom in a ligand are orthometal-bonded, and is more preferably an orthometalated iridium complex. More preferred forms of the orthometalated metal complex include the following iridium complexes.

[Chem. 10]

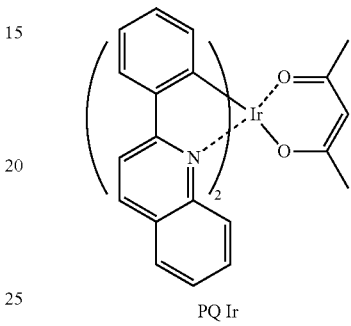

PQ Ir

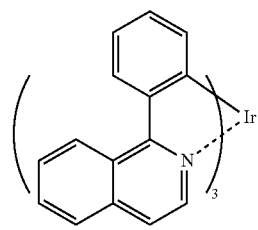

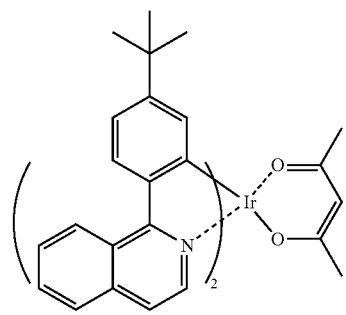

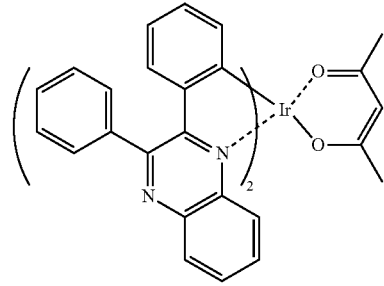

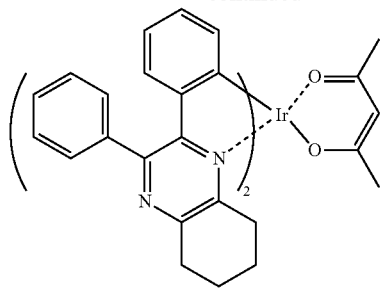
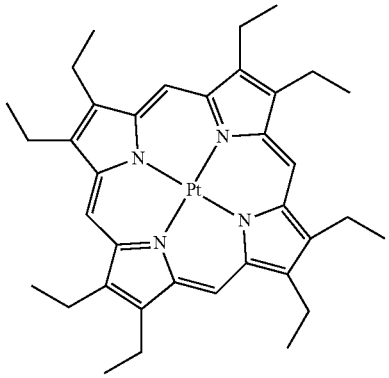
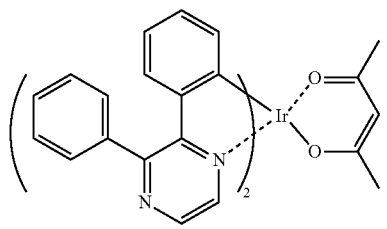
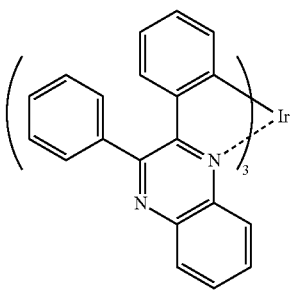
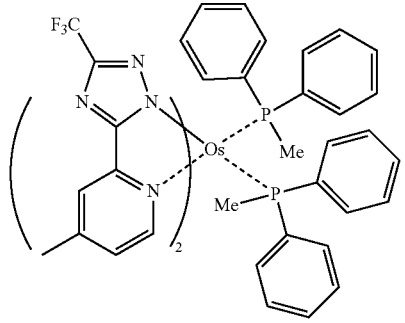
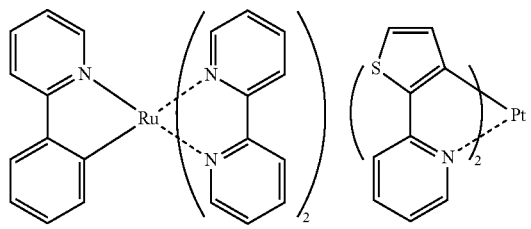
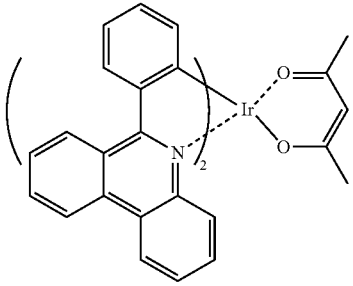
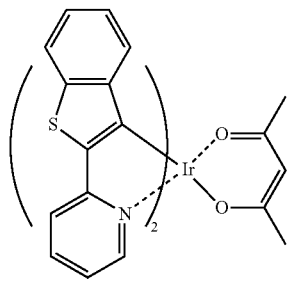
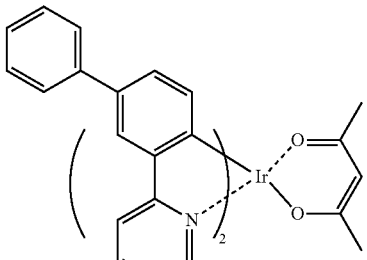
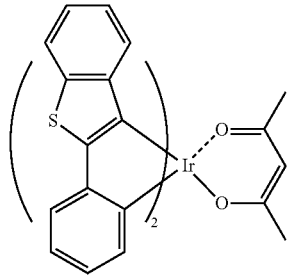
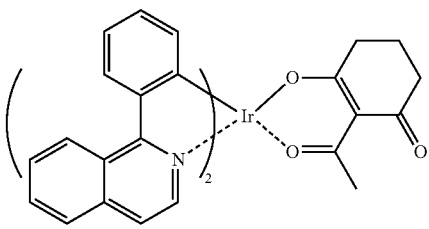

[Chem. 11]
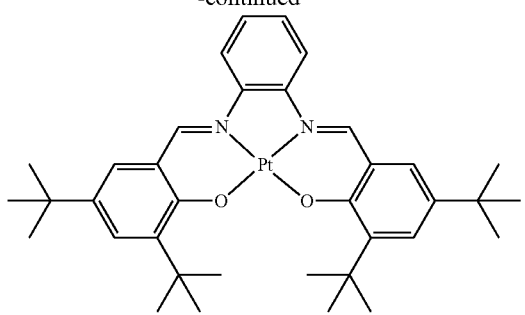
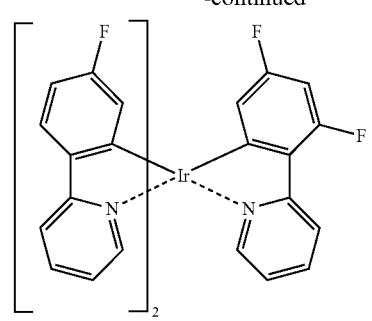
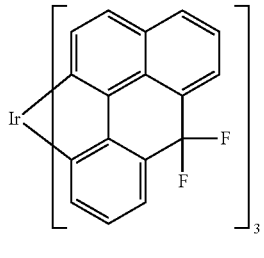
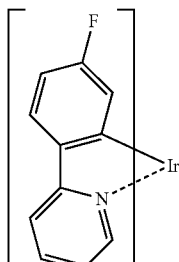
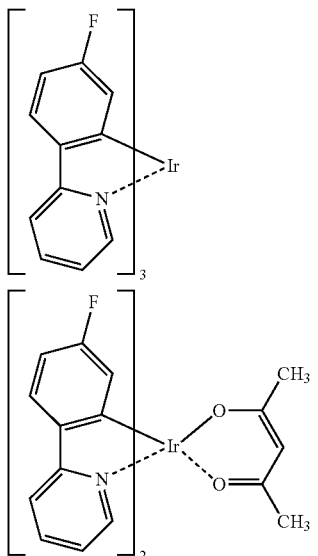
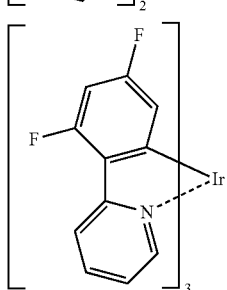
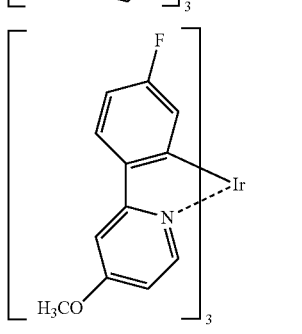
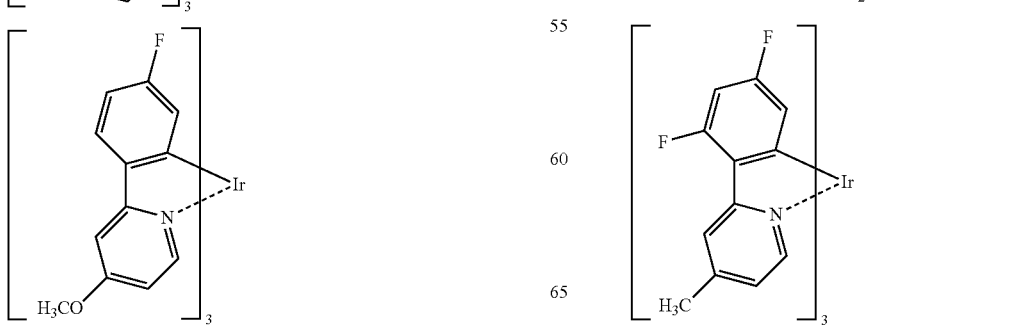

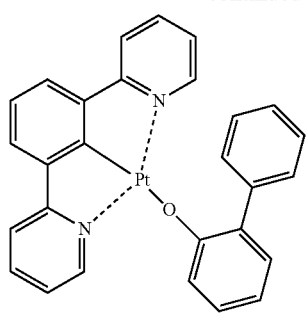
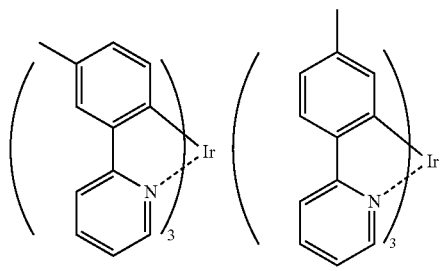
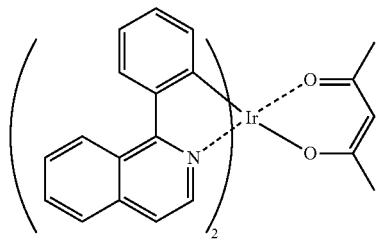
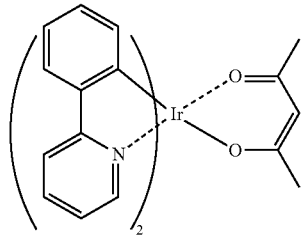
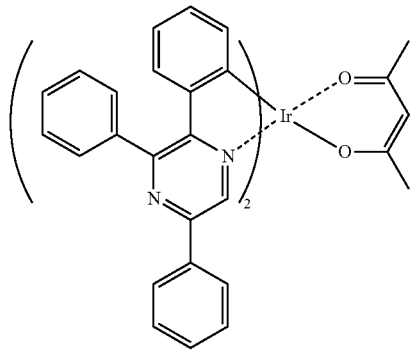
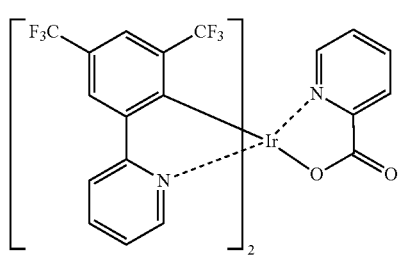
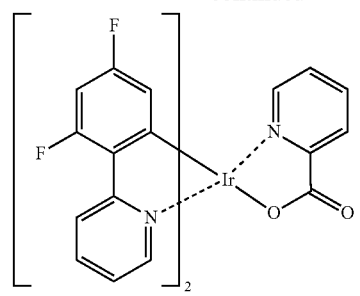
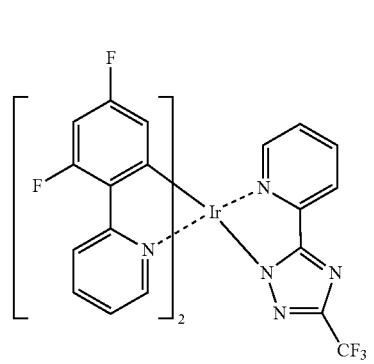
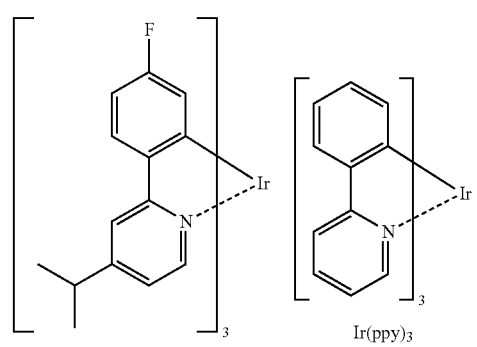
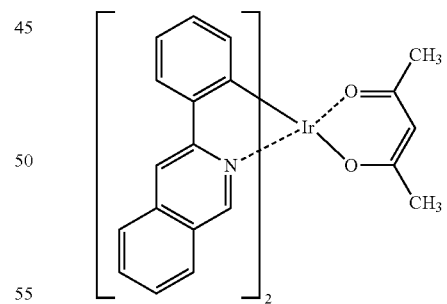
[Chem. 12]
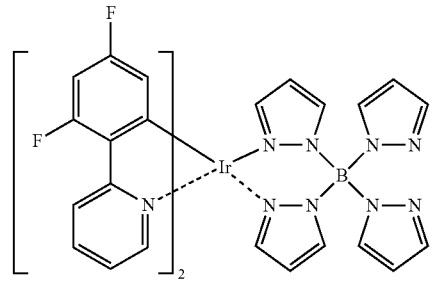

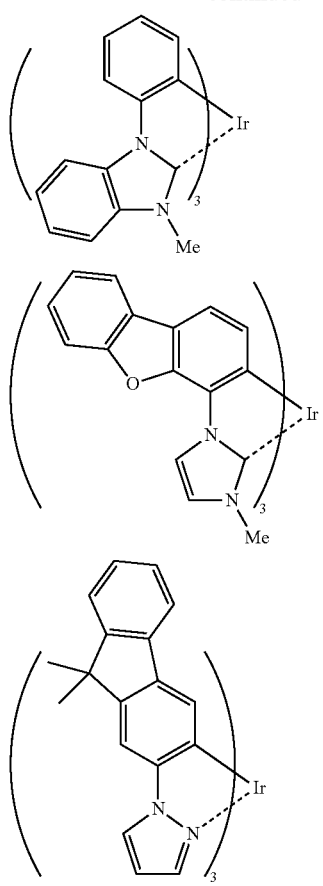
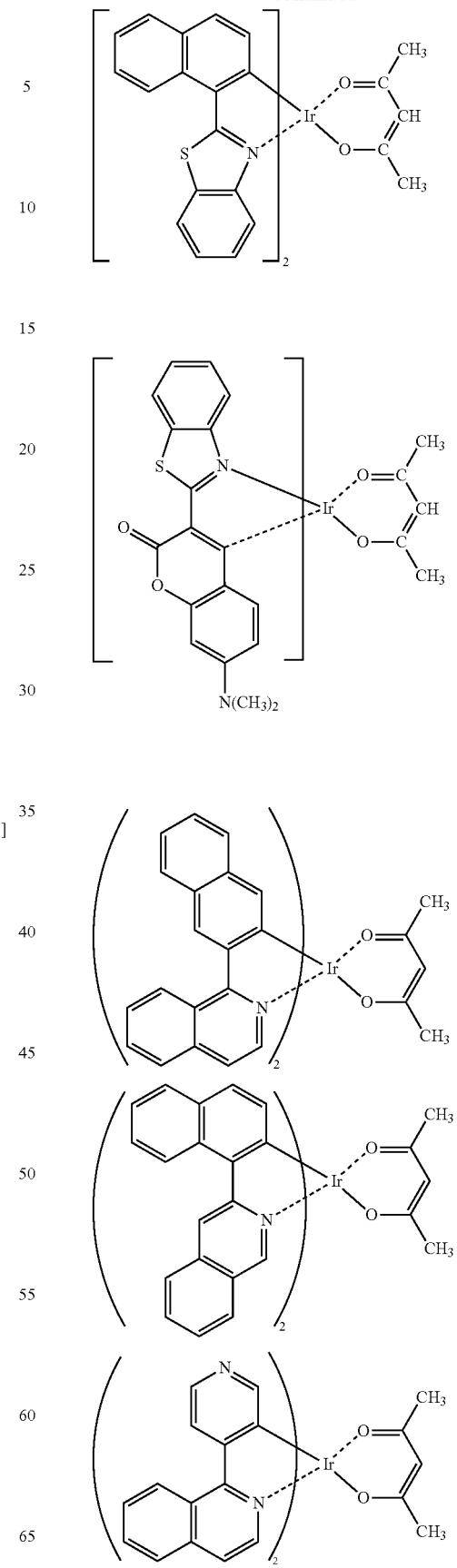

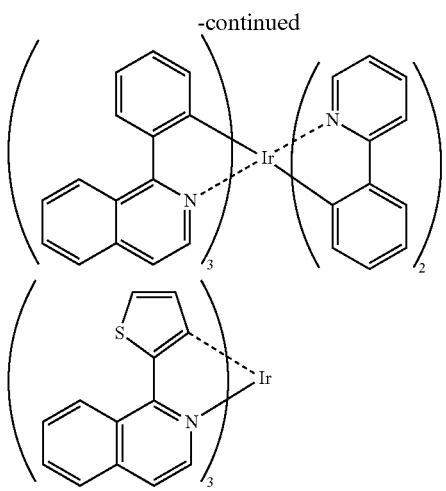

In addition, the organic EL device of the present invention is preferably such that the light emitting layer contains a host material containing the material for an organic EL device of the present invention and a phosphorescent light emitting material, and contains, as the phosphorescent light emitting material, such a blue metal complex that a local maximum value for its emission wavelength is 500 nm or less.

It is also preferred that the organic EL device of the present invention have a hole transporting layer (hole injecting layer) and the hole transporting layer (hole injecting layer) contain the material for an organic EL device of the present invention.

The organic EL device of the present invention preferably has a reductive dopant in an interfacial region between the cathode and an organic thin film layer. Examples of the reductive dopant include at least one kind selected from alkali metals, alkali metal complexes, alkali metal compounds, alkaline earth metals, alkaline earth metal complexes, alkaline earth metal compounds, rare earth metals, rare earth metal complexes, and rare earth metal compounds.

Examples of the alkali metal include Na having a work function of 2.36 eV, K having a work function of 2.28 eV, Rb having a work function of 2.16 eV, and Cs having a work function of 1.95 eV. An alkali metal having a work function of 2.9 eV or less is particularly preferred. Of those, K, Rb, and Cs are preferred, Rb or Cs is more preferred, and Cs is most preferred.

Examples of the alkaline earth metal include Ca having a work function of 2.9 eV, Sr having a work function of 2.0 to 2.5 eV, and Ba having a work function of 2.52 eV. An alkaline earth metal having a work function of 2.9 eV or less is particularly preferred.

Examples of the rare earth metal include Sc, Y, Ce, Tb, and Yb. A rare earth metal having a work function of 2.9 eV or less is particularly preferred.

Of those metals, a preferred metal has a particularly high reductive ability, and hence improvement of light emission luminance and long life of an organic EL device can be attained by adding a relatively small amount of the metal to an electron injecting region.

Examples of the alkali metal compound include an alkali oxide such as $Li_2O$, $Cs_2O$, or $K_2O$ and an alkali halide such as LiF, NaF, CsF, or KF. Of those, LiF, $Li_2O$, and NaF are preferred.

Examples of the alkaline earth metal compound include BaO, SrO, CaO, and mixtures thereof such as $Ba_xSr_{1-x}O$ ($0<x<1$) and $Ba_xCa_{1-x}O$ ($0<x<1$). Of those, BaO, SrO, and CaO are preferred.

Examples of the rare earth metal compound include $YbF_3$, $ScF_3$, $ScO_3$, $Y_2O_3$, $Ce_2O_3$, $GdF_3$, and $TbF_3$. Of those, $YbF_3$, $ScF_3$, and $TbF_3$ are preferred.

The alkali metal complex, alkaline earth metal complex, and rare earth metal complex are not particularly limited as long as they each contain, as a metal ion, at least one of alkali metal ions, alkaline earth metal ions, and rare earth metal ions. Further, a ligand is preferably quinolinol, benzoquinolinol, acrydinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bibyridyl, phenanthroline, phthalocyanine, porphyrin, cyclopentadiene, a β-diketone, an azomethine, a derivative thereof, or the like. However, the ligand is not limited thereto.

For the addition form of the reductive dopant, it is preferred that the reductive dopant be formed in a shape of a layer or an island in the interfacial region. A preferred example of the forming method is a method in which an organic substance which is a light emitting material or an electron injecting material for forming the interfacial region is deposited at the same time as the reductive dopant is deposited by a resistant heating deposition method, thereby dispersing the reductive dopant in the organic substance. The disperse concentration by molar ratio of the organic substance to the reductive dopant is 100:1 to 1:100, preferably 5:1 to 1:5. In a case where the reductive dopant is formed into the shape of a layer, the light emitting material or electron injecting material which serves as an organic layer in the interface is formed into the shape of a layer. After that, the reductive dopant is solely deposited by the resistant heating deposition method to form a layer preferably having a thickness of 0.1 to 15 nm. In a case where the reductive dopant is formed into the shape of an island, the light emitting material or electron injecting material which serves as an organic layer in the interface is formed into the shape of an island. After that, the reductive dopant is solely deposited by the resistant heating deposition method to form an island preferably having a thickness of 0.05 to 1 nm.

It is preferred that the organic EL device of the present invention have an electron injecting layer between the light emitting layer and the cathode, and the electron injecting layer contain a nitrogen-containing heterocyclic derivative as a main component. An electron transporting material to be used in the electron injecting layer is preferably an aromatic heterocyclic compound containing one or more heteroatoms in its molecules, particularly preferably a nitrogen-containing heterocyclic derivative.

The nitrogen-containing heterocyclic derivative is preferably, for example, a nitrogen-containing heterocyclic metal chelate complex represented by the formula (A).

[Chem. 14]

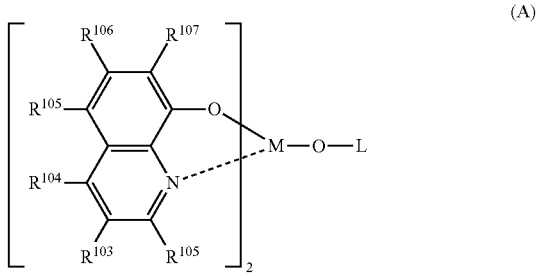

(A)

$R^{102}$ to $R^{107}$ each independently represent a hydrogen atom, a halogen atom, an amino group, a hydrocarbon group having 1 to 40 carbon atoms, an alkoxy group, an aryloxy group, an alkoxycarbonyl group, or a heterocyclic group, each of which may be substituted.

Examples of the halogen atom include a fluorine atom, a chlorine atom, a bromine atom, and an iodine atom. Further, examples of the amino group which may be substituted include the same examples as those described for the alkylamino group and arylamino group. In addition, the amino group which may be substituted may be an aralkylamino group.

Examples of the hydrocarbon group having 1 to 40 carbon atoms include a substituted or unsubstituted alkyl group, cycloalkyl group, and aryl group. Examples of the alkyl group, alkenyl group, cycloalkyl group, alkoxy group, aryl group, heterocyclic group, aralkyl group, and aryloxy group include the same examples as those described above. Examples of the alkenyl group include groups corresponding to the above-mentioned alkyl groups. Examples of the aralkyl group include the above-mentioned alkyl group substituted with the above-mentioned aryl group. The alkoxycarbonyl group is represented as —COOY', and examples of the group represented by Y' include the same examples as those described for the alkyl group.

M represents aluminum (Al), gallium (Ga), or indium (In), preferably In.

L in the formula (A) represents a group represented by the following formula (A') or (A").

[Chem. 15]

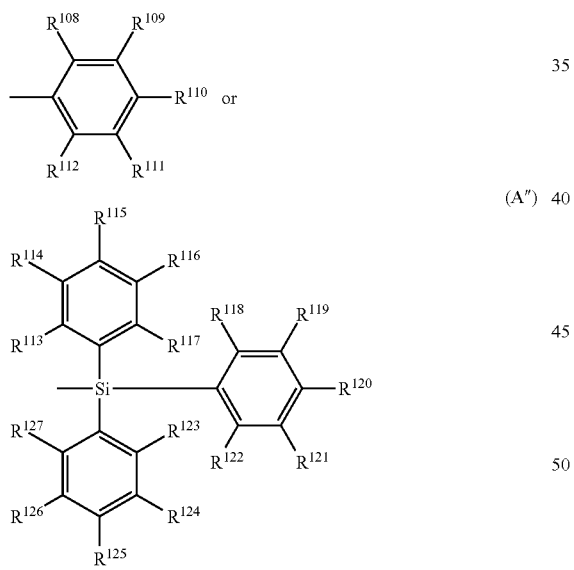

(A")

In the formula, $R^{108}$ to $R^{112}$ each independently represent a hydrogen atom or a substituted or unsubstituted hydrocarbon group having 1 to 40 carbon atoms, and groups adjacent to each other may form a cyclic structure. In addition, $R^{113}$ to $R^{127}$ each independently represent a hydrogen atom or a substituted or unsubstituted hydrocarbon group having 1 to 40 carbon atoms, and groups adjacent to each other may form a cyclic structure.

Examples of the hydrocarbon group having 1 to 40 carbon atoms represented by any one of $R^{108}$ to $R^{112}$ and $R^{113}$ to $R^{127}$ in the formula (A') and the formula (A") include the same examples as the specific examples of $R^1$ to $R^8$.

In addition, a divalent group in the case where groups adjacent to each other out of $R^{108}$ to $R^{112}$ and $R^{113}$ to $R^{127}$ and form a cyclic structure is, for example, a tetramethylene group, a pentamethylene group, a hexamethylene group, a diphenylmethane-2,2'-diyl group, a diphenylethane-3,3'-diyl group, or a diphenylpropane-4,4'-diyl group.

Specific examples of the nitrogen-containing heterocyclic metal chelate complex represented by the formula (A) are shown below, but the present invention is not limited to these exemplified compounds.

[Chem. 16]

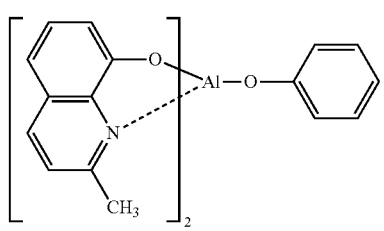
(A-1)

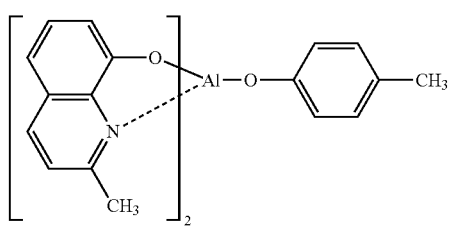
(A-2)

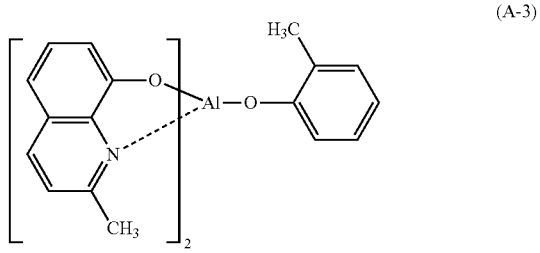
(A-3)

(A-4)

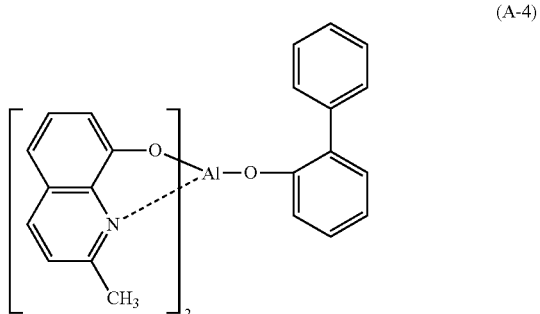
(A-5)

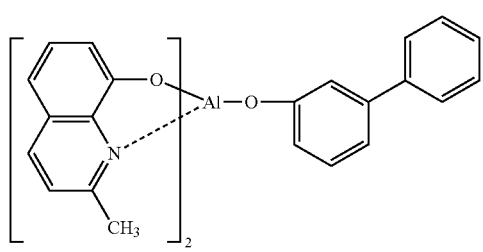
(A-6)
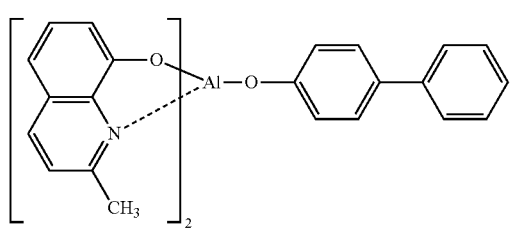
(A-7)
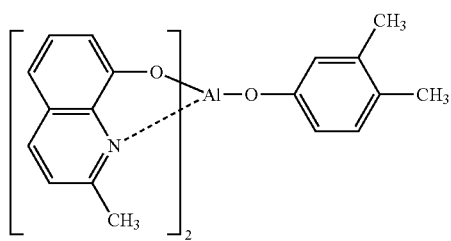
(A-8)
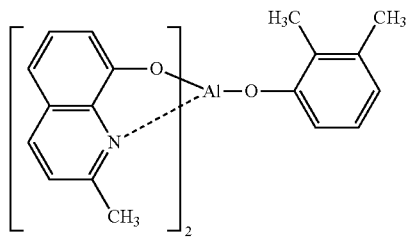
(A-9)
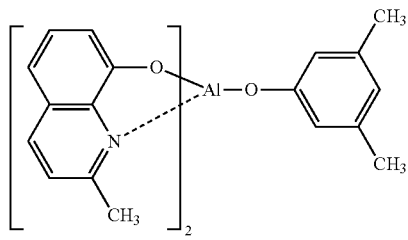
(A-10)
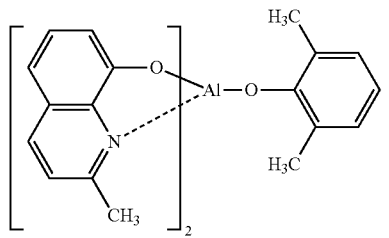
(A-11)
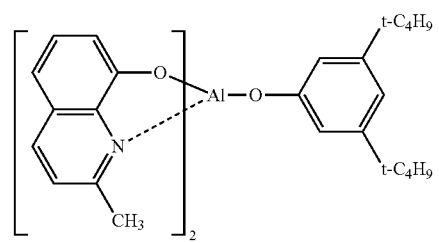
(A-12)
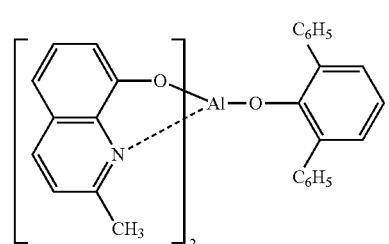
(A-13)
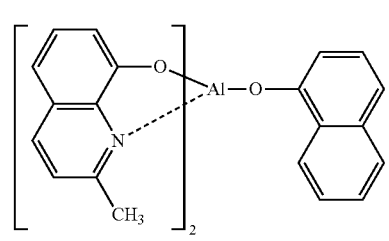
(A-14)
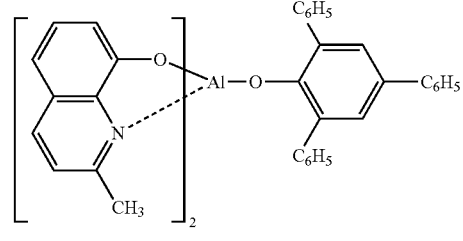
(A-15)
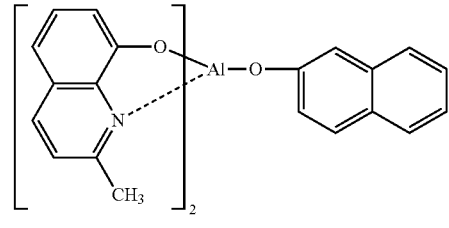
(A-16)
[Chem. 17]
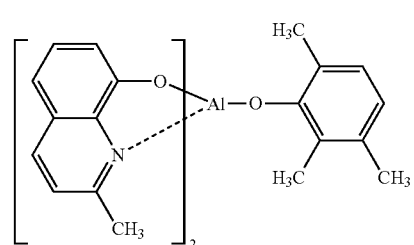
(A-17)

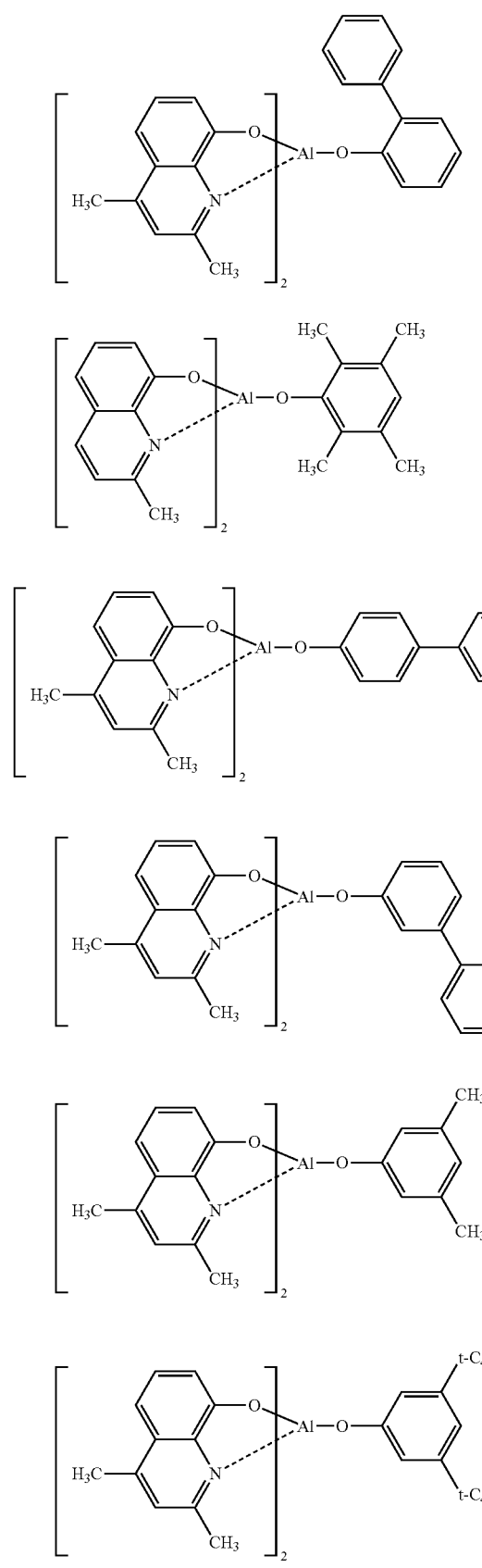
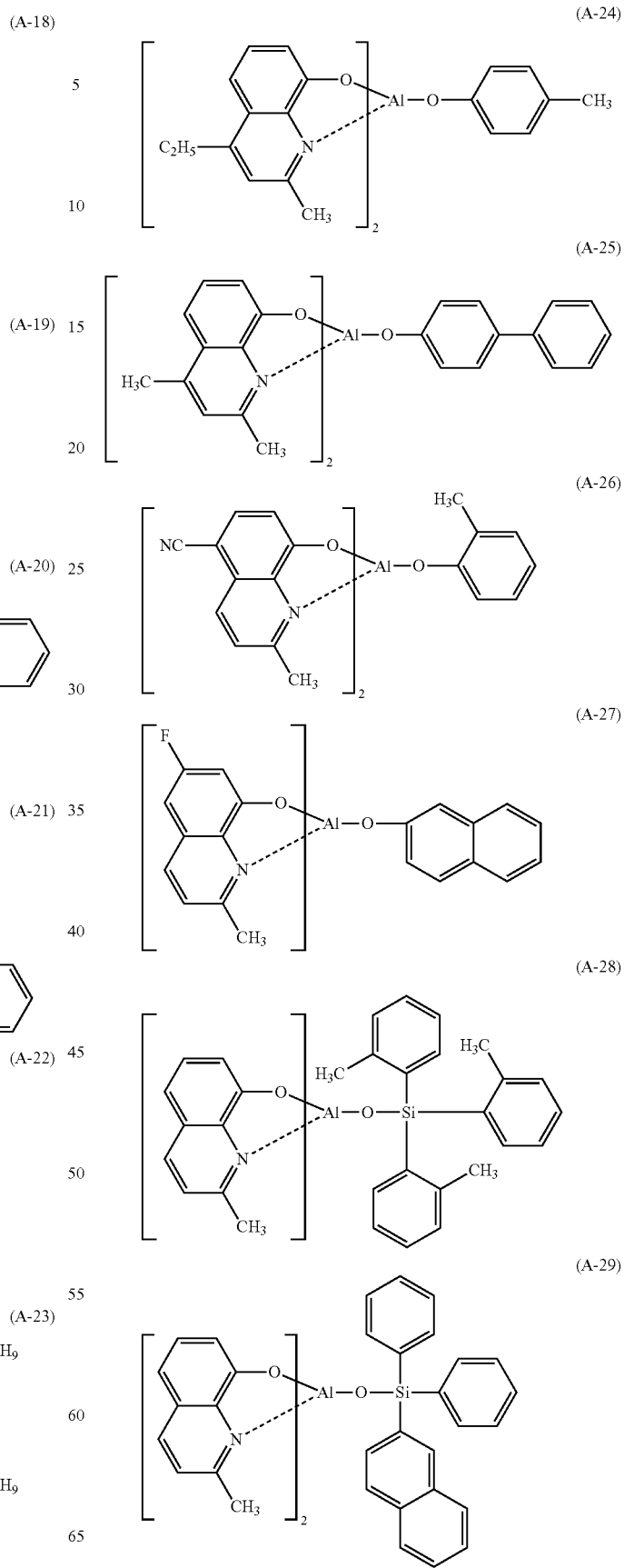

(A-30)

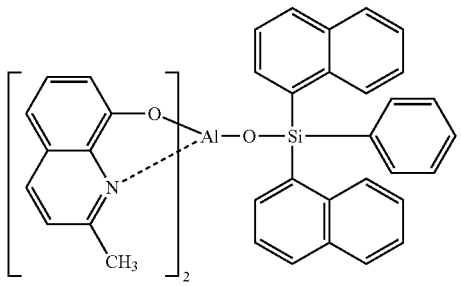

(A-36)

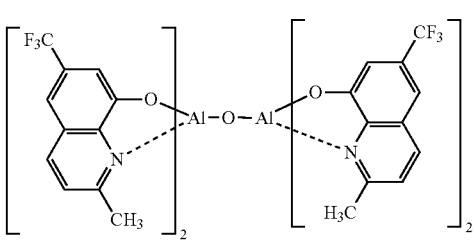

[Chem. 18]

(A-31)

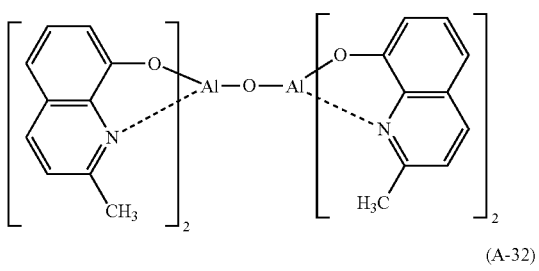

The nitrogen-containing heterocyclic derivative is a nitrogen-containing heterocyclic derivative formed of an organic compound having any one of the following general formulae, and a nitrogen-containing compound which is not a metal complex is also an example of the derivative. The derivative is, for example, a derivative which have a five- or six-membered ring containing a skeleton represented by the following formula (a) or a derivative whose structure is represented by the following formula (b).

[Chem. 19]

(a)

(b)

In the formula (b), X represents a carbon atom or a nitrogen atom, and $Z^1$ and $Z^2$ each independently represent an atomic group capable of forming a nitrogen-containing heterocycle.

An organic compound having a nitrogen-containing aromatic polycycle formed of a five- or six-membered ring is preferred. In the case of such nitrogen-containing aromatic polycycle having a plurality of nitrogen atoms, a nitrogen-containing aromatic polycyclic organic compound having a skeleton obtained by combining the above-mentioned formulae (a) and (b) is more preferred.

The nitrogen-containing group of the nitrogen-containing organic compound is selected from, for example, nitrogen-containing heterocyclic groups represented by the following general formulae.

(A-32)

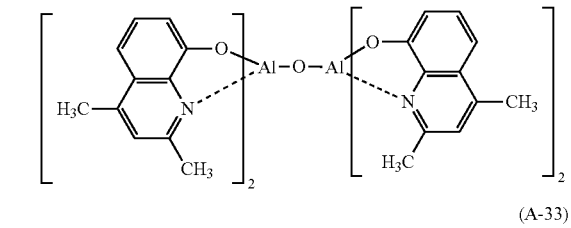

(A-33)

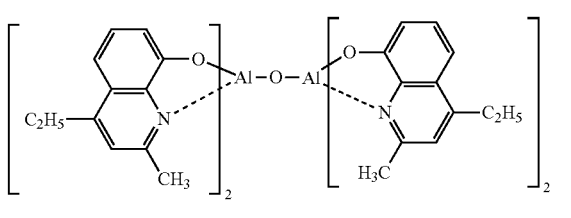

(A-34)

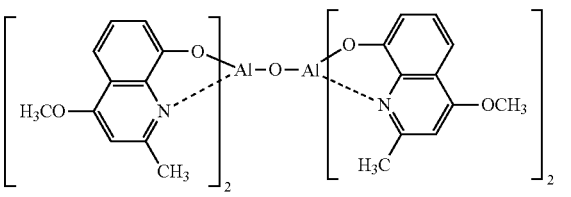

[Chem. 20]

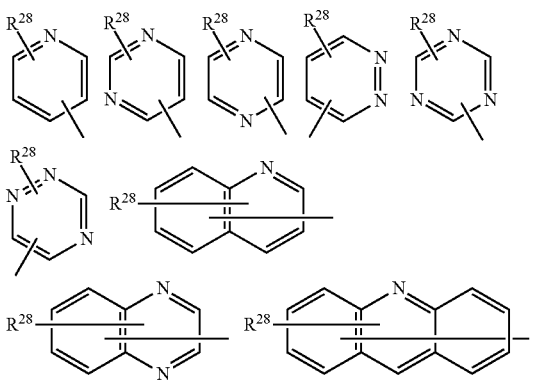

(A-35)

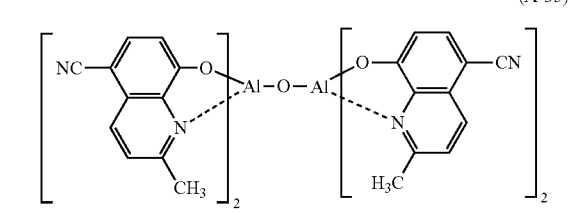

-continued

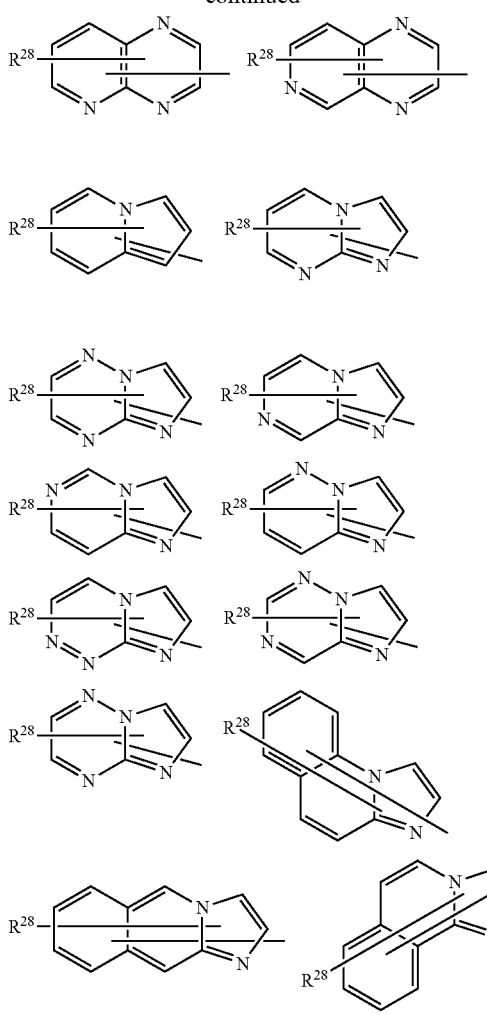

(In each of the formulae, n $R^{28}$'s exist and each represent an aryl group having 6 to 40 carbon atoms, a heteroaryl group having 3 to 40 carbon atoms, an alkyl group having 1 to 20 carbon atoms, or an alkoxy group having 1 to 20 carbon atoms, n, which represents the number of $R^{28}$'s represents an integer of 0 to 5, and when the n represents an integer of 2 or more, a plurality of $R^{28}$'s may be identical to or different from each other.)

Further, a preferred specific compound is, for example, a nitrogen-containing heterocyclic derivative represented by the following formula.

$HAr^a\text{-}L^b\text{-}Ar^b\text{—}Ar^c$ [Chem. 21]

(In the formula, $HAr^a$ represents a nitrogen-containing heterocycle which has 3 to 40 carbon atoms and which may have a substituent, $L^b$ represents a single bond, an arylene group which has 6 to 40 carbon atoms and which may have a substituent, or a heteroarylene group which has 3 to 40 carbon atoms and which may have a substituent, $Ar^b$ represents a divalent aromatic hydrocarbon group which has 6 to 40 carbon atoms and which may have a substituent, and $Ar^c$ represents an aryl group which has 6 to 40 carbon atoms and which may have a substituent, or a heteroaryl group which has 3 to 40 carbon atoms and which may have a substituent.)

$HAr^a$ represents a group, for example, selected from the following group.

[Chem. 22]

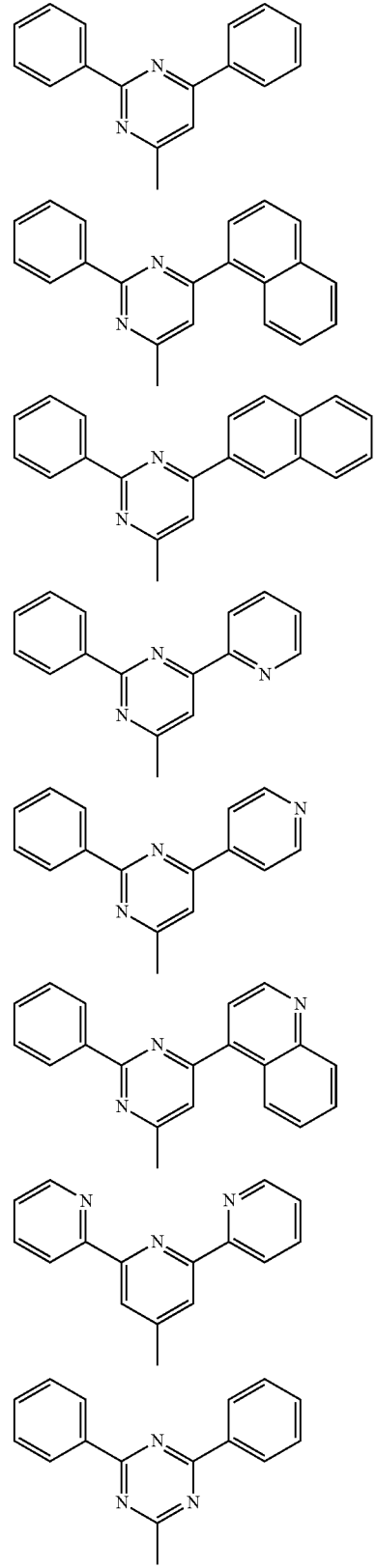

-continued

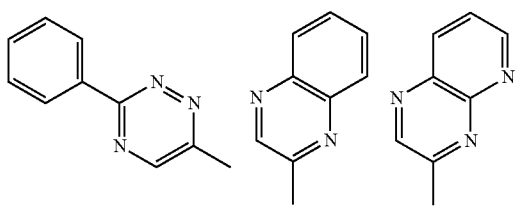

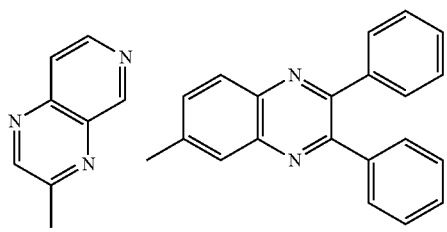

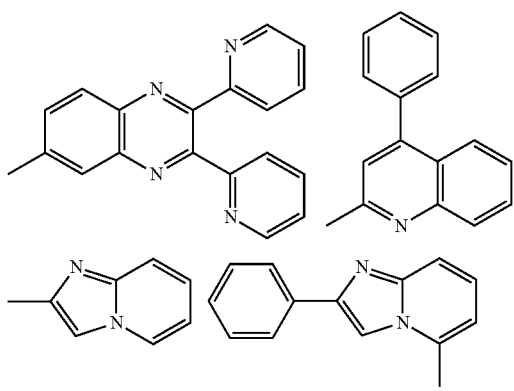

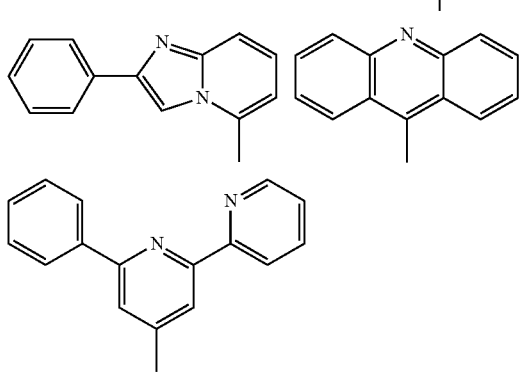

L⁶ represents a group, for example, selected from the following group.

[Chem. 23]

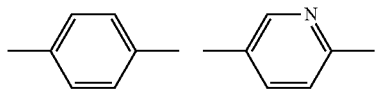

Ar^c represents a group, for example, selected from the following group.

[Chem. 24]

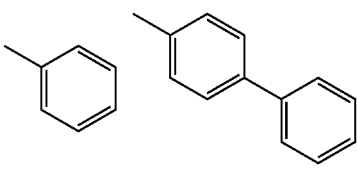

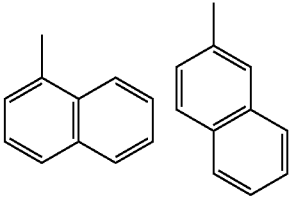

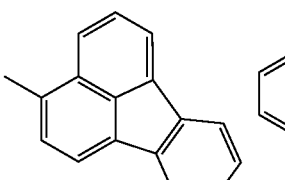

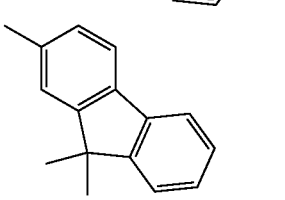

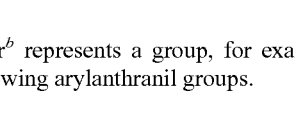

Ar^b represents a group, for example, selected from the following arylanthranil groups.

[Chem. 25]

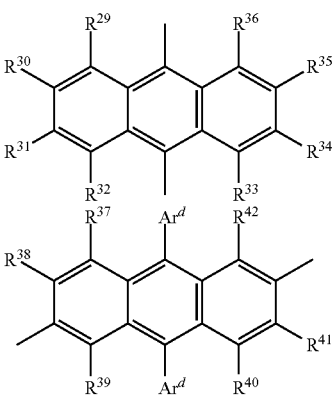

(In the formulae, $R^{29}$ to $R^{42}$ each independently represent a hydrogen atom, a halogen atom, an alkyl group having 1 to 20 carbon atoms, an alkoxy group having 1 to 20 carbon atoms, an aryloxy group having 6 to 40 carbon atoms, an aryl group which has 6 to 40 carbon atoms and which may have a substituent, or a heteroaryl group having 3 to 40 carbon atoms, and $Ar^d$ represents an aryl group which has 6 to 40 carbon atoms and which may have a substituent, or a heteroaryl group having 3 to 40 carbon atoms.)

In addition, a nitrogen-containing heterocyclic derivative in which $R^{29}$ to $R^{36}$ in $Ar^b$ represented by any one of the above-mentioned formulae each represent a hydrogen atom is preferred.

In addition to the foregoing, the following compound (see JP 09-3448 A) is also suitably used.

[Chem.26]

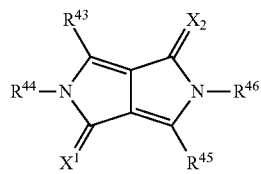

(In the formula, $R^{43}$ to $R^{46}$ each independently represent a hydrogen atom, a substituted or unsubstituted aliphatic group, a substituted or unsubstituted alicyclic group, a substituted or unsubstituted carbocyclic aromatic ring group, or a substituted or unsubstituted heterocyclic group, and $X^1$ and $X^2$ each independently represent an oxygen atom, a sulfur atom, or a dicyanomethylene group.)

In addition, the following compound (see JP 2000-173774 A) is also suitably used.

[Chem. 27]

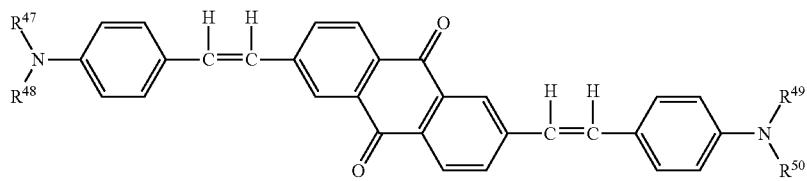

In the formula, $R^{47}$, $R^{48}$, $R^{49}$, and $R^{50}$ represent groups identical to or different from one another, and each represent an aryl group represented by the following formula.

[Chem. 28]

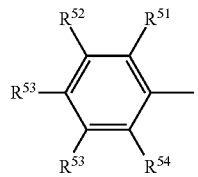

(In the formula, $R^{51}$, $R^{52}$, $R^{53}$, $R^{54}$, and $R^{55}$ represent groups identical to or different from one another, and each represent a hydrogen atom, or at least one thereof may represent a saturated or unsaturated alkoxyl, alkyl, amino, or alkylamino group.)

Further, a polymer compound containing the nitrogen-containing heterocyclic group or nitrogen-containing heterocyclic derivative is also permitted.

In addition, the electron transporting layer preferably contains at least one of the nitrogen-containing heterocyclic derivatives represented by the following formulae (201) to (203).

[Chem. 29]

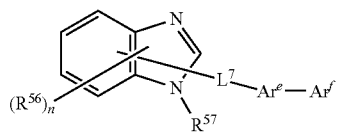

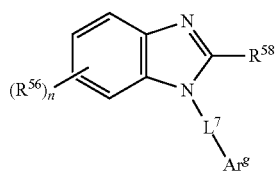

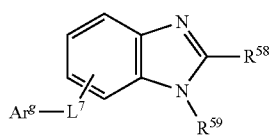

In the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, n represents an integer of 0 to 4, $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms, $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent, $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent, $Ar^e$ represents an arylene group which has 6 to 60 carbon atoms and which may have a substituent, a pyridinylene group which may have a substituent, or a quinolinylene group which may have a substituent, and $Ar^f$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

$Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —$Ar^e$—$Ar^f$ ($Ar^e$ and $Ar^f$ each have the same meaning as that described above).

It should be noted that, in the formulae (201) to (203), $R^{56}$ represents a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

The aryl group having 6 to 60 carbon atoms is preferably an aryl group having 6 to 40 carbon atoms, more preferably an aryl group having 6 to 20 carbon atoms. Specific examples thereof include a phenyl group, a naphthyl group, an anthryl group, a phenanthryl group, a naphthacenyl group, a chrysenyl group, a pyrenyl group, a biphenyl group, a terphenyl group, a tolyl group, a t-butylphenyl group, a (2-phenylpropyl)phenyl group, a fluoranthenyl group, a fluorenyl group, a monovalent group formed of spirobifluorene, a perfluorophenyl group, a perfluoronaphthyl group, a perfluoroanthryl group, a perfluorobiphenyl group, a monovalent group formed of 9-phenylanthracene, a monovalent group formed of 9-(1'-naphthyl)anthracene, a monovalent group formed of 9-(2'-naphthyl)anthracene, a monovalent group formed of 6-phenylchrysene, and a monovalent group formed of 9-[4-(diphenylamino)phenyl]anthracene. Of those, a phenyl group, a naphthyl group, a biphenyl group, a terphenyl group, a 9-(10-phenyl)anthryl group, a 9-[10-(1'-naphthyl)]anthryl group, and a 9-[10-(2'-naphthyl)]anthryl group are preferred.

The alkyl group having 1 to 20 carbon atoms is preferably an alkyl group having 1 to 6 carbon atoms. Specific examples thereof include a methyl group, an ethyl group, a propyl group, a butyl group, a pentyl group, and a hexyl group, and further include a haloalkyl group such as a trifluoromethyl group. The alkyl group having three or more carbon atoms may be linear, cyclic, or branched.

The alkoxy group having 1 to 20 carbon atoms is preferably an alkoxy group having 1 to 6 carbon atoms. Specific examples thereof include a methoxy group, an ethoxy group, a propoxy group, a butoxy group, a pentyloxy group, and a hexyloxy group. The alkoxy group having three or more carbon atoms may be linear, cyclic, or branched.

Examples of the substituent for each group represented by $R^{56}$ include a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, and a heteroaryl group which has 3 to 40 carbon atoms and which may have a substituent.

Examples of the halogen atom include fluorine, chlorine, bromine, and iodine.

Examples of the alkyl group having 1 to 20 carbon atoms, the alkoxy group having 1 to 20 carbon atoms, and the aryl group having 6 to 40 carbon atoms include the same groups as described above.

Examples of the aryloxy group having 6 to 40 carbon atoms include a phenoxy group and a biphenyloxy group.

Examples of the heteroaryl group having 3 to 40 carbon atoms include a pyrrolyl group, a furyl group, a thienyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, and a triazolyl group.

n represents an integer of 0 to 4, preferably 0 to 2.

In the formula (201), $R^{57}$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group having 1 to 20 carbon atoms.

Specific examples of each of those groups, preferred number of carbon atoms and substituents are the same as described for the R.

In the formulae (202) and (203), $R^{58}$ and $R^{59}$ each independently represent a hydrogen atom, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of each of those groups, preferred number of carbon atoms and substituents are the same as described for the $R^{56}$.

In the formulae (201) to (203), $L^7$ represents a single bond, an arylene group which has 6 to 60 carbon atoms and which may have a substituent, a pyridinylene group which may have a substituent, a quinolinylene group which may have a substituent, or a fluorenylene group which may have a substituent.

The arylene group having 6 to 60 carbon atoms is preferably an arylene group having 6 to 40 carbon atoms, more preferably an arylene group having 6 to 20 carbon atoms, and specific examples thereof include a divalent group produced by removing a hydrogen atom from the aryl group described for the R. Examples of the substituent for each of those groups represented by $L^7$ are the same as described for the $R^{56}$.

In addition, $L^7$ preferably represents a group selected from the group consisting of the following groups.

[Chem. 30]

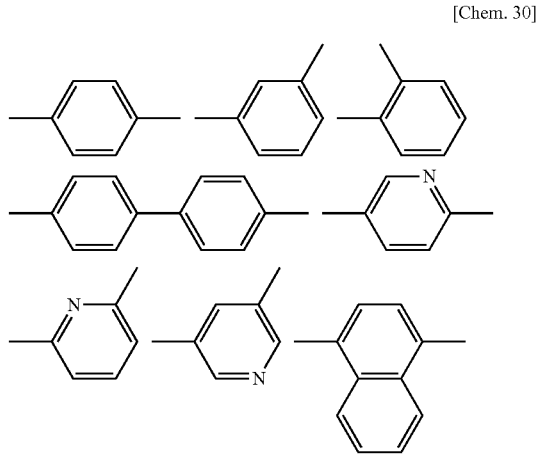

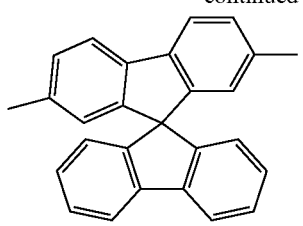

In the formula (201), Ar$^e$ represents an arylene group which has 6 to 60 carbon atoms and which may have a substituent, a pyridinylene group which may have a substituent, or a quinolinylene group which may have a substituent. Examples of the substituent for each group represented by Ar$^e$ and Ar$^g$ are the same as described for the R.

In addition, Ar$^e$ preferably represents a group selected from fused ring groups represented by the following formulae (101) to (110).

[Chem. 31]

(101)
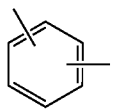

(102)
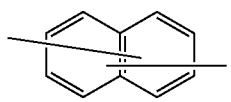

(103)
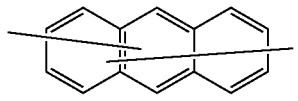

(104)
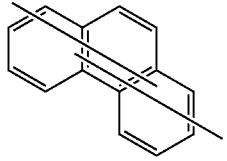

(105)
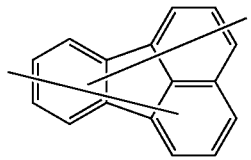

(106)
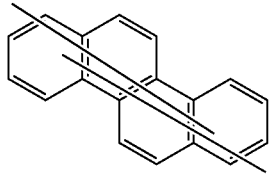

(107)
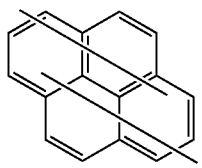

(108)
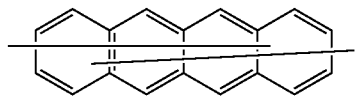

(109)
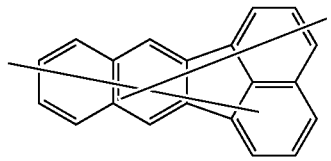

(110)
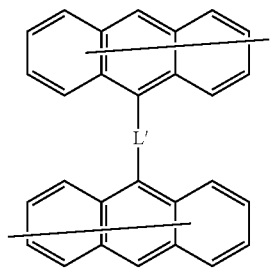

In the formulae (101) to (110), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from each other. Specific examples of each of those groups are the same as described above.

In the formula (110), L' represents a single bond, or a group selected from the group consisting of the following groups.

[Chem. 32]

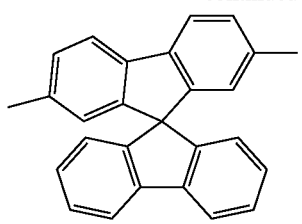
The formula (103) represented by $Ar^e$ is preferably a fused ring group represented by any one of the following formulae (111) to (125).
[Chem. 33]
(111)
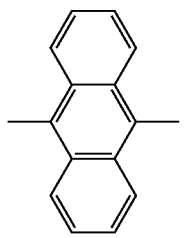
(112)
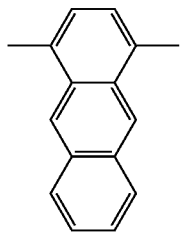
(113)
(114)
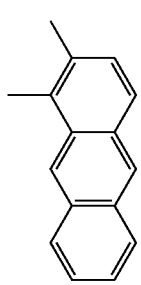
(115)
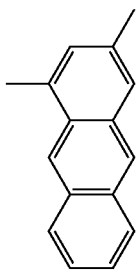
(116)
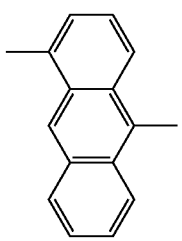
(117)
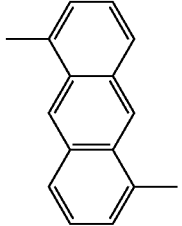
(118)
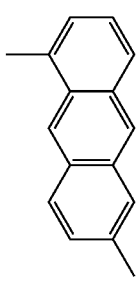
(119)
(120)
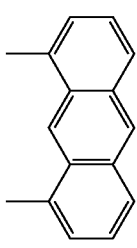

-continued

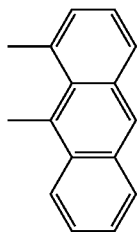
(121)

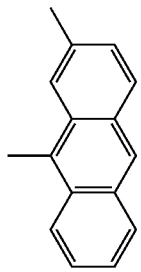
(122)

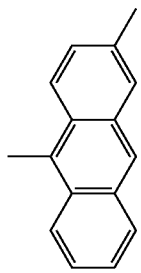
(123)

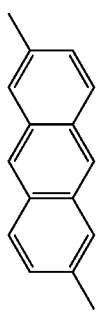
(124)

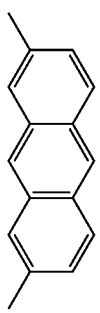
(125)

In the formulae (111) to (125), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from each other. Specific examples of each of those groups are the same as described above.

In the formula (201), $Ar^f$ represents, an aryl group which has 6 to 60 carbon atoms and which may have a substituent, a pyridyl group which may have a substituent, a quinolyl group which may have a substituent, an alkyl group which has 1 to 20 carbon atoms and which may have a substituent, or an alkoxy group which has 1 to 20 carbon atoms and which may have a substituent.

Specific examples of each of those groups, preferred number of carbon atoms and substituents are the same as described for the $R^{56}$.

In the formulae (202) and (203), $Ar^g$ represents an aryl group which has 6 to 60 carbon atoms and which may have a substituent, a pyridyl group which may have a substituent, a quinolyl group which may have a substituent, an alkyl group which has 1 to 20 carbon atoms and which may have a substituent, an alkoxy group which has 1 to 20 carbon atoms and which may have a substituent, or a group represented by —$Ar^e$—$Ar^f$ (each of $Ar^e$ and $Ar^f$ is the same as described above.)

Specific examples of each of those groups, preferred number of carbon atoms and substituents are the same as described for the $R^{56}$.

In addition, Arg preferably represents a group selected from fused ring groups represented by the following formulae (126) to (135).

[Chem. 34]

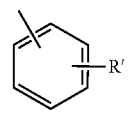
(126)

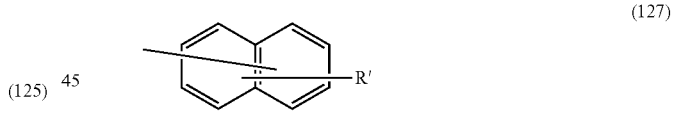
(127)

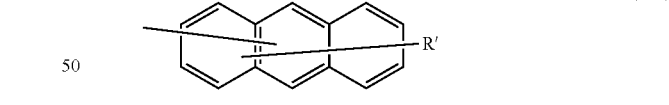
(128)

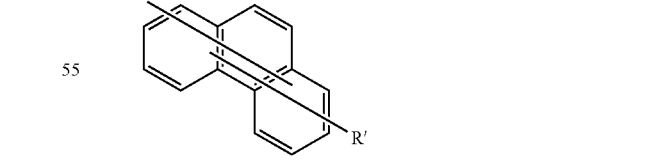
(129)

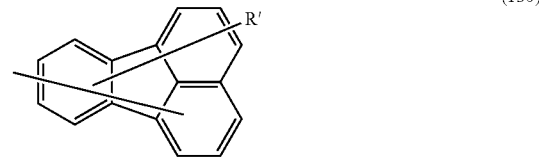
(130)

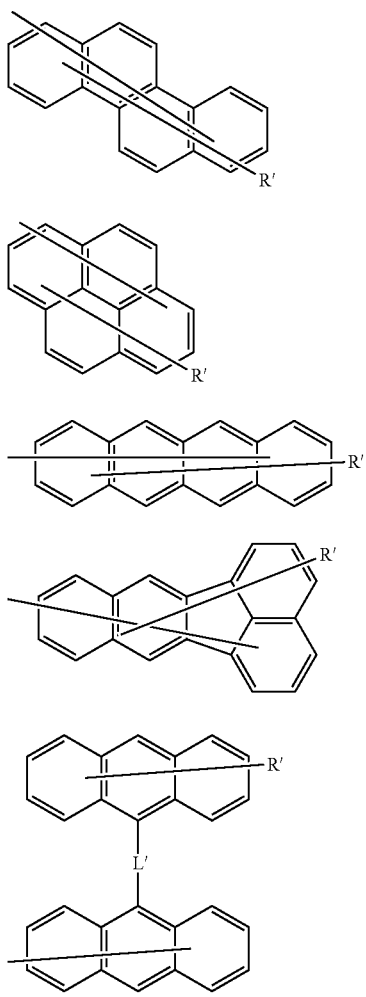

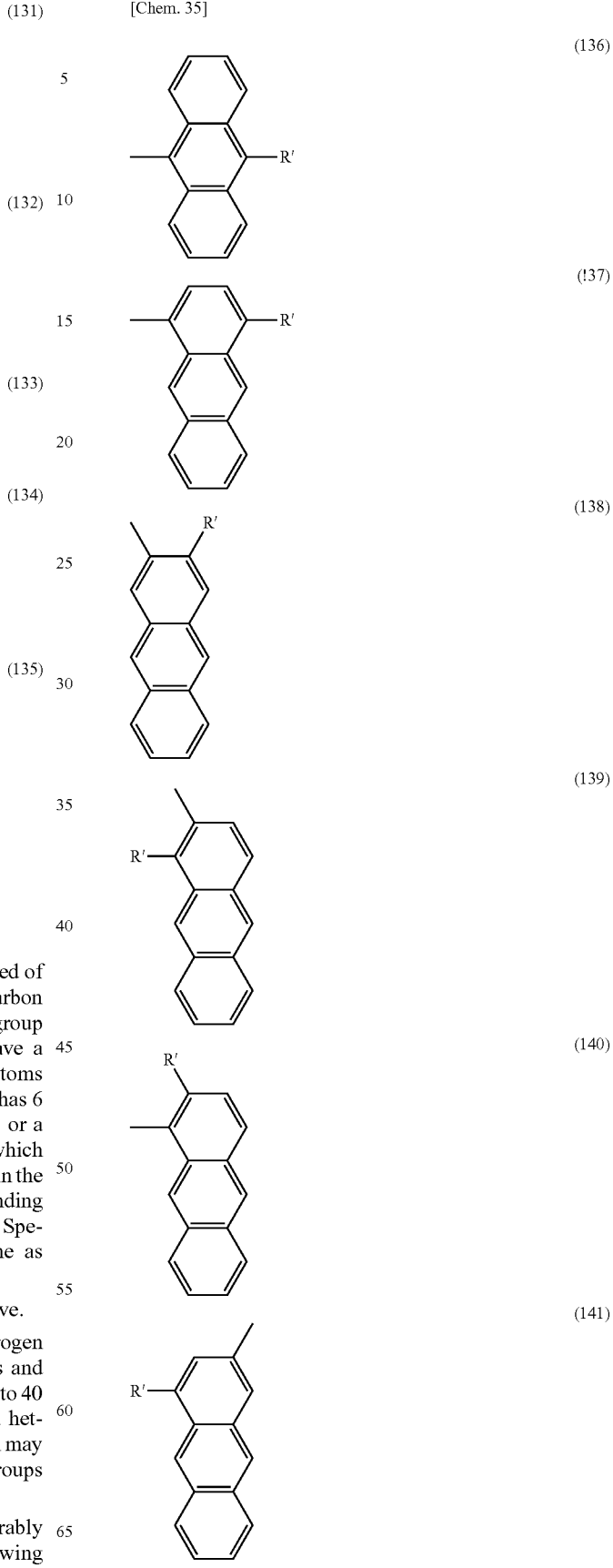

In the formulae (126) to (135), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from each other. Specific examples of each of those groups are the same as described above.

In the formula (135), L' is the same as described above.

In the formulae (126) to (135), R' represents a hydrogen atom, an alkyl group which has 1 to 20 carbon atoms and which may have a substituent, an aryl group which has 6 to 40 carbon atoms and which may have a substituent, or a heteroaryl group which has 3 to 40 carbon atoms and which may have a substituent. Specific examples of each of those groups are the same as described above.

The general formula (128) represented by Arg is preferably a fused ring group represented by any one of the following formulae (136) to (158).

(142) 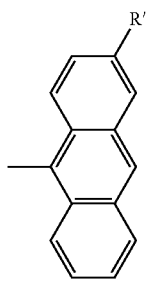
(143) 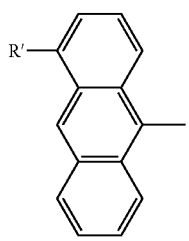
(144) 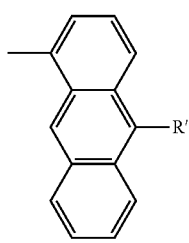
(145) 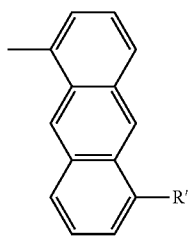
(146) 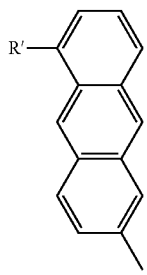
(147) 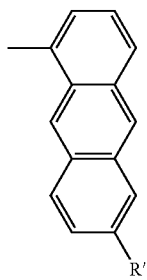
(148) 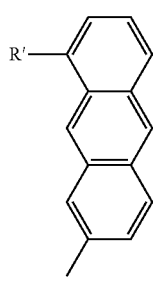
(149) 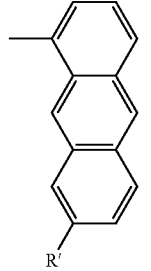
(150) 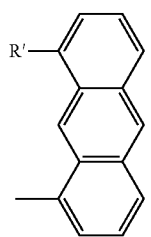
(151) 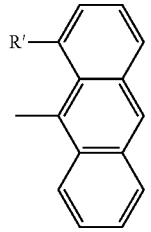
(152) 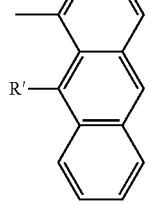
(153) 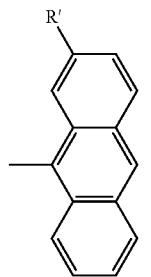

-continued (154)

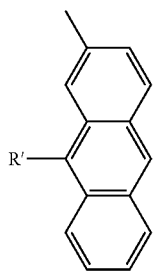

(155)

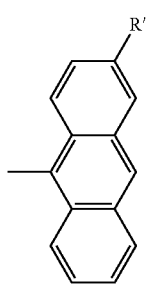

(156)

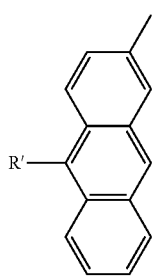

(157)

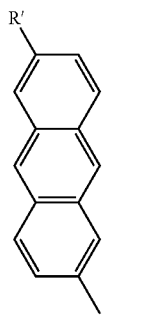

(158)

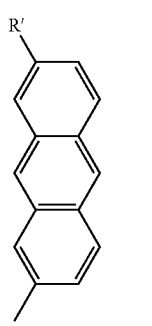

In the formulae (136) to (158), a binding group formed of a halogen atom, an alkyl group which has 1 to 20 carbon atoms and which may have a substituent, an alkoxy group which has 1 to 20 carbon atoms and which may have a substituent, an aryloxy group which has 6 to 40 carbon atoms and which may have a substituent, an aryl group which has 6 to 40 carbon atoms and which may have a substituent, or a heteroaryl group which has 3 to 40 carbon atoms and which may have a substituent may bind to each fused ring, and in the case where a plurality of the binding groups exist, the binding groups may be identical to or different from one another. Specific examples of each of those groups are the same as described above. R' is the same as described above.

Further, it is preferred that $Ar^f$ and $Ar^g$ each independently represent a group selected from the group consisting of the following groups.

[Chem. 36]

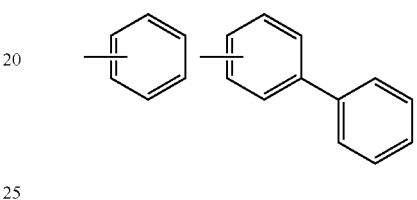

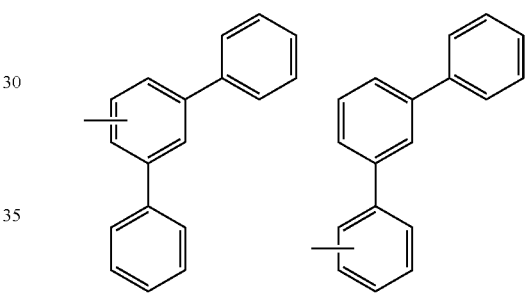

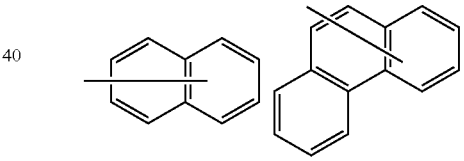

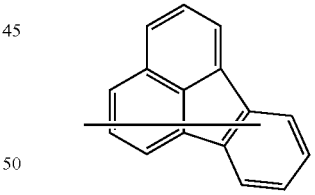

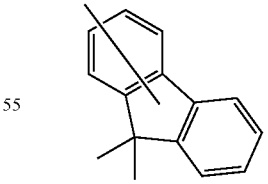

Specific examples of the nitrogen-containing heterocyclic derivatives represented by the formulae (201) to (203) of the present invention are shown below, but the present invention is not limited to these exemplified compounds.

It should be noted that HAr in the following table represents any one of the following parts in the formulae (201) to (203).

[Chem. 37]
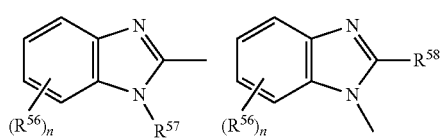 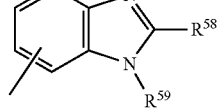
[Chem. 38]
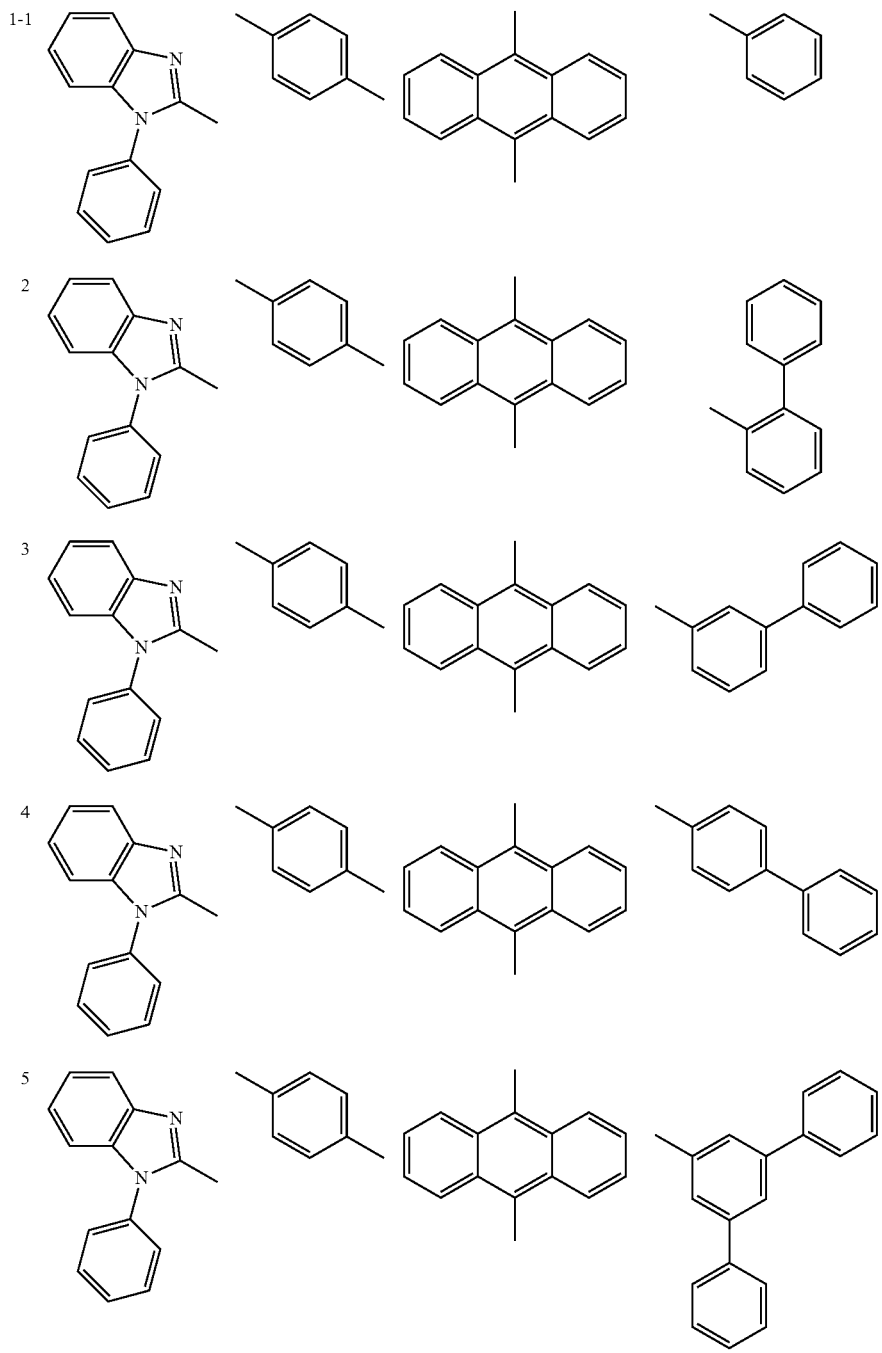

-continued
| | HAr—L⁷—Arᵉ—Ar^f | | | [Chem. 38] |
|---|---|---|---|---|
| | HAr | L⁷ | Arᵉ | Ar^f |
| 6 | 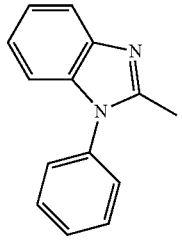 | 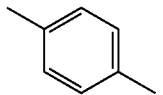 | 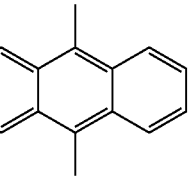 | 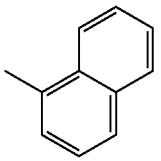 |
| 7 | 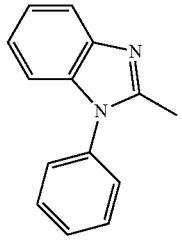 | 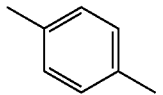 | 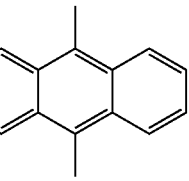 | 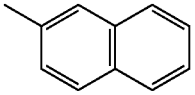 |
| 8 | 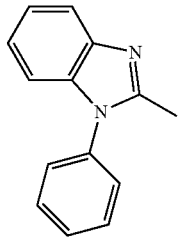 | 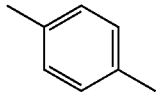 | 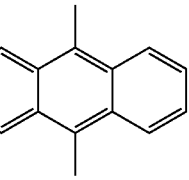 | 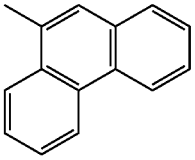 |
| 9 | 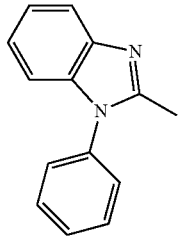 | 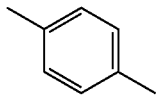 | 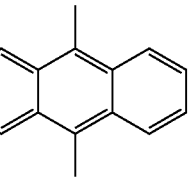 | 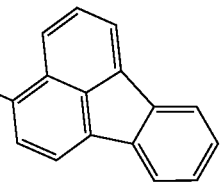 |
| 10 | 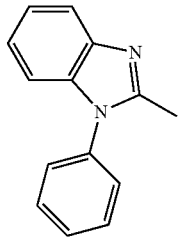 | 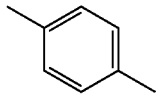 | 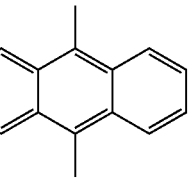 | 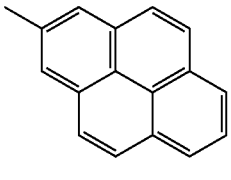 [SMILES: Cc1cc2ccc3cccc4ccc(c1)c2c34] |
| 11 | 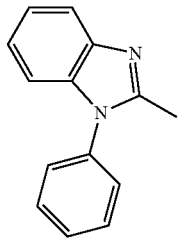 | 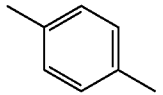 | 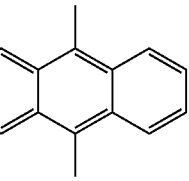 | 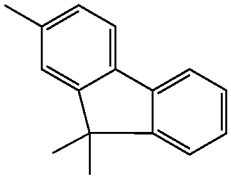 [SMILES: Cc1ccc2c(c1)C(C)(C)c1ccccc1-2] |

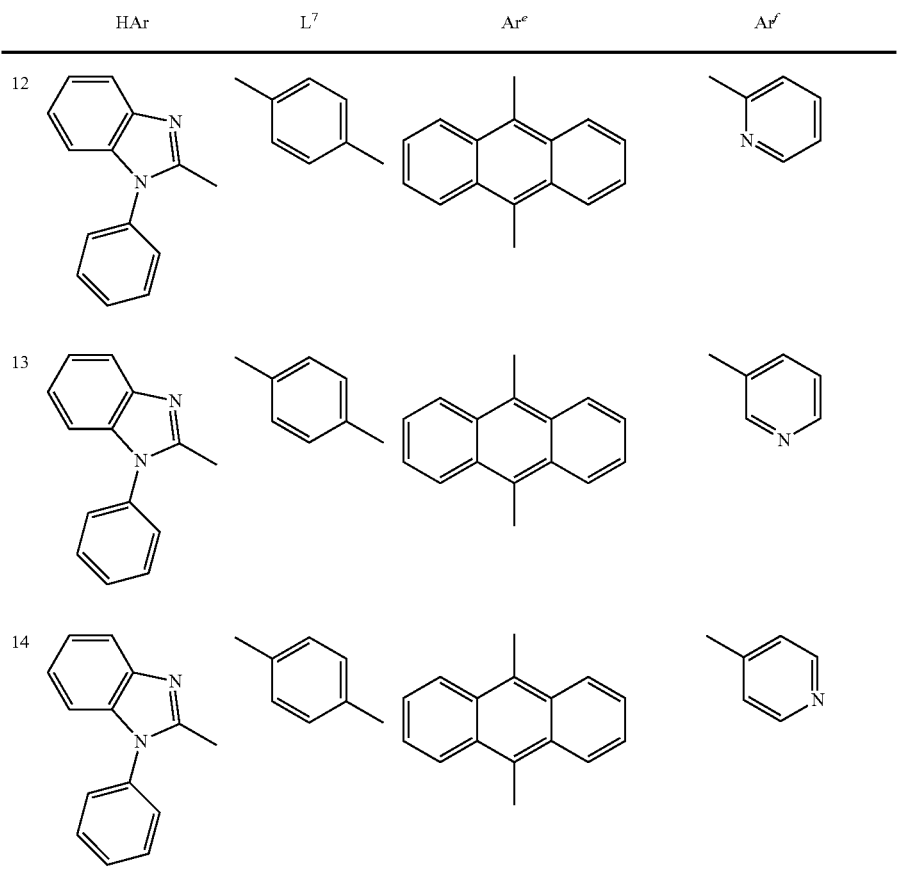
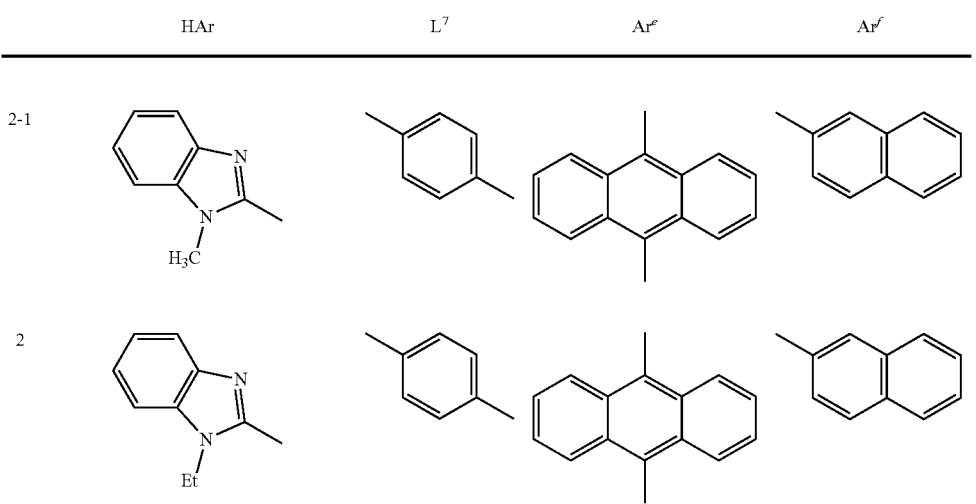

-continued

| | | | [Chem. 39] |
|---|---|---|---|
| | HAr—L⁷—Arᵉ—Ar^f | | |
| HAr | L⁷ | Arᵉ | Ar^f |

(table rows 3–7 contain chemical structures)

[Chem. 39]
HAr—L[7]—Ar[e]—Ar[f]
| | HAr | L[7] | Ar[e] | Ar[f] |
|---|---|---|---|---|
| 8 | | | | |
| 9 | | | | |
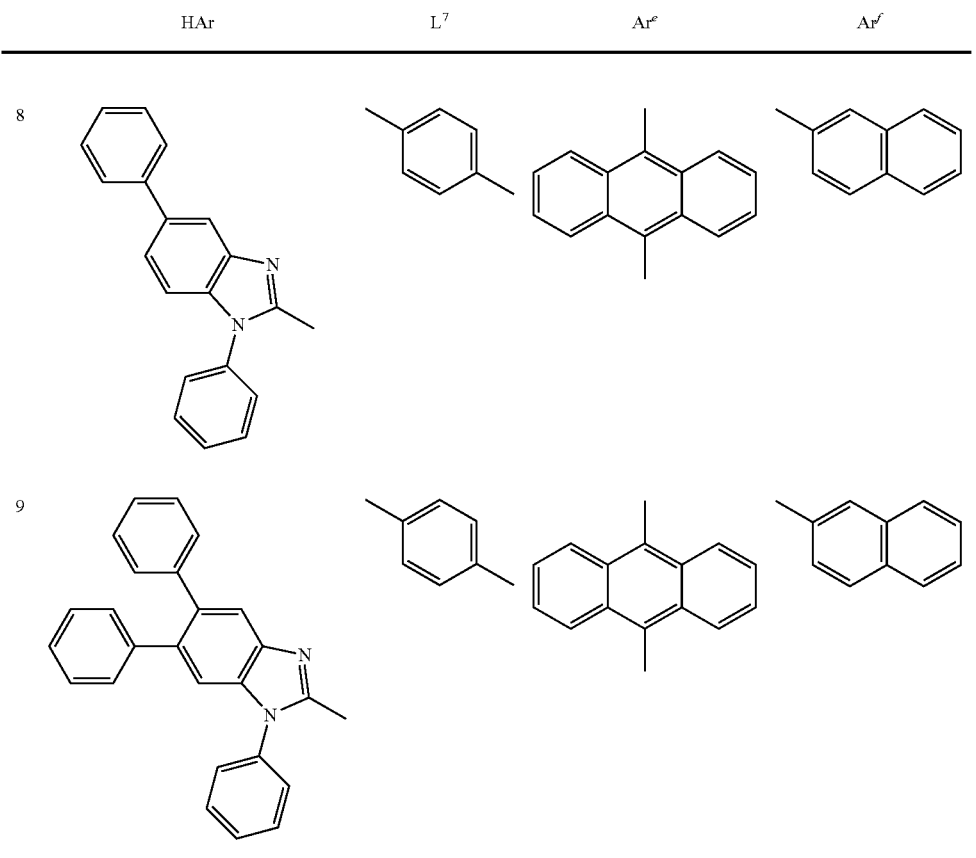
[Chem. 40]
HAr—L[7]—Ar[e]—Ar[f]
| | HAr | L[7] | Ar[e] | Ar[f] |
|---|---|---|---|---|
| 3-1 | | | | |
| 2 | | | | |
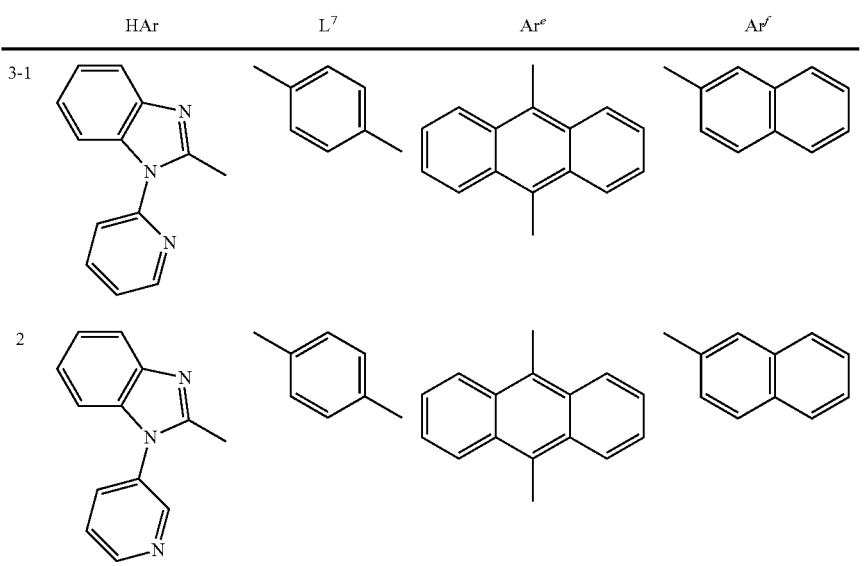

-continued
[Chem. 40]
| | HAr | L[7] | Ar[e] | Ar[f] |
|---|---|---|---|---|
| 3 | 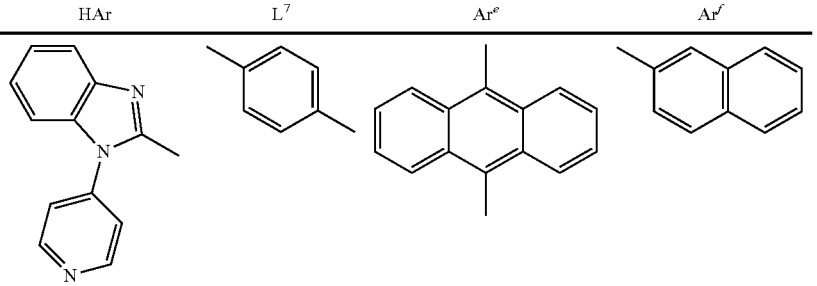 | | | |
| 4 | 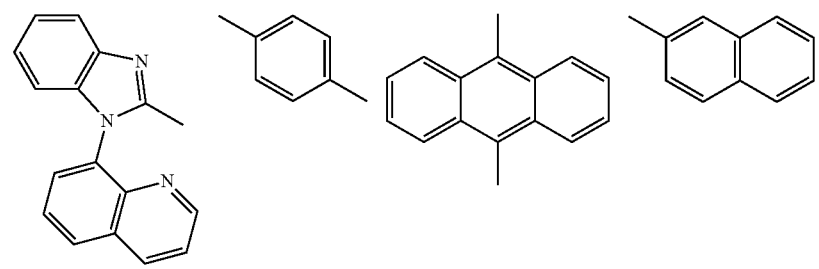 | | | |
| 5 | 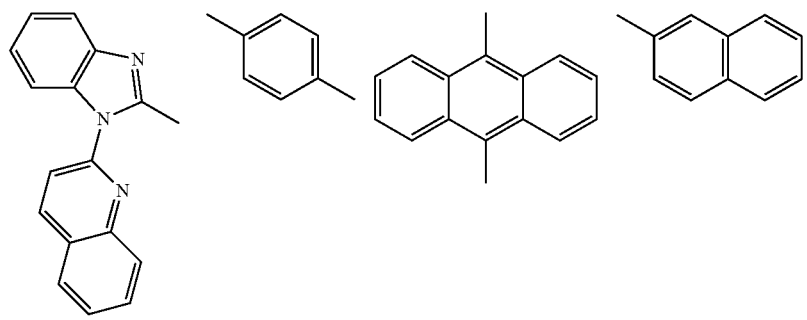 | | | |
| 6 | 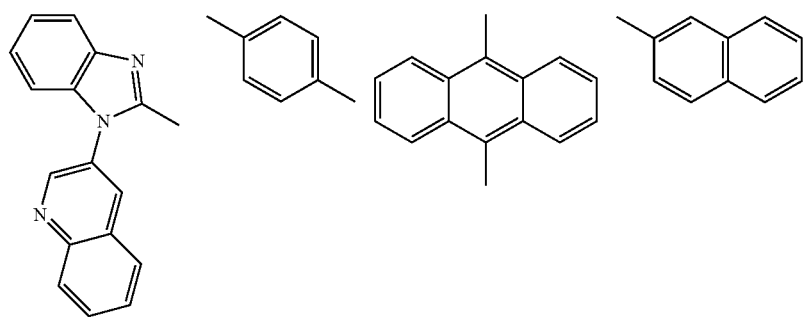 | | | |

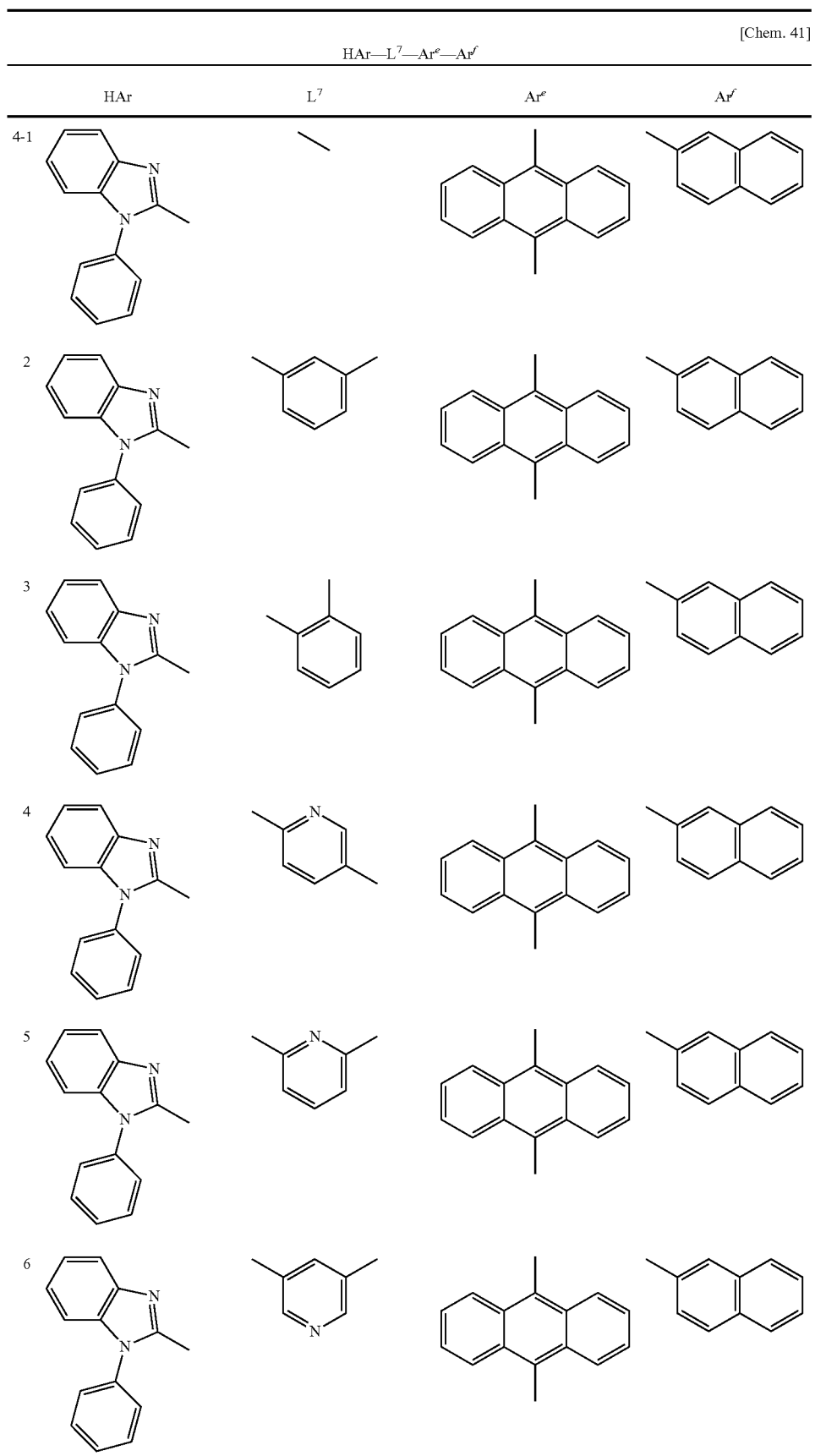

-continued

| | HAr—L⁷—Arᵉ—Arᶠ | | | [Chem. 41] |
|---|---|---|---|---|
| | HAr | L⁷ | Arᵉ | Arᶠ |
| 7 | 1-phenyl-2-methylbenzimidazole | 4,4'-biphenylene | 9,10-anthrylene | 2-naphthyl |
| 8 | 1-phenyl-2-methylbenzimidazole | 3,4'-biphenylene | 9,10-anthrylene | 2-naphthyl |
| 9 | 1-phenyl-2-methylbenzimidazole | 3,3'-biphenylene | 9,10-anthrylene | 2-naphthyl |
| 10 | 1-phenyl-2-methylbenzimidazole | 1,5-naphthylene | 9,10-anthrylene | 2-naphthyl |
| 11 | 1-phenyl-2-methylbenzimidazole | 2,6-naphthylene | 9,10-anthrylene | 2-naphthyl |
| 12 | 1-phenyl-2-methylbenzimidazole | 9,10-anthrylene | 9,10-anthrylene | 2-naphthyl |

[Chem. 42]
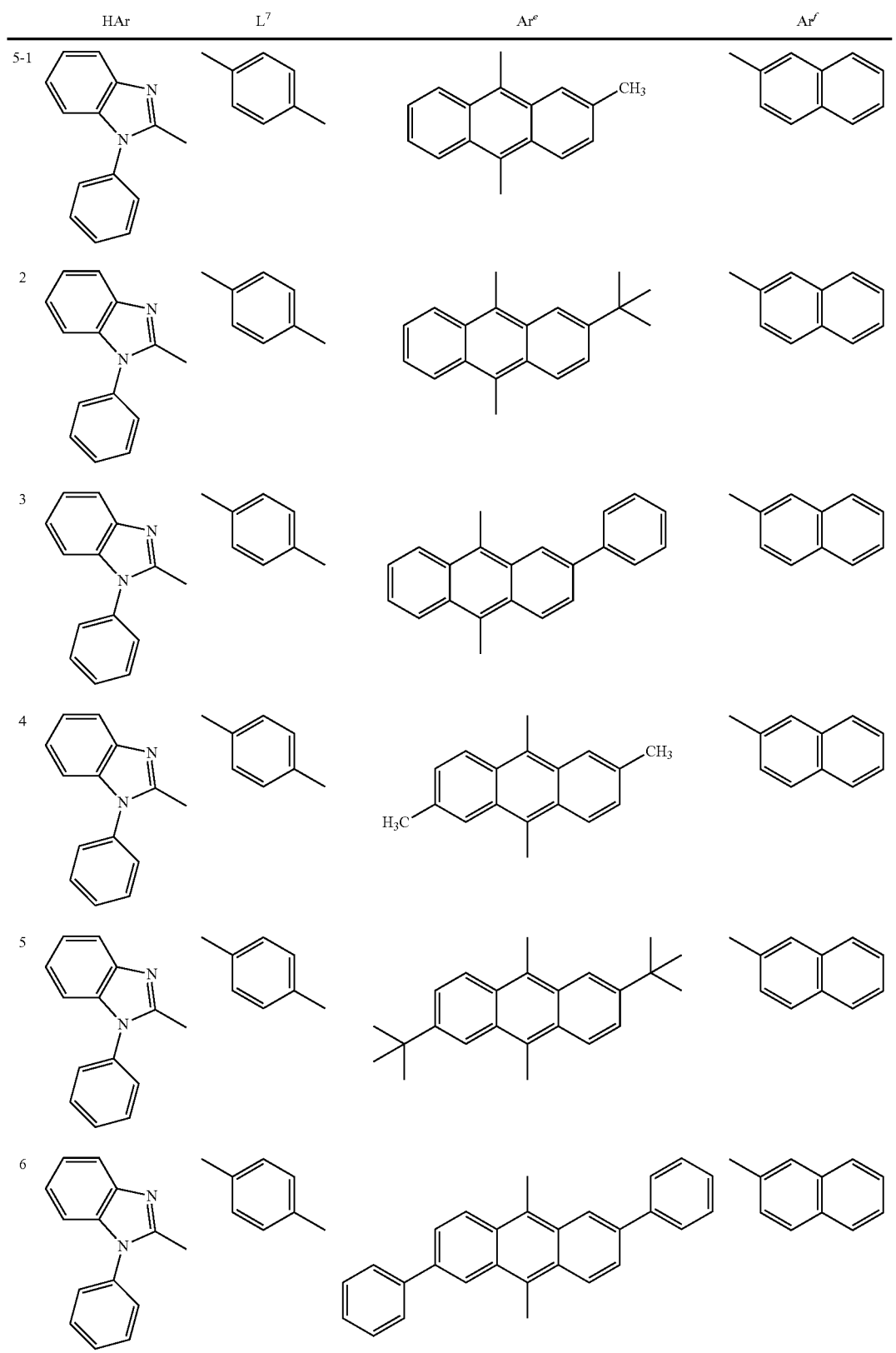

[Chem. 43]

HAr—L⁷—Arᵉ—Arᶠ

| | HAr | L⁷ | Arᵉ | Arᶠ |
|---|---|---|---|---|
| 6-1 | | | | |
| 2 | | | | |
| 3 | | | | |
| 4 | | | | |
| 5 | | | | |

[Chem. 44]
HAr—L⁷—Arᵉ—Ar^f
| | HAr | L⁷ | Arᵉ | Ar^f |
|---|---|---|---|---|
| 7-1 | 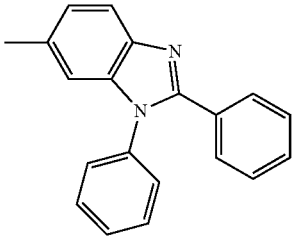 | 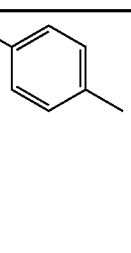 | 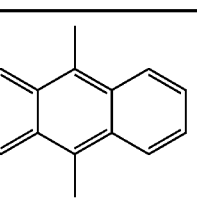 | 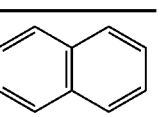 |
| 2 | 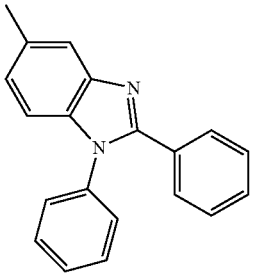 | 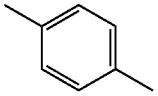 | 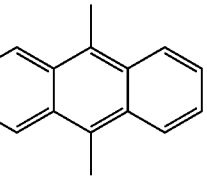 | 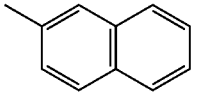 |
| 3 | 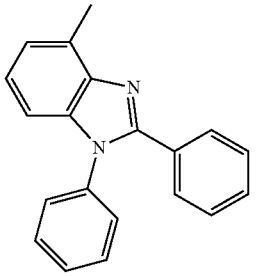 | 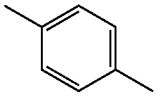 | 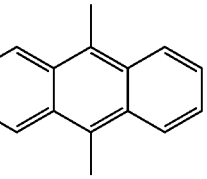 | 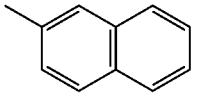 |
| 4 | 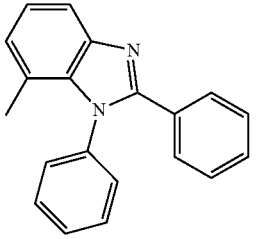 | 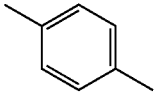 | 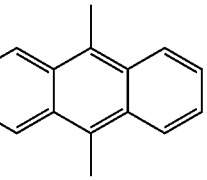 | 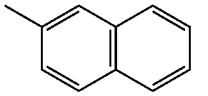 |
| 5 | 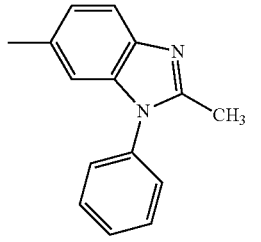 | 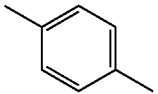 | 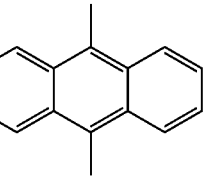 | 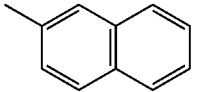 |
| 6 | 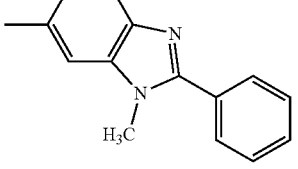 | 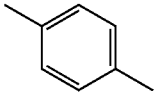 | 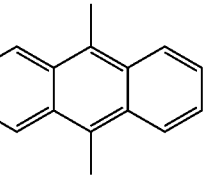 | 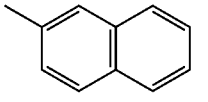 |

-continued
[Chem. 44]
HAr—L⁷—Arᵉ—Ar^f
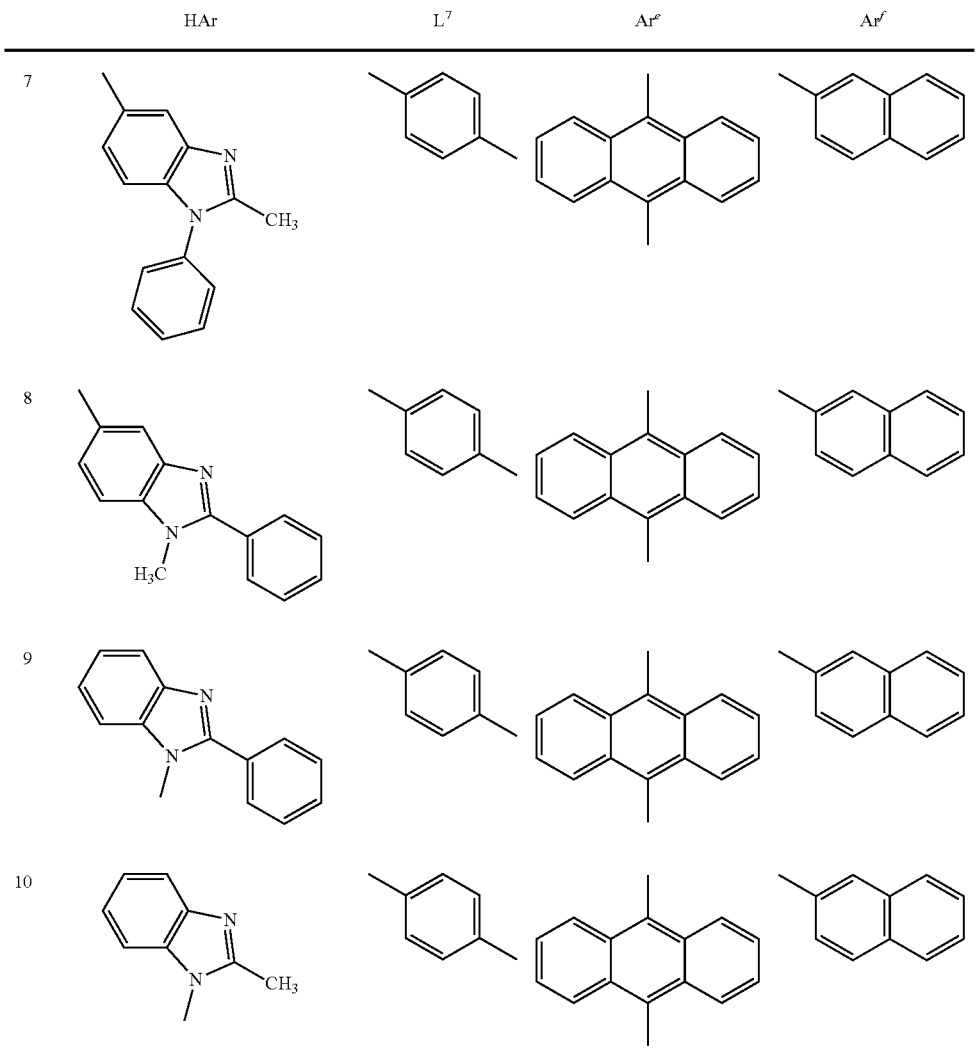
[Chem. 45]
HAr—L⁷—Arᵉ—Ar^f
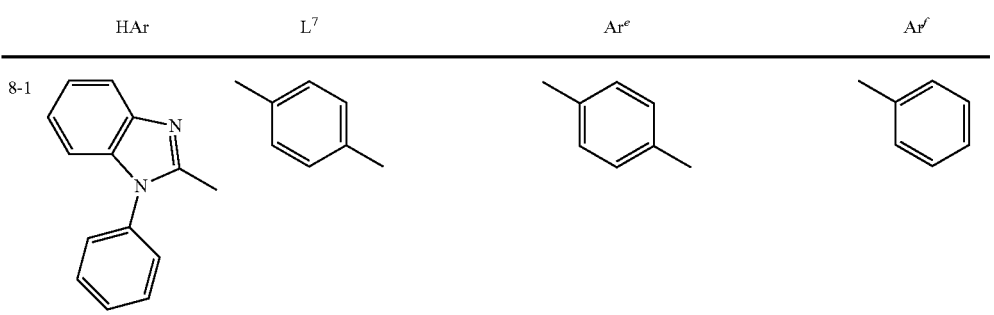

-continued

| | HAr—L⁷—Arᵉ—Arᶠ | | | [Chem. 45] |
|---|---|---|---|---|
| | HAr | L⁷ | Arᵉ | Arᶠ |
| 2 | 2-methyl-1-phenyl-benzimidazole | 1,4-phenylene | 1,3-phenylene | phenyl |
| 3 | 2-methyl-1-phenyl-benzimidazole | 1,4-phenylene | naphthalene-1,6-diyl | phenyl |
| 4 | 2-methyl-1-phenyl-benzimidazole | 1,4-phenylene | naphthalene-2,6-diyl | phenyl |
| 5 | 2-methyl-1-phenyl-benzimidazole | 1,4-phenylene | phenanthrene-9,10-diyl | phenyl |
| 6 | 2-methyl-1-phenyl-benzimidazole | 1,4-phenylene | phenanthrene-2,7-diyl | phenyl |
| 7 | 2-methyl-1-phenyl-benzimidazole | 1,4-phenylene | phenanthren-9-yl | H |

| HAr | L⁷ | Arᵉ | Arᶠ |
|---|---|---|---|
| 8 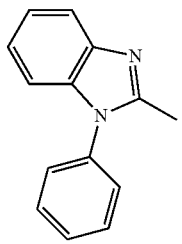 | 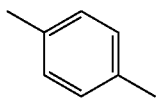 | 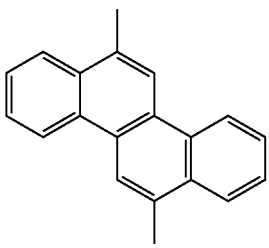 | 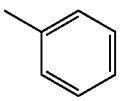 |
| 9 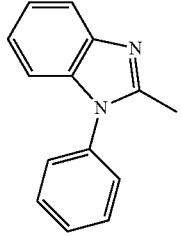 | 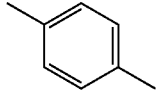 | 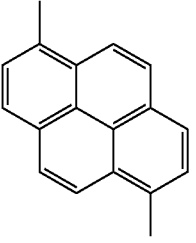 | 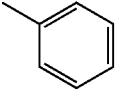 |
| 10 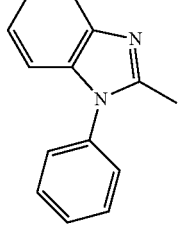 | 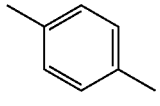 | 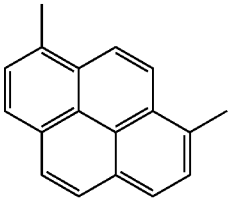 | 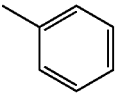 |
| 11 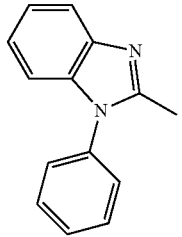 | 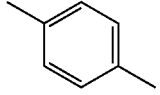 | 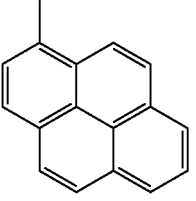 | —H |
| 12 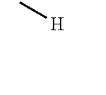 | 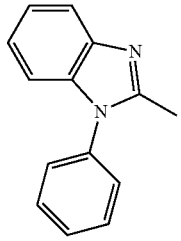 | 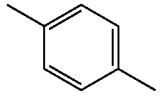 | 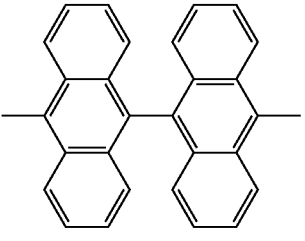 |
| 13 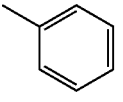 | 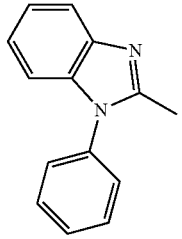 | 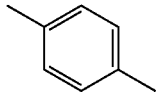 | 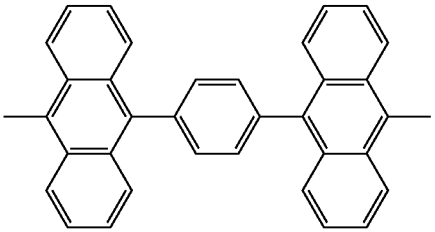 |

[Chem. 46]
HAr—L⁷—Arᵉ—Arᶠ
| | HAr | L⁷ | Arᵉ | Arᶠ |
|---|---|---|---|---|
| 9-1 | 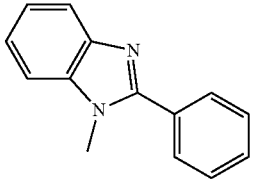 | 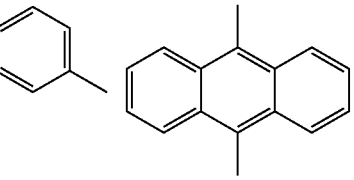 | 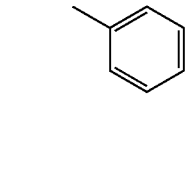 |  |
| 2 | 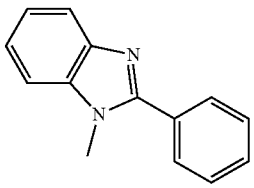 | 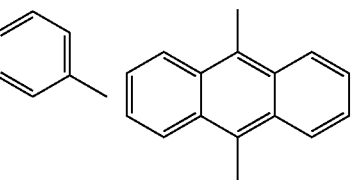 | 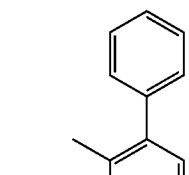 |  |
| 3 | 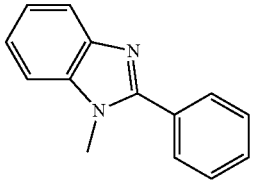 | 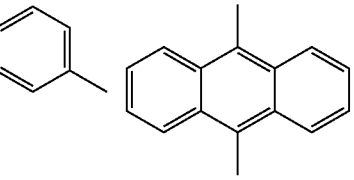 | 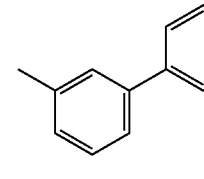 |  |
| 4 | 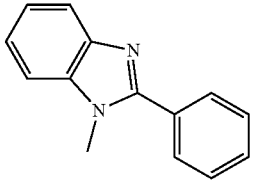 | 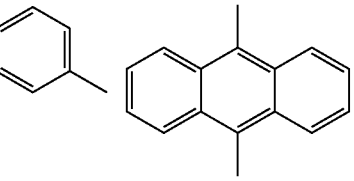 | 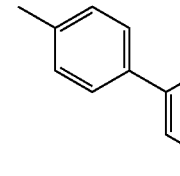 |  |
| 5 | 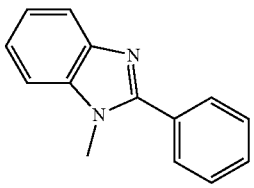 | 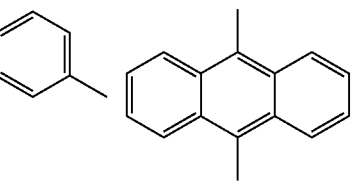 | 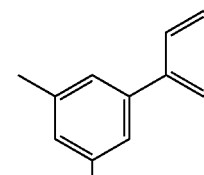 |  |
| 6 | 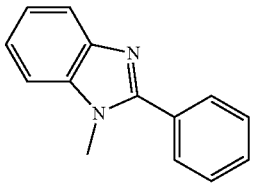 | 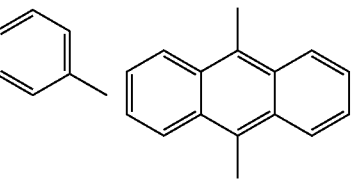 | 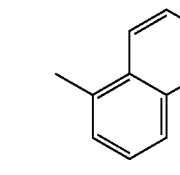 |  |
| 7 | 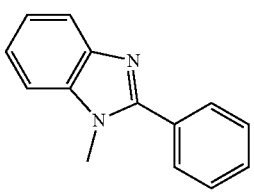 | 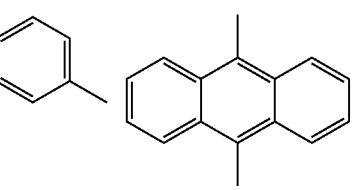 | 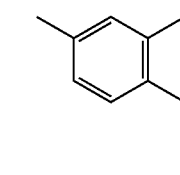 |  |

-continued
|   | HAr | L⁷ | Arᵉ | Arᶠ |
|---|---|---|---|---|
| 8 | 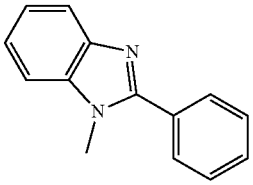 | 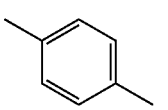 | 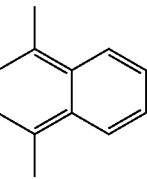 | 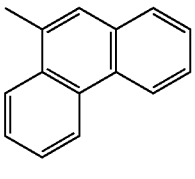 |
| 9 | 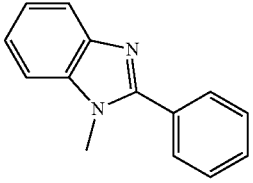 | 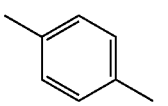 | 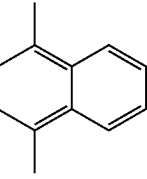 | 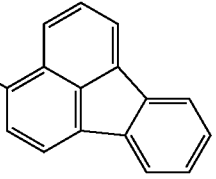 |
| 10 | 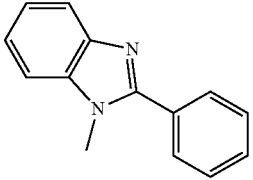 | 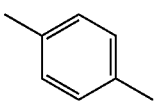 | 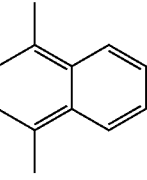 | 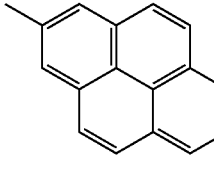 |
| 11 | 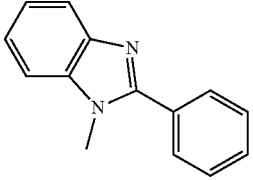 | 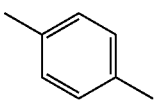 | 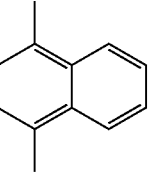 | 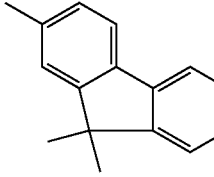 |
| 12 | 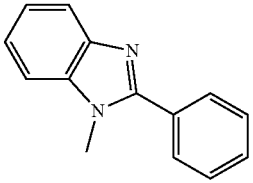 | 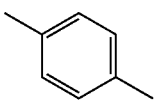 | 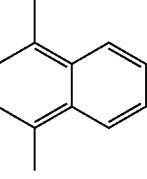 | 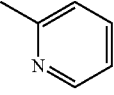 |
| 13 | 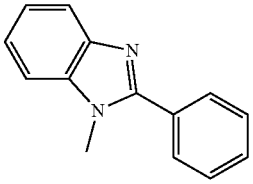 | 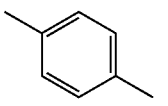 | 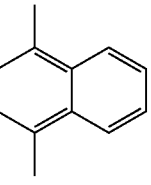 | 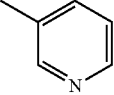 |
| 14 | 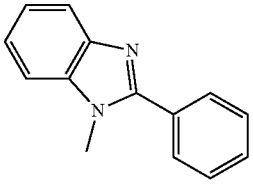 | 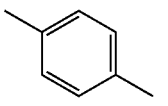 | 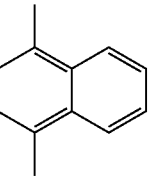 | 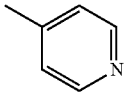 |

| | HAr | L⁷ | Arᵉ | Arᶠ |
|---|---|---|---|---|
| 10-1 | | | | |
| 2 | | | | |
| 3 | | | | |
| 4 | | | | |
| 5 | | | | |
| 6 | | | | |
| 7 | | | | |

HAr—L⁷—Arᵉ—Arᶠ [Chem. 47]

[Chem. 47]
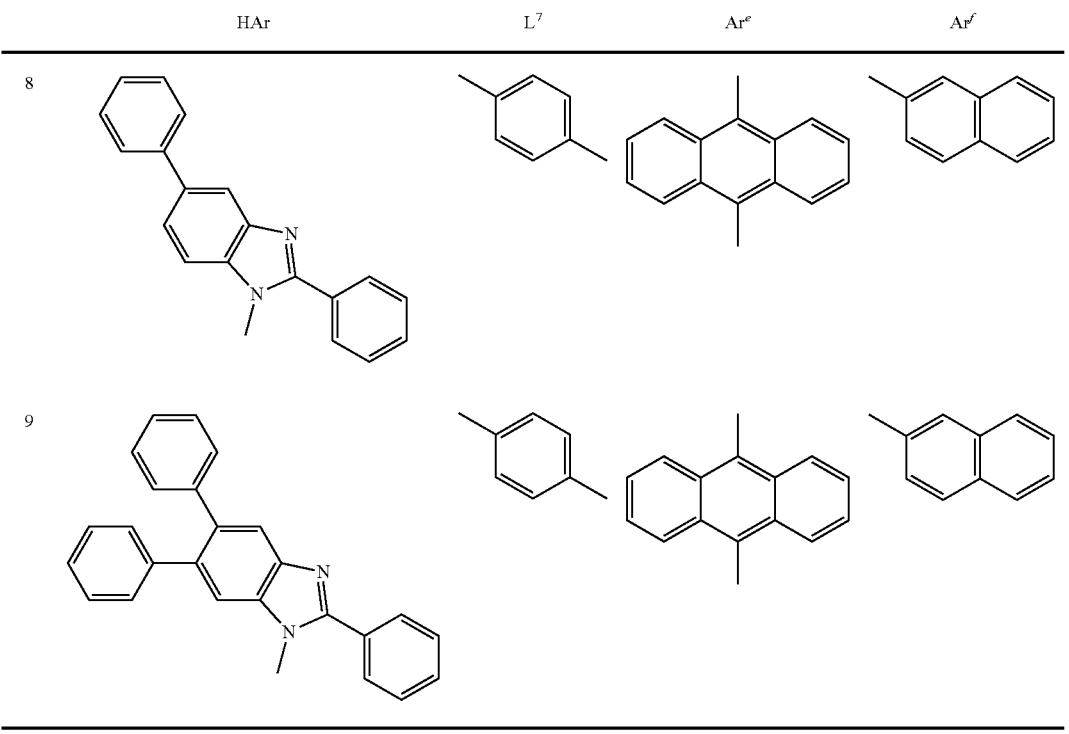
[Chem. 48]
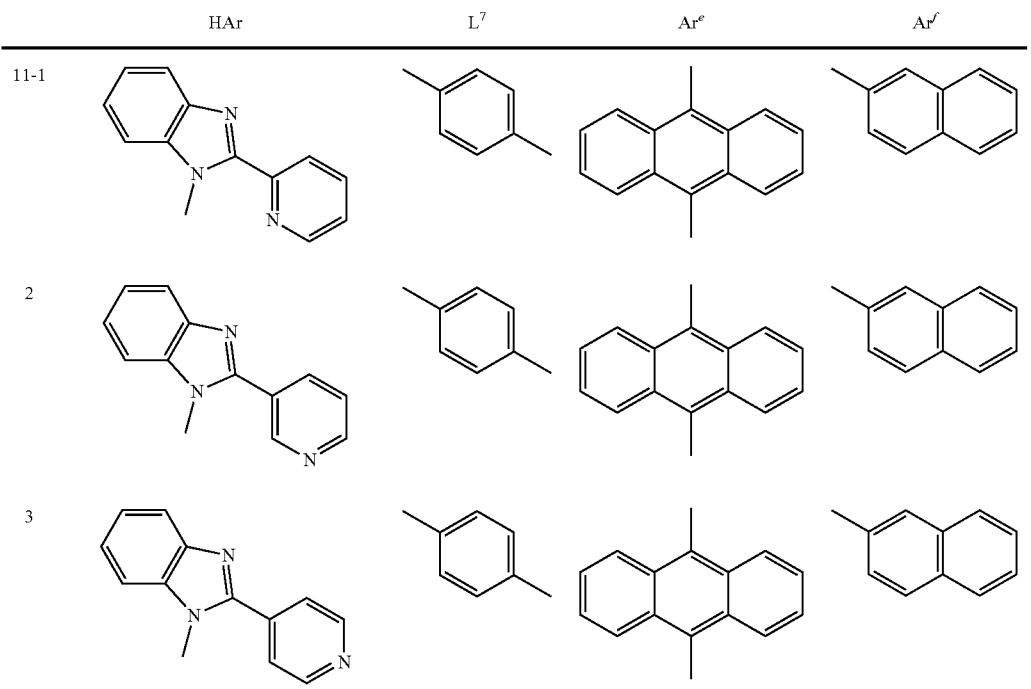

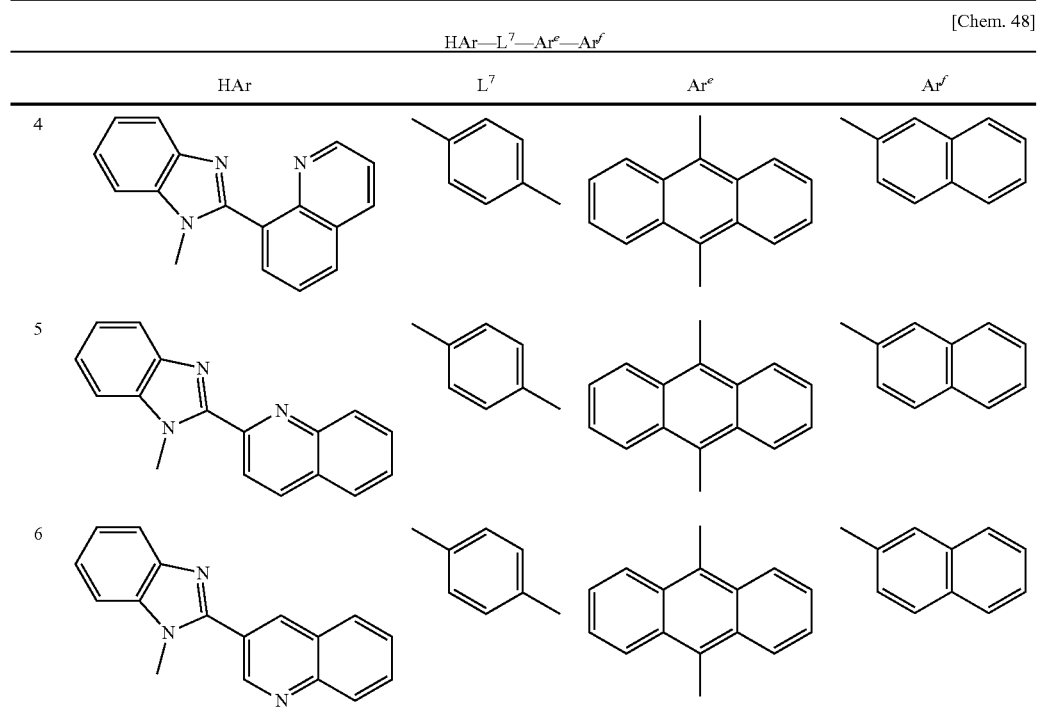
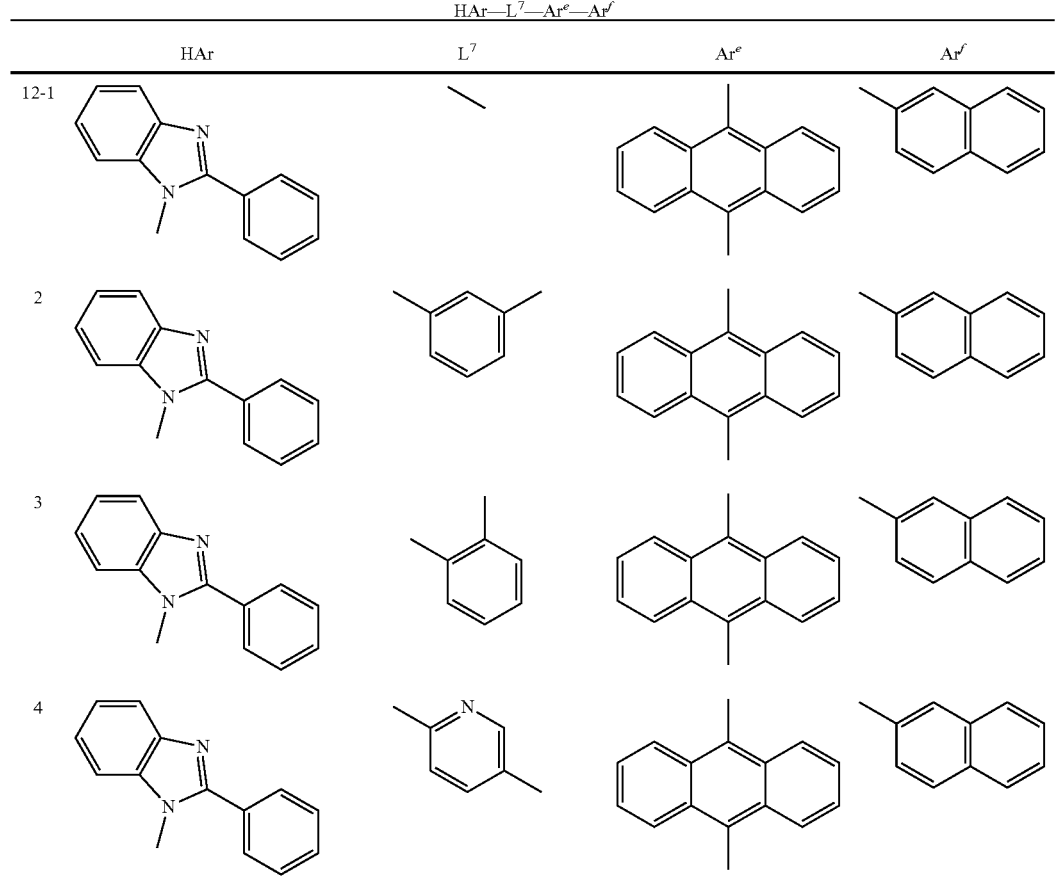

-continued

HAr—L⁷—Arᵉ—Ar^f  [Chem. 49]

| | HAr | L⁷ | Arᵉ | Ar^f |
|---|---|---|---|---|
| 5 | 1-methyl-2-phenylbenzimidazole | 2,6-pyridinediyl | 9,10-dimethylanthracene-diyl | 2-methylnaphthalene |
| 6 | 1-methyl-2-phenylbenzimidazole | 4,4'-dimethylbiphenyl | 9,10-dimethylanthracene-diyl | 2-methylnaphthalene |
| 7 | 1-methyl-2-phenylbenzimidazole | 3,4'-dimethylbiphenyl | 9,10-dimethylanthracene-diyl | 2-methylnaphthalene |
| 8 | 1-methyl-2-phenylbenzimidazole | 3,3'-dimethylbiphenyl | 9,10-dimethylanthracene-diyl | 2-methylnaphthalene |
| 9 | 1-methyl-2-phenylbenzimidazole | 1,5-dimethylnaphthalene | 9,10-dimethylanthracene-diyl | 2-methylnaphthalene |
| 10 | 1-methyl-2-phenylbenzimidazole | 2,6-dimethylnaphthalene | 9,10-dimethylanthracene-diyl | 2-methylnaphthalene |
| 11 | 1-methyl-2-phenylbenzimidazole | 9,10-dimethylanthracene | 9,10-dimethylanthracene-diyl | 2-methylnaphthalene |

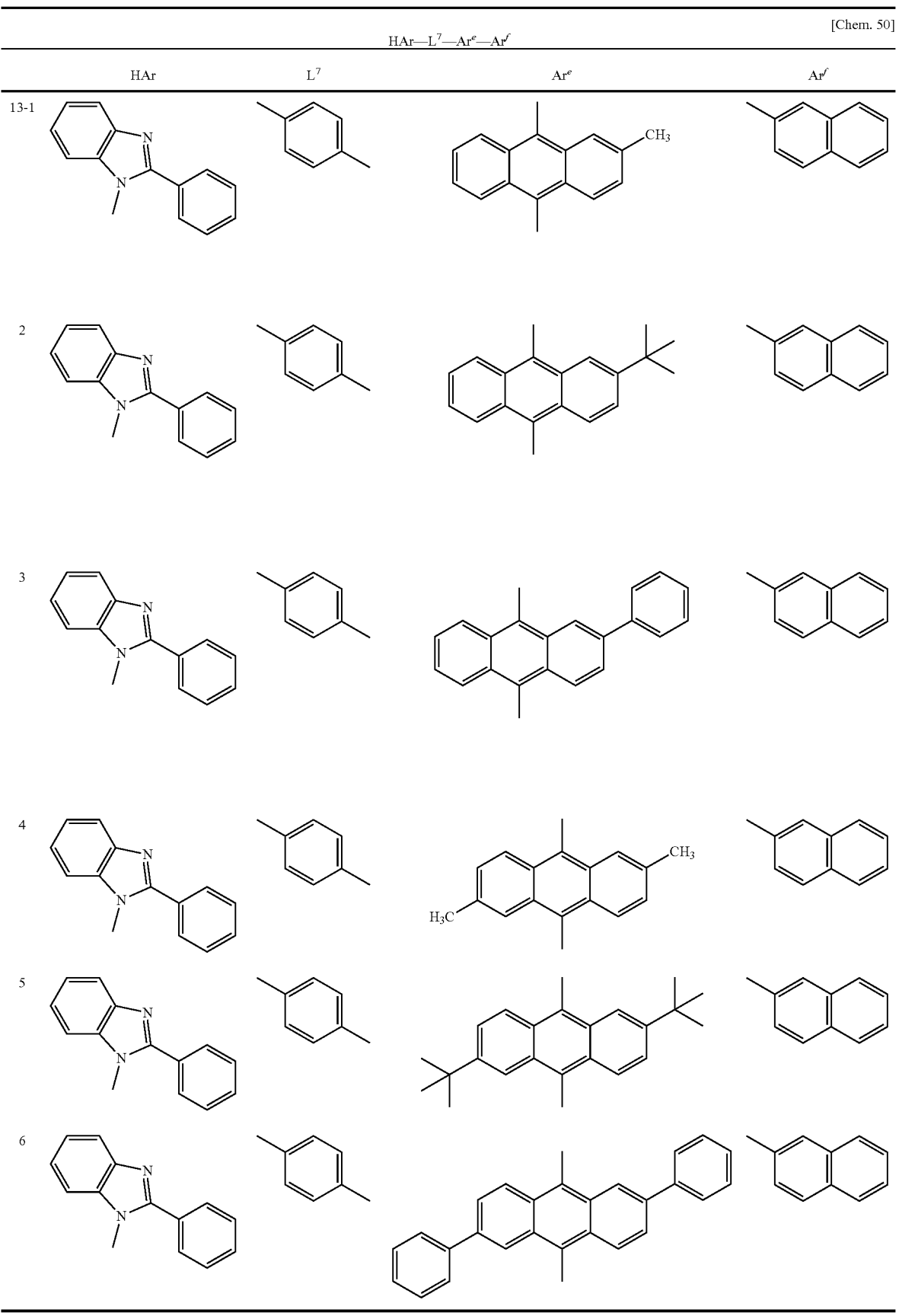

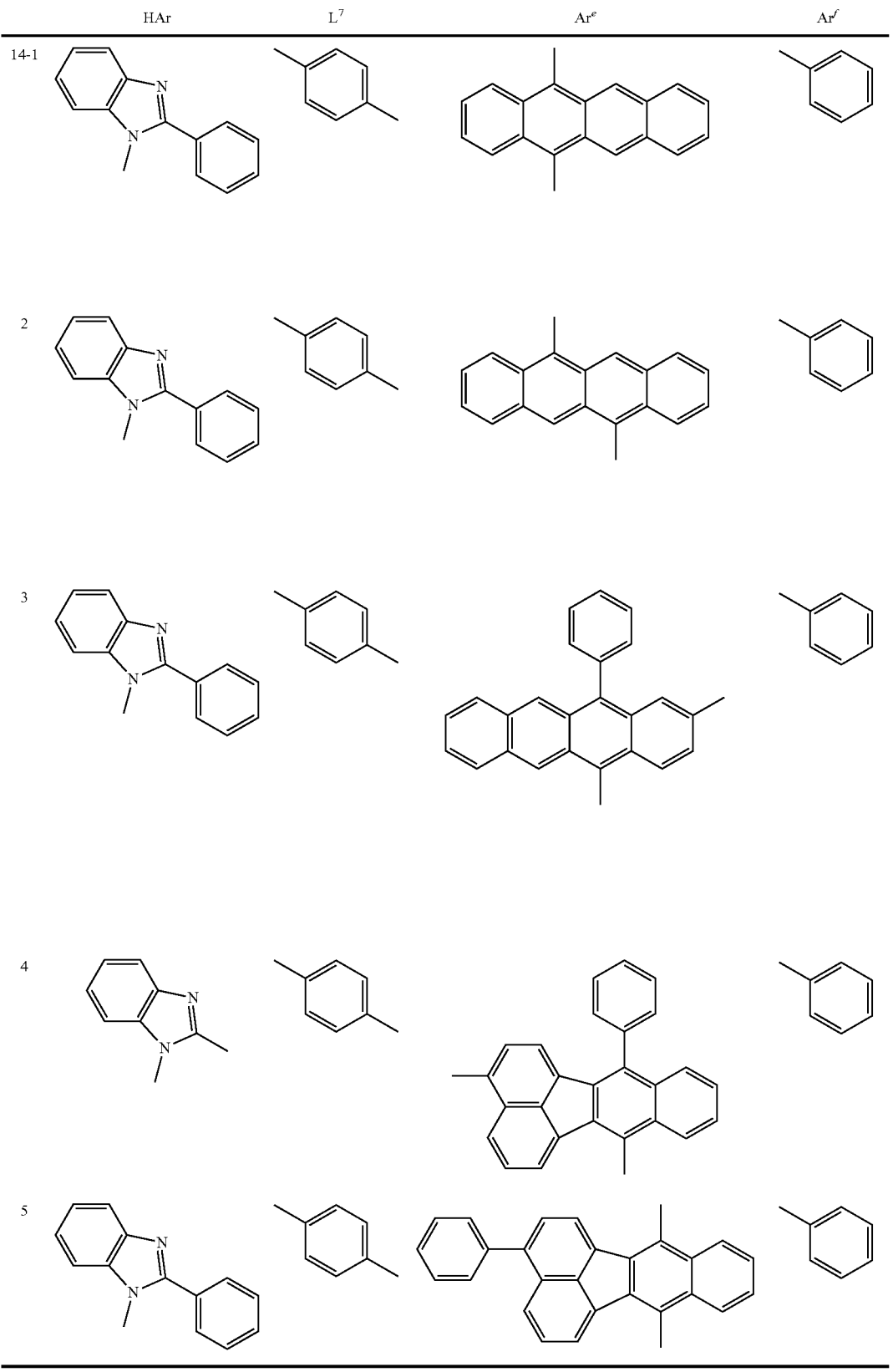

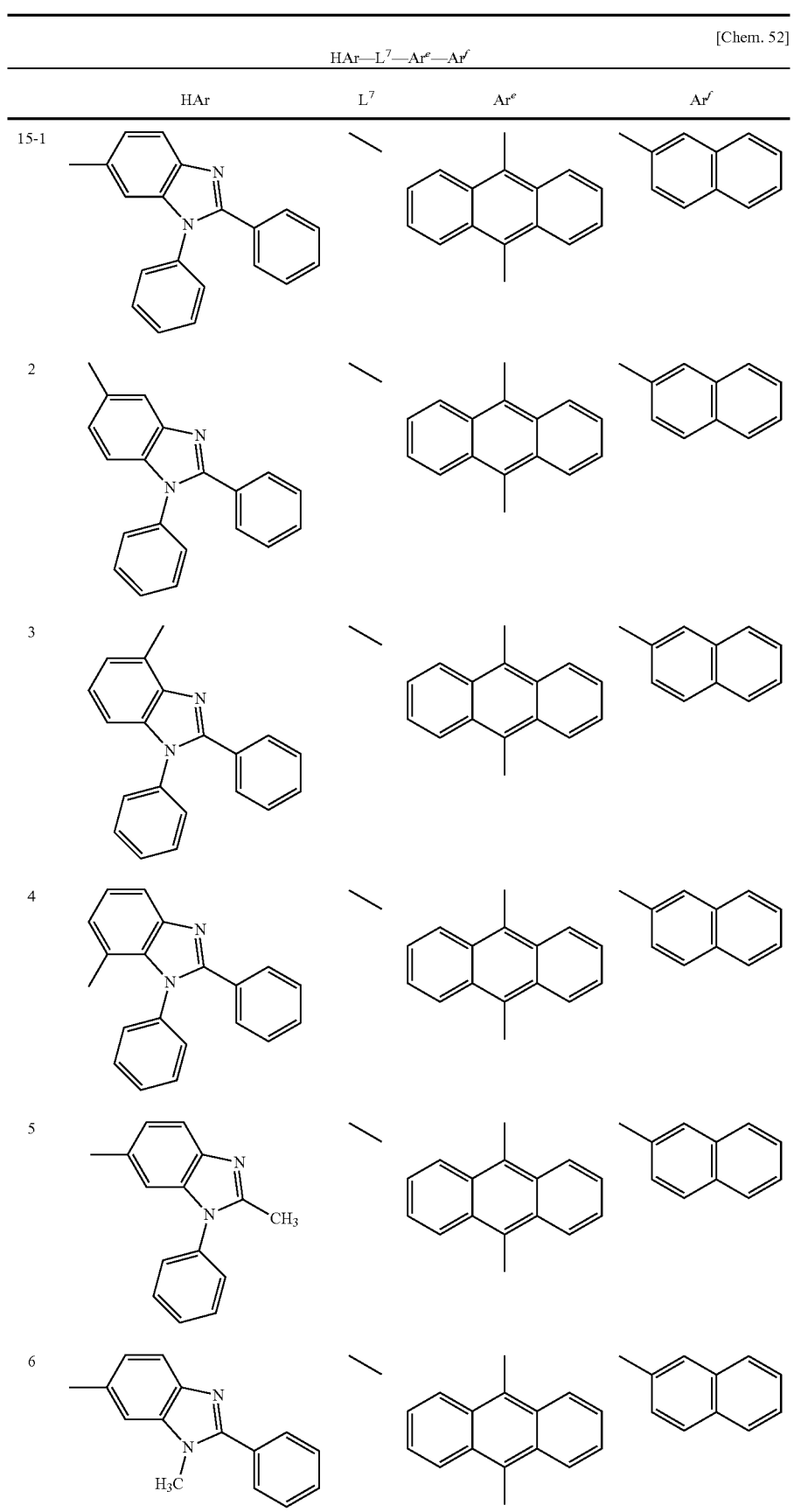

-continued
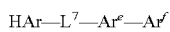
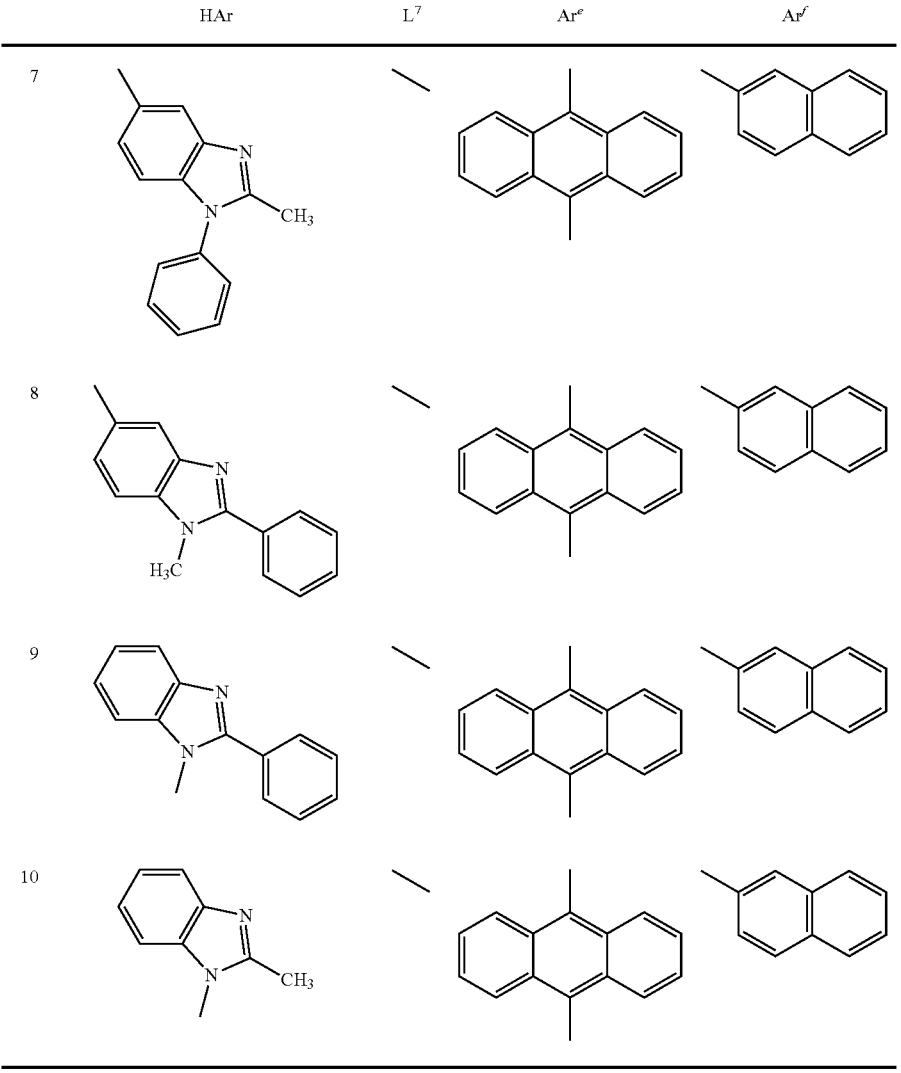
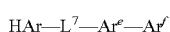
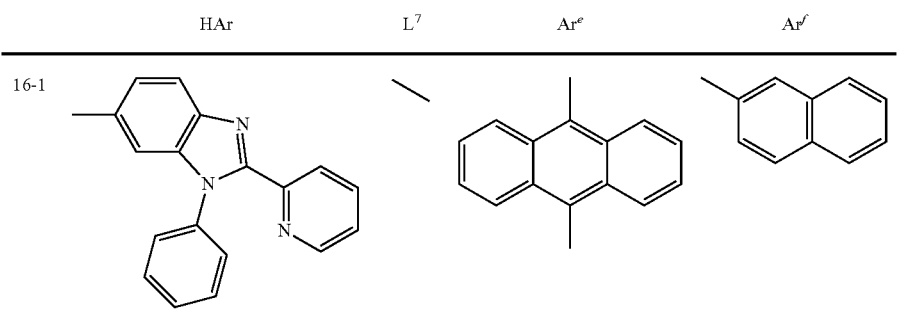

-continued
| HAr—L⁷—Arᵉ—Arᶠ | | | | [Chem. 53] |
|---|---|---|---|---|
| HAr | L⁷ | Arᵉ | Arᶠ | |
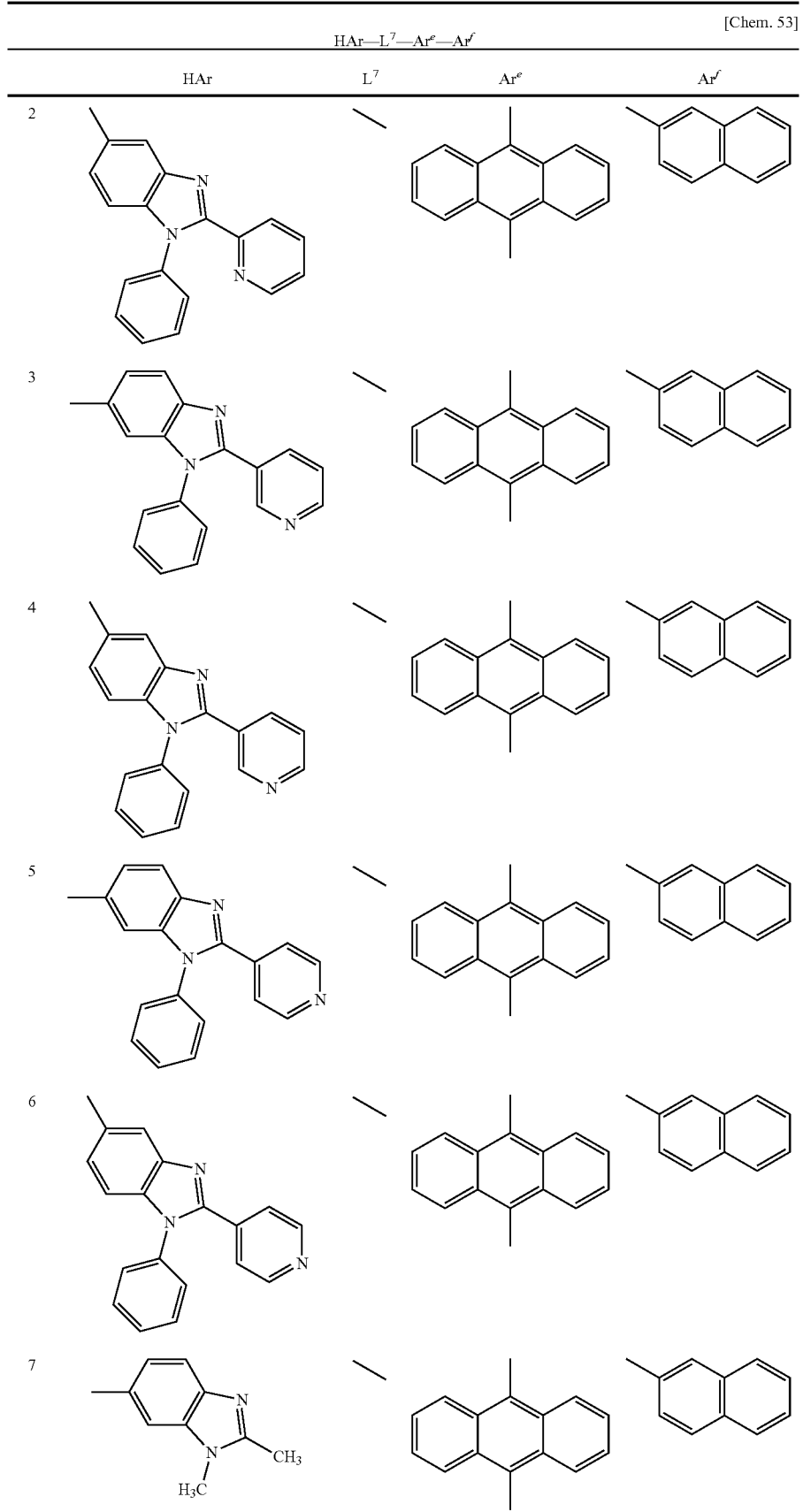

-continued
| | | | [Chem. 53] |
|---|---|---|---|
| HAr | L⁷ | Arᵉ | Ar^f |
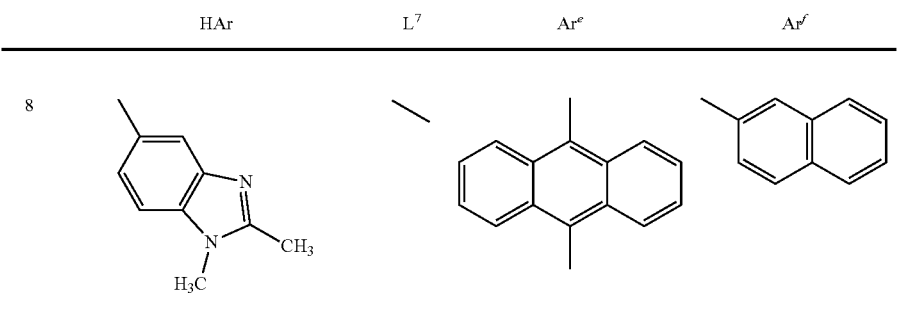
| | | | [Chem. 54] |
|---|---|---|---|
| HAr | L⁷ | Arᵉ | Ar^f |
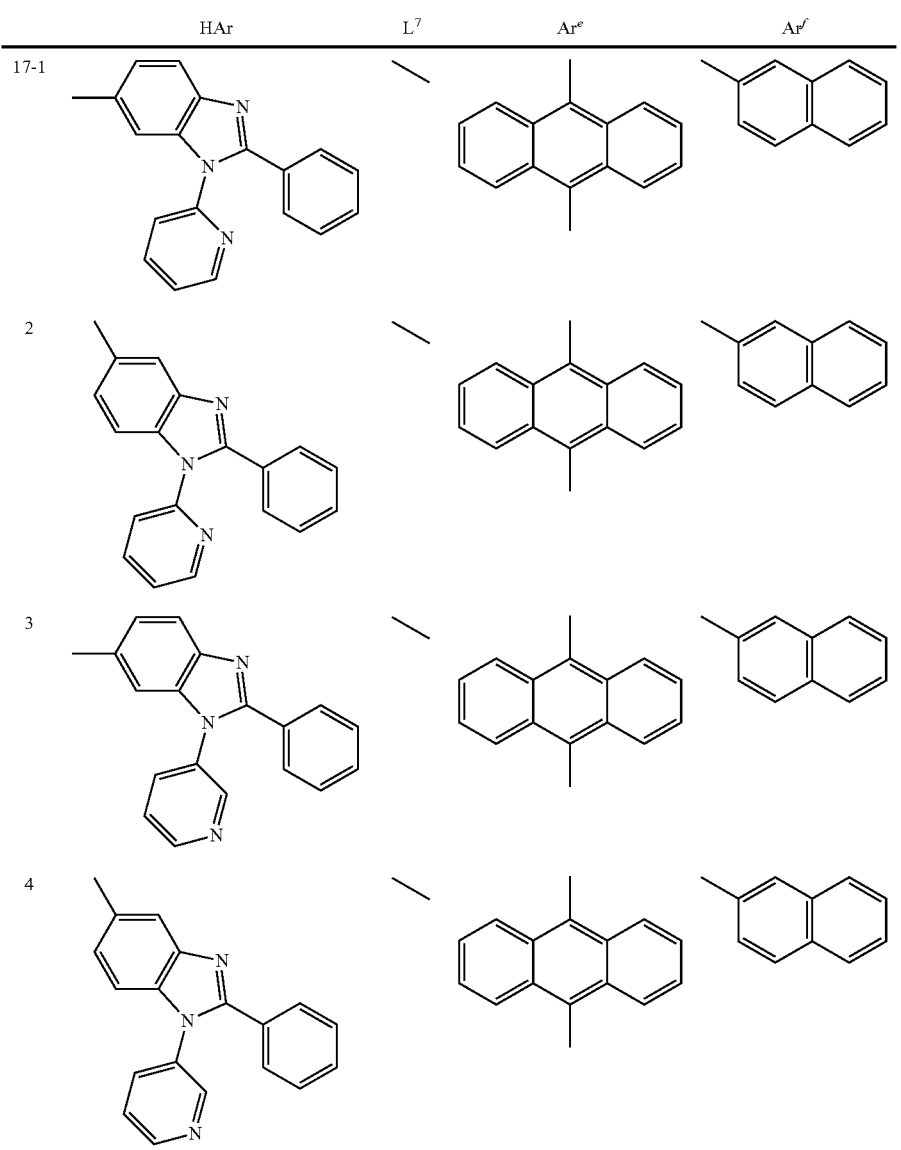

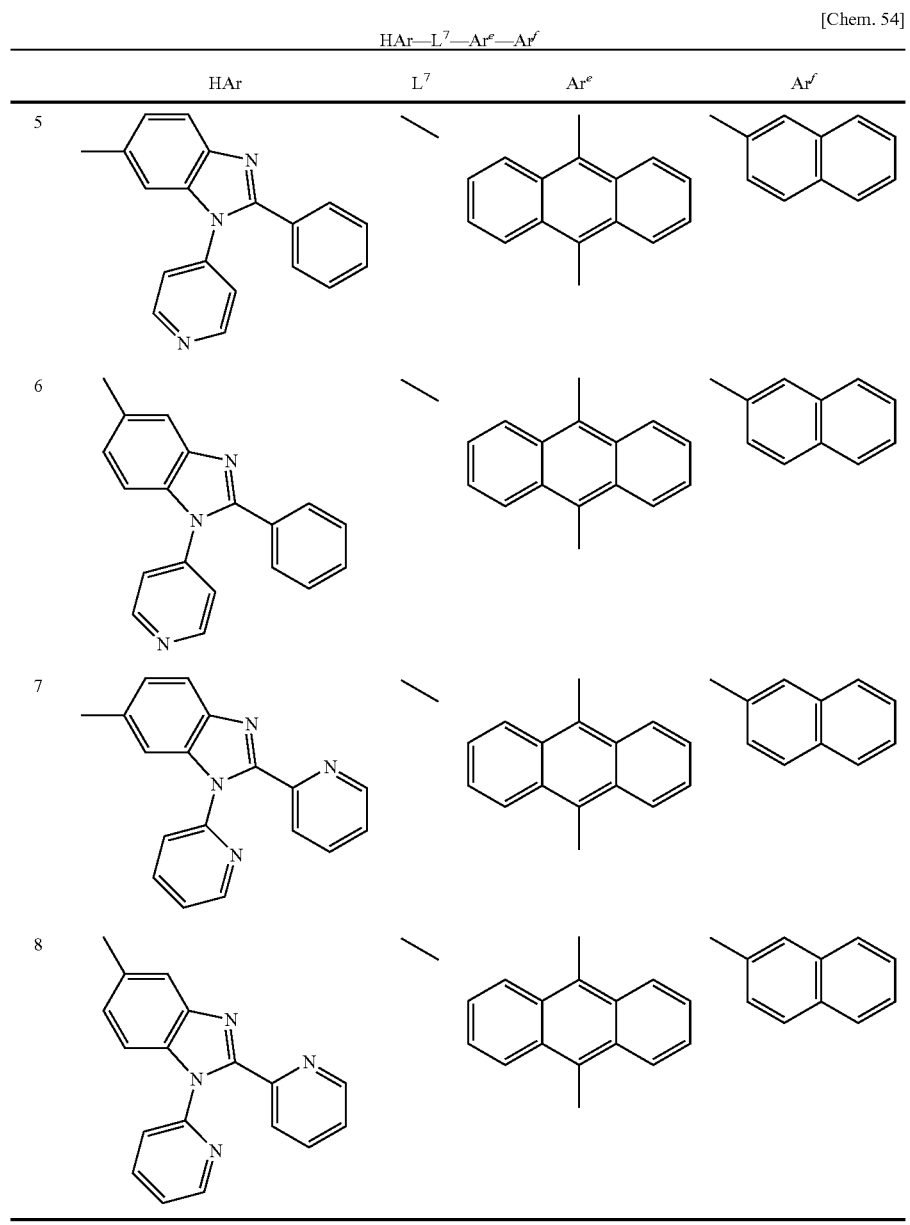

Of those specific examples, (1-1), (1-5), (1-7), (2-1), (3-1), (4-2), (4-6), (7-2), (7-7), (7-8), (7-9), (9-1), and (9-7) are particularly preferred.

In addition, as the nitrogen-containing ring derivative, a nitrogen-containing five-membered ring derivative is preferably exemplified. Examples of the nitrogen-containing five-membered ring include an imidazole ring, a triazole ring, a tetrazole ring, an oxadiazole ring, a thiadiazole ring, an oxatriazole ring, and a thiatriazole ring. Examples of the nitrogen-containing five-membered ring derivative include a benzimidazole ring, a benzotriazole ring, a pyridinoimidazole ring, a pyrimidinoimidazole ring, and a pyridazinoimidazole ring. Particularly preferred is a compound represented by the following general formula (B).

[Chem. 55]

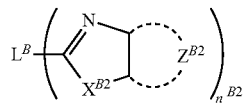

(B)

In the general formula (B), $L^B$ represents a divalent or more linking group. Examples thereof include a carbon atom, a silicon atom, a nitrogen atom, a boron atom, an oxygen atom, a sulfur atom, metal atoms (for example, a barium atom and a beryllium atom), an aromatic hydrocarbon ring, and an aromatic heterocycle. Of those, a carbon atom, a nitrogen atom, a silicon atom, a boron atom, an oxygen atom, a sulfur atom, an aromatic hydrocarbon ring, and an aromatic heterocyclic group are preferred, and a carbon atom, a silicon atom, an aromatic hydrocarbon ring, and an aromatic heterocyclic group are more preferred.

The aromatic hydrocarbon ring and the aromatic heterocyclic group each represented by $L^B$ may have a substituent, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, or an aromatic heterocyclic group, more preferably an alkyl group, an aryl group, an alkoxy group, an aryloxy group, a halogen atom, a cyano group, or an aromatic heterocyclic group, still more preferably an alkyl group, an aryl group, an alkoxy group, an aryloxy group, an aromatic heterocyclic group, particularly preferably an alkyl group, an aryl group, an alkoxy group, or an aromatic heterocyclic group.

Specific Examples of $L^B$ are as shown below.

[Chem. 56]

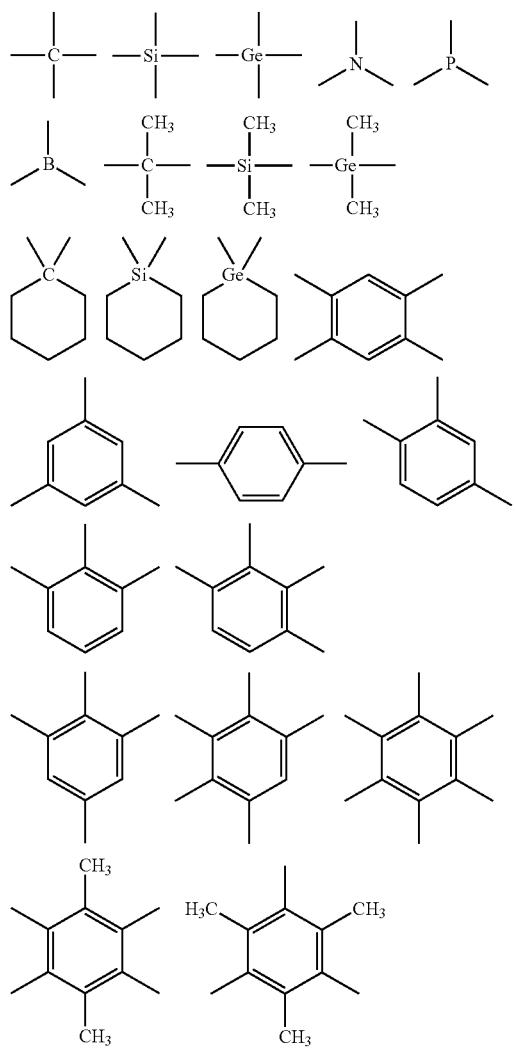

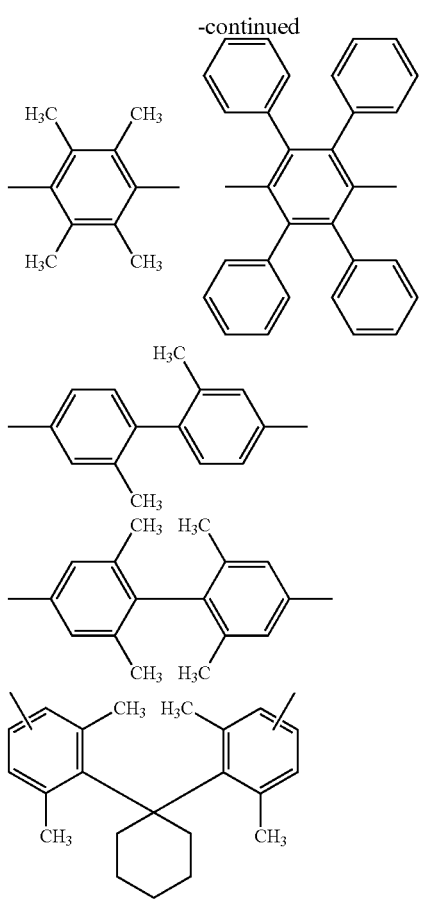

$X^{B2}$ in the general formula (B) represents —O—, —S—, or —N($R^{B2}$)—. $R^{B2}$ represents a hydrogen atom, an aliphatic hydrocarbon group, an aryl group, or a heterocyclic group.

The aliphatic hydrocarbon group represented by $R^{B2}$ is a linear or branched alkyl group (an alkyl group having preferably 1 to 20 carbon atoms, more preferably 1 to 12 carbon atoms, particularly preferably 1 to 8 carbon atoms such as a methyl group, an ethyl group, an isopropyl group, a t-butyl group, a n-octyl group, a n-decyl group, or a n-hexadecyl group), a cycloalkyl group (a cycloalkyl group having preferably 3 to 10 ring carbon atoms such as a cyclopropyl group, a cyclopentyl group, or a cyclohexyl group), an alkenyl group (an alkenyl group having preferably 2 to 20 carbon atoms, more preferably 2 to 12 carbon atoms, particularly preferably 2 to 8 carbon atoms such as a vinyl group, an allyl group, a 2-butenyl group, or a 3-pentenyl group), or an alkynyl group (an alkynyl group having preferably 2 to 20 carbon atoms, more preferably 2 to 12 carbon atoms, particularly preferably 2 to 8 carbon atoms such as a propargyl group or a 3-pentynyl group). Of those, an alkyl group is preferred.

The aryl group represented by $R^{B2}$ is a monocycle or a fused ring, and is an aryl group having preferably 6 to 30 ring carbon atoms, more preferably 6 to 20 ring carbon atoms, still more preferably 6 to 12 ring carbon atoms. Examples thereof include a phenyl group, a 2-methylphenyl group, a 3-methylphenyl group, a 4-methylphenyl group, a 2-methoxyphenyl group, a 3-trifluoromethylphenyl group, a pentafluorophenyl group, a 1-naphthyl group, and a 2-naphthyl group. Of those, a phenyl group and a 2-methylphenyl group are preferred.

The heterocyclic group represented by $R^{B2}$ is a monocycle or a fused ring, and is a heterocyclic group having preferably 1 to 20 ring carbon atoms, more preferably 1 to 12 ring carbon atoms, still more preferably 2 to 10 ring carbon atoms. The heterocyclic group is an aromatic heterocyclic group containing at least one heteroatom out of a nitrogen atom, an oxygen atom, a sulfur atom, and a selenium atom. Examples of the heterocyclic group include groups derived from pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, tetrazaindene, carbazole, and azepine. Of those, preferred are groups derived from furan, thiophene, pyridine, pyrazine, pyrimidine, pyridazine, triazine, quinoline, phthalazine, naphthyridine, quinoxaline, and quinazoline, more preferred are groups derived from furan, thiophene, pyridine, and quinoline, and still more preferred is a quinolinyl group.

The aliphatic hydrocarbon group, the aryl group, and the heterocyclic group each represented by $R^{B2}$ may have a substituent, and the substituent is preferably an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, an aromatic heterocyclic group, more preferably an alkyl group, an aryl group, an alkoxy group, an aryloxy group, a halogen atom, a cyano group, or an aromatic heterocyclic group, still more preferably an alkyl group, an aryl group, an alkoxy group, an aryloxy group, or an aromatic heterocyclic group, particularly preferably an alkyl group, an aryl group, an alkoxy group, or an aromatic heterocyclic group.

$R^{B2}$ represents preferably an aliphatic hydrocarbon group, an aryl group, or a heterocyclic group, more preferably an aliphatic hydrocarbon group (a group having preferably 6 to 30 carbon atoms, more preferably 6 to 20 carbon atoms, still more preferably 6 to 12 carbon atoms) or an aryl group, still more preferably an aliphatic hydrocarbon group (a group having preferably 1 to 20 carbon atoms, more preferably 1 to 12 carbon atoms, still more preferably 2 to 10 carbon atoms).

$X^{B2}$ represents preferably —O— or —N($R^{B2}$)—, more preferably —N($R^{B2}$)—.

$Z^{B2}$ represents an atomic group needed for forming an aromatic ring, and the aromatic ring formed of $Z^{B2}$ may be any of an aromatic hydrocarbon ring and an aromatic heterocycle. Specific examples thereof include a benzene ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrrazole ring. Of those, preferred are a benzene ring, a pyridine ring, a pyrazine ring, a pyrimidine ring, and a pyridazine ring, more preferred are a benzene ring, a pyridine ring, and a pyrazine ring, still more preferred are a benzene ring and a pyridine ring, and particularly preferred is a pyridine ring.

The aromatic ring formed of $Z^{B2}$ may further form a fused ring with any other ring, and may have a substituent. Examples of the substituent include the same examples as those listed for the substituent for a group represented by the $L^B$. Of those, preferred are an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a sulfonyl group, a halogen atom, a cyano group, and a heterocyclic group, more preferred are an alkyl group, an aryl group, an alkoxy group, an aryloxy group, a halogen atom, a cyano group, and a heterocyclic group, still more preferred are an alkyl group, an aryl group, an alkoxy group, an aryloxy group, and an aromatic heterocyclic group, and particularly preferred are an alkyl group, an aryl group, an alkoxy group, and an aromatic heterocyclic group.

$n^{B2}$ represents an integer of 1 to 4, preferably 2 or 3.

Of the nitrogen-containing five-membered ring derivatives each represented by the general formula (B), a derivative represented by the following general formula (B') is more preferred.

[Chem. 57]

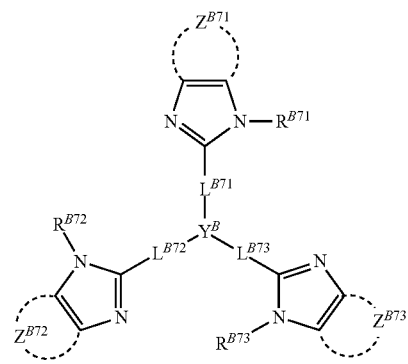

(B')

In the general formula (B'), $R^{B71}$, $R^{B72}$ and $R^{B73}$ each have the same meaning and preferred range as those of $R^{B2}$ in the general formula (B).

$Z^{B71}$, $Z^{B72}$, and $Z^{B73}$ each have the same meaning and preferred range as those of $Z^{B2}$ in the general formula (B).

$L^{B71}$, $L^{Z72}$, and $L^{B73}$ each represent a linking group, and examples of the linking group include examples obtained by making the examples of $L^B$ in the general formula (B) divalent. The linking group is preferably a single bond, a divalent aromatic hydrocarbon ring group, a divalent aromatic heterocyclic group, or a linking group formed of a combination of two or more thereof, more preferably a single bond. $L^{B71}$, $L^{B72}$, and $L^{B73}$ may each have a substituent. Examples of the substituent include the same examples as those described for the substituent of the group represented by $L^B$ in the general formula (B). In addition, preferred substituents are as same as those described for the substituent of the group represented by $L^B$.

$Y^B$ represents a nitrogen atom, a 1,3,5-benzenetriyl group, or a 2,4,6-triazinetriyl group. The 1,3,5-benzenetriyl group may have a substituent at each of its 2-, 4-, and 6-positions, and examples of the substituent include an alkyl group, an aromatic hydrocarbon ring group, and a halogen atom.

Specific examples of the nitrogen-containing five-membered ring derivative represented by the general formula (B) or the general formula (B') are shown below, but not limited to these exemplified compounds.

[Chem. 58]
(B-1) 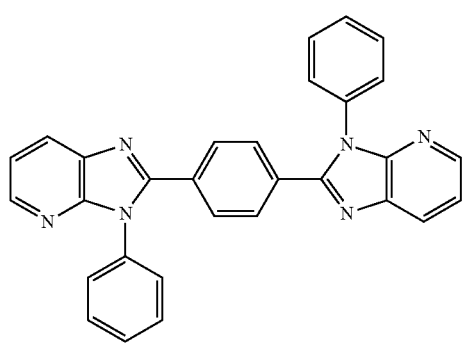
(B-2) 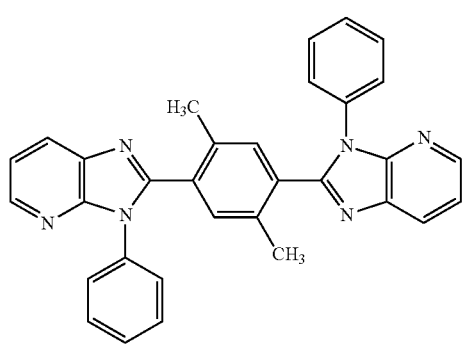
(B-3) 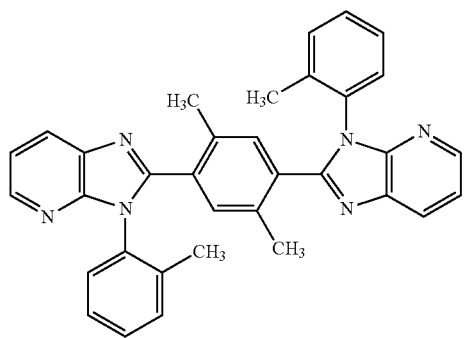
(B-4) 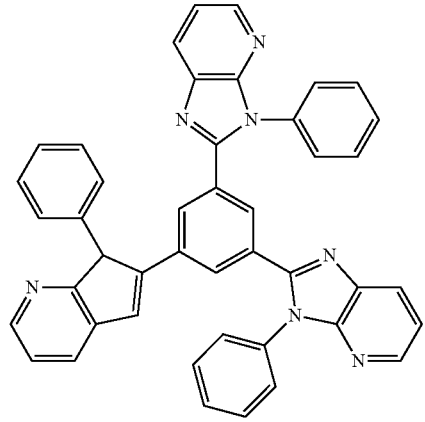
(B-5) 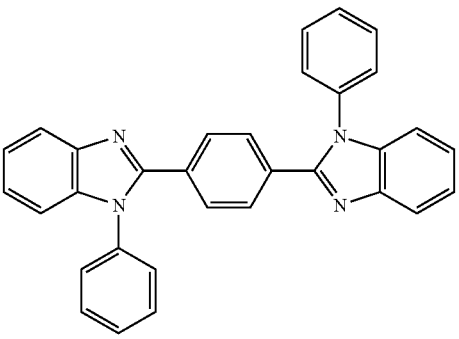
(B-6) 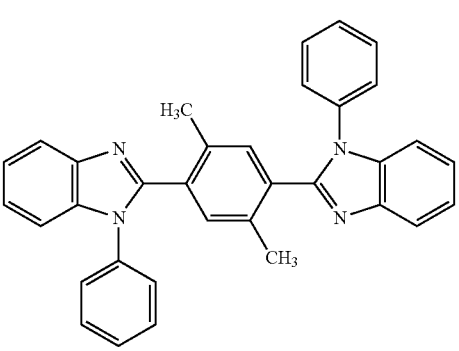
(B-7) 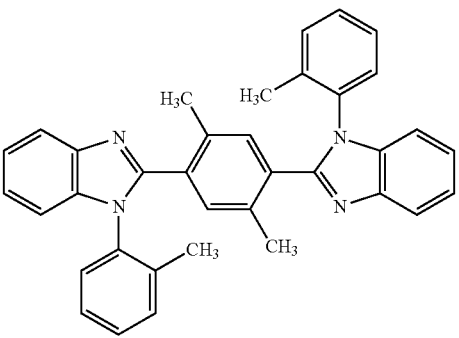
(B-8) 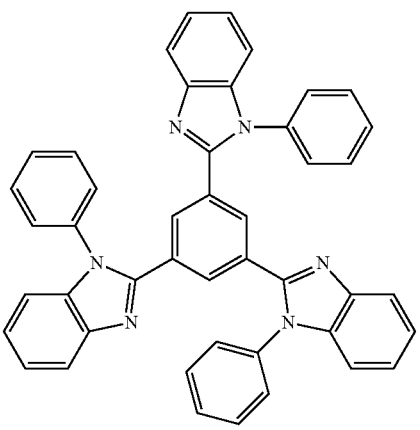

[Chem. 59]
(B-9)
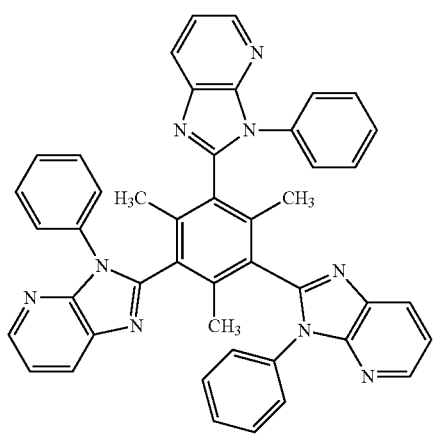
(B-10)
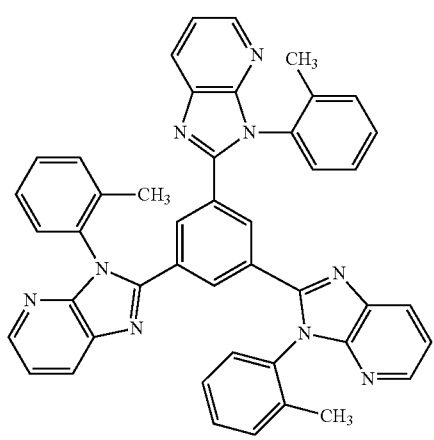
(B-11)
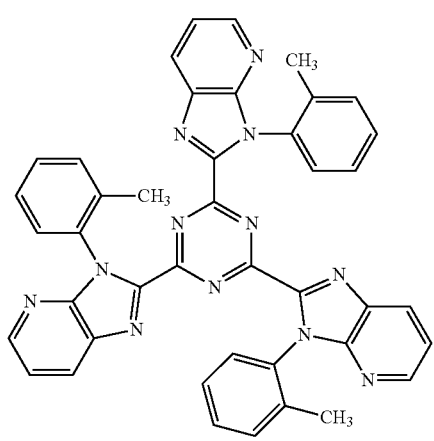
(B-12)
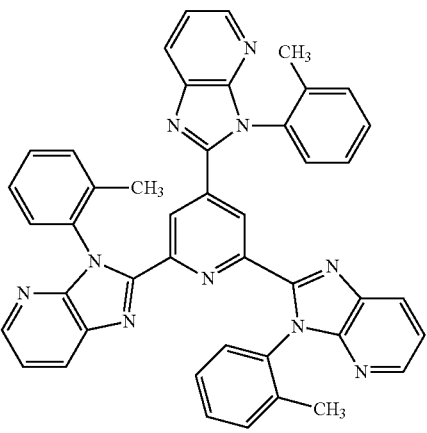
(B-13)
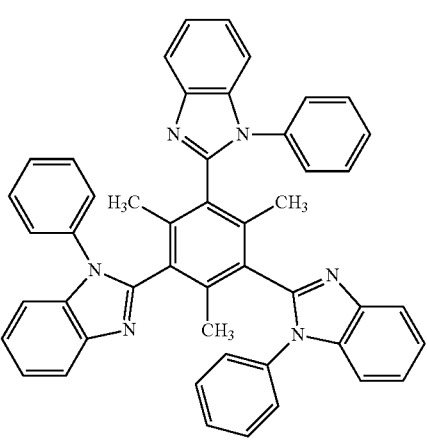
(B-14)
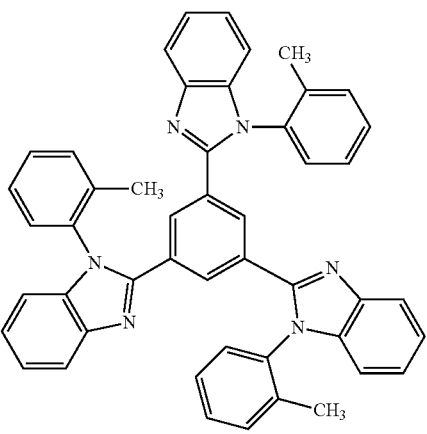

Specific examples of the electron transporting compounds are shown below, but not particularly limited thereto.

[Chem. 60]

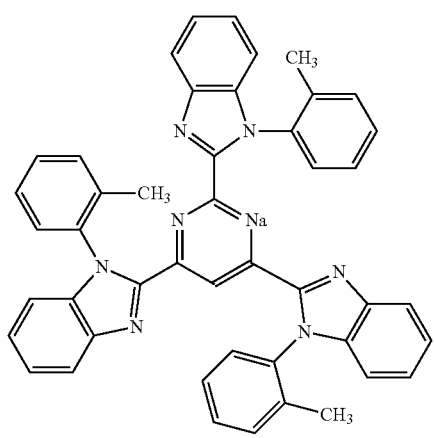
(B-15)

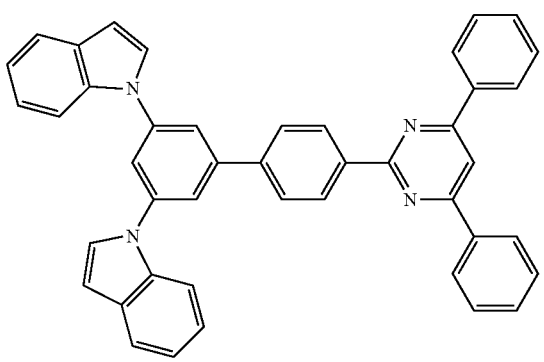

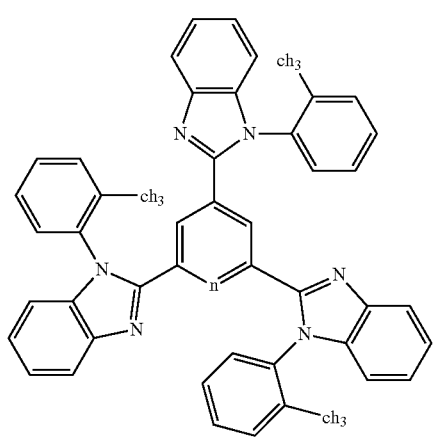
(B-16)

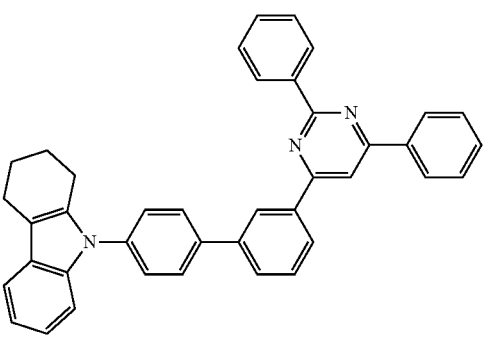

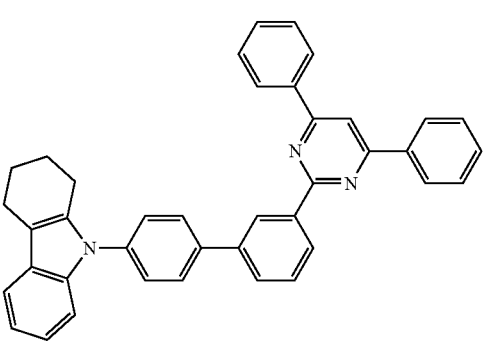

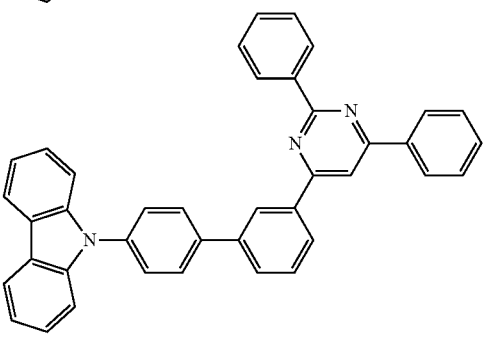

A compound forming each of the electron injecting layer and the electron transporting layer is also, for example, a compound having a structure obtained by combining an electron-deficient, nitrogen-containing five-membered ring skeleton or an electron-deficient, nitrogen-containing six-membered ring skeleton and a substituted or unsubstituted indole skeleton, a substituted or unsubstituted carbazole skeleton, or a substituted or unsubstituted azacarbazole skeleton. In addition, suitable examples of the electron-deficient, nitrogen-containing five-membered ring skeleton or the electron-deficient, nitrogen-containing six-membered ring skeleton include molecular skeletons such as pyridine, pyrimidine, pyrazine, triazine, triazole, oxadiazole, pyrazole, imidazole, quinoxaline, and pyrrole skeletons, and benzimidazole and imidazopyridine in which the skeletons are fused with each other. Of those combinations, pyridine, pyrimidine, pyrazine, and triazine skeletons and carbazole, indole, azacarbazole, and quinoxaline skeletons are preferred examples. The skeletons may be substituted or unsubstituted.

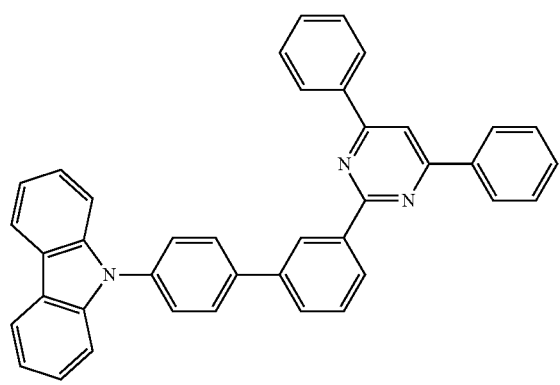
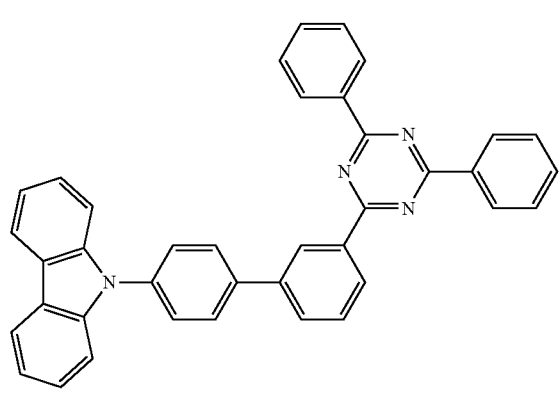
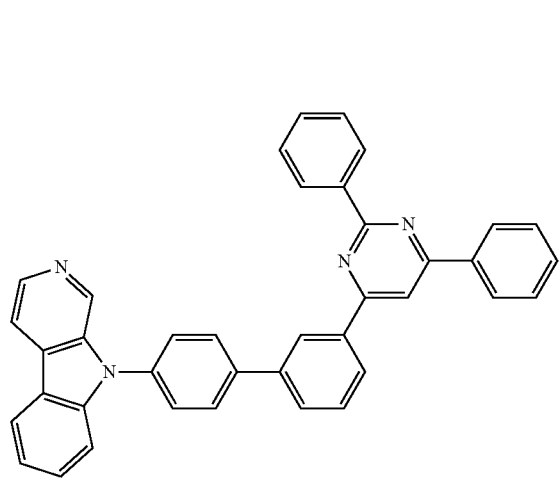
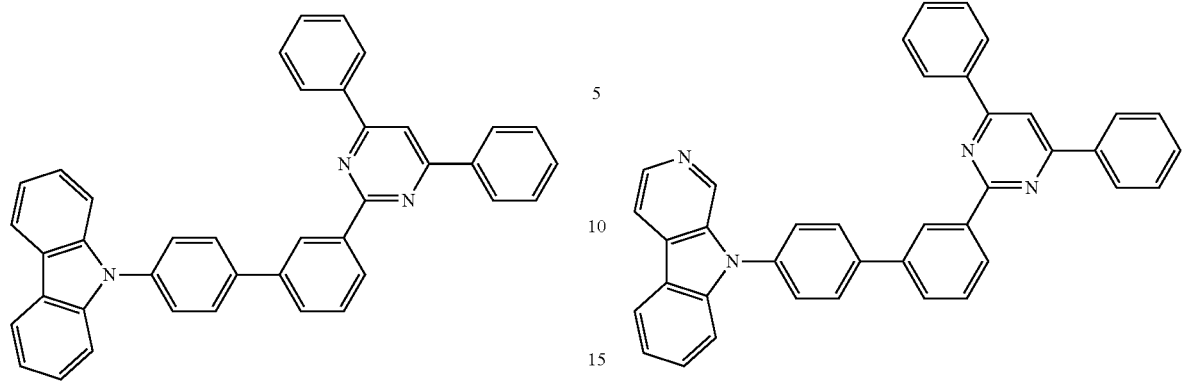
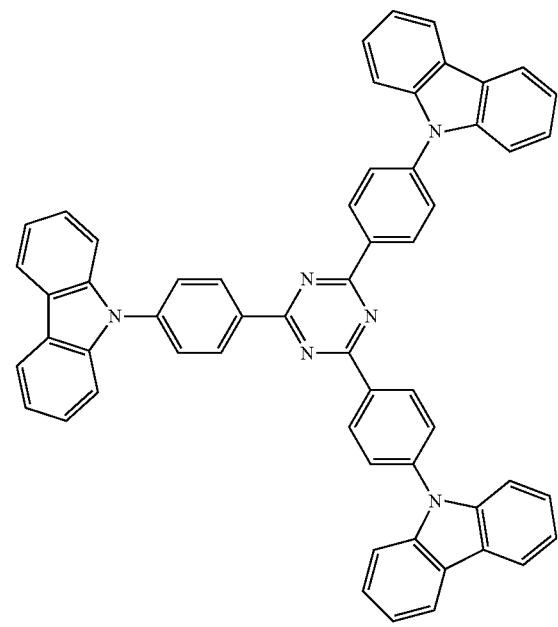
[Chem. 61]
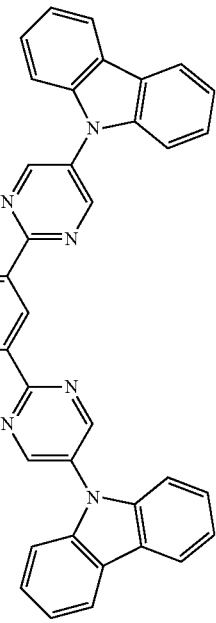

143
-continued
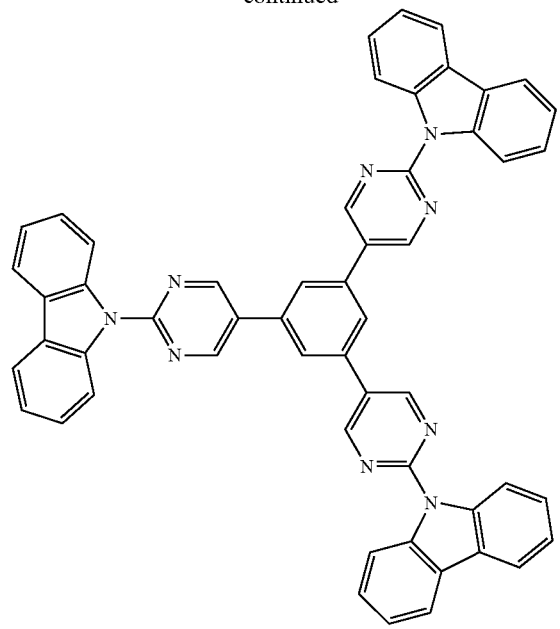
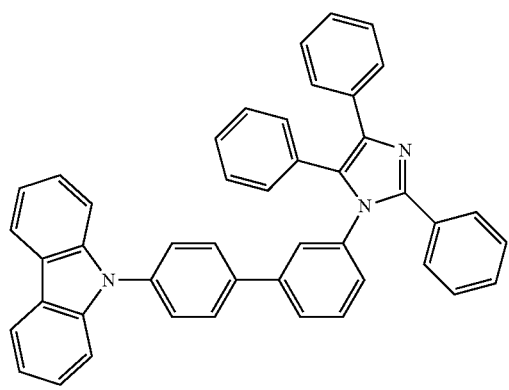
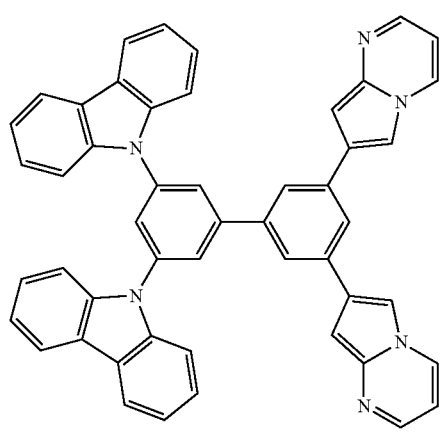
144
-continued
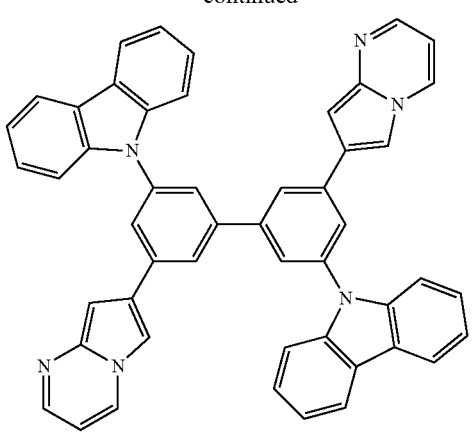
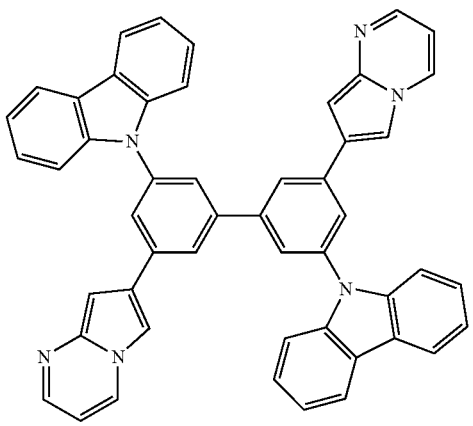
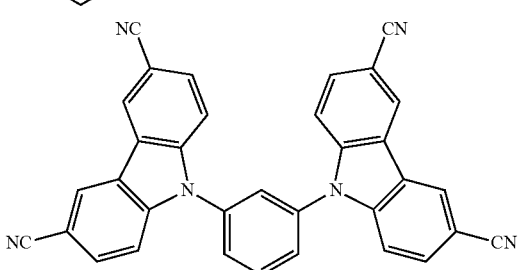
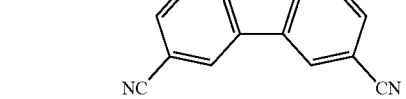
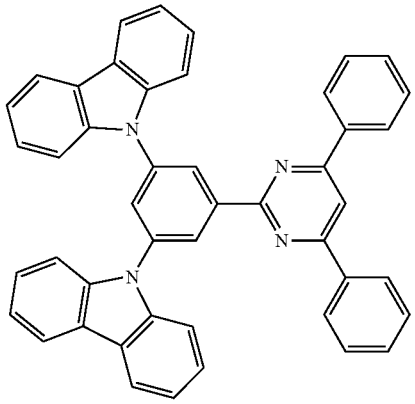

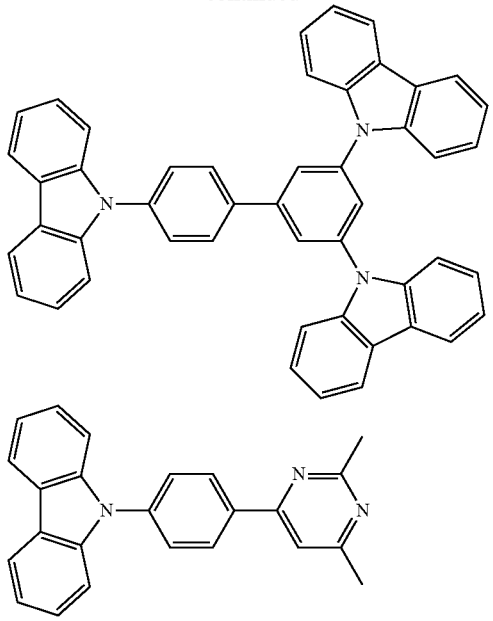

Each of the electron injecting layer and the electron transporting layer may be of a monolayer structure formed of one or two or more kinds of the materials, or may be of a multi-layered structure formed of the plurality of layers identical to or different from each other in composition. Materials for those layers each preferably have a n-electron-deficient, nitrogen-containing heterocyclic group.

In addition, an insulator or semiconductor serving as an inorganic compound as well as the nitrogen-containing ring derivative is preferably used as a component of the electron injecting layer. When the electron injecting layer is formed of an insulator or semiconductor, current leakage can be effectively prevented, and the electron injecting property of the layer can be improved.

As the insulator, at least one metal compound selected from the group consisting of alkali metal chalcogenides, alkaline earth metal chalcogenides, alkali metal halides, and alkaline earth metal halides is preferably used. It is preferred that the electron injecting layer be formed of the alkali metal chalcogenide or the like because the electron injecting property can be further improved. Specifically, preferred examples of the alkali metal chalcogenide include $Li_2O$, $K_2O$, $Na_2S$, $Na_2Se$, and $Na_2O$, and preferred examples of the alkaline earth metal chalcogenide include CaO, BaO, SrO, BeO, BaS, and CaSe. In addition, preferred examples of the alkali metal halide include LiF, NaF, KF, LiCl, KCl, and NaCl. Further, preferred examples of the alkaline earth metal halide include fluorides such as $CaF_2$, $BaF_2$, $SrF_2$, $MgF_2$, and $BeF_2$ and halides other than the fluorides.

In addition, examples of the semiconductor include oxides, nitrides, and oxynitrides containing at least one element selected from the group consisting of Ba, Ca, Sr, Yb, Al, Ga, In, Li, Na, Cd, Mg, Si, Ta, Sb, and Zn. One kind thereof may be used alone, or two or more kinds thereof may be used in combination. In addition, it is preferred that the inorganic compound forming the electron injecting layer form a microcrystalline or amorphous insulating thin film. When the electron injecting layer is formed of the insulating thin film, a more uniform thin film can be formed, and defects of pixels such as dark spots can be decreased. It should be noted that examples of the inorganic compound include an alkali metal chalcogenide, an alkaline earth metal chalcogenide, an alkali metal halide, and an alkaline earth metal halide.

In addition, the reductive dopant can be preferably incorporated into the electron injecting layer in the present invention.

It should be noted that the thickness of each of the electron injecting layer and the electron transporting layer, which is not particularly limited, is preferably 1 to 100 nm.

An aromatic amine compound such as an aromatic amine derivative represented by the general formula (I) is suitably used in the hole injecting layer or hole transporting layer (a hole injecting/transporting layer is also included in this category).

[Chem. 62]

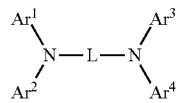
(I)

In the general formula (1), $Ar^1$ to $Ar^4$ each represent a substituted or unsubstituted aryl group having 6 to 50 ring carbon atoms, or a substituted or unsubstituted heterocyclic group having 5 to 50 ring atoms.

Examples of the substituted or unsubstituted aryl group having 6 to 50 ring carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, a o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, 4"-t-butyl-p-terphenyl-4-yl group, a fluoranthenyl group, and a fluorenyl group.

Examples of the substituted or unsubstituted heterocyclic group having 5 to 50 ring atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acrydinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group. Preferred examples thereof include a phenyl group, a naphthyl group, a biphenyl group, an anthranyl group, a phenanthryl group, a pyrenyl group, a chrysenyl group, a fluoranthenyl group, and a fluorenyl group.

L represents a linking group. Specifically, L represents a substituted or unsubstituted arylene group having 6 to 50 ring carbon atoms, a substituted or unsubstituted heteroarylene group having 5 to 50 ring atoms, or a divalent group produced by binding two or more arylene groups or heteroarylene groups with a single bond, an ether bond, a thioether bond, an alkylene group having 1 to 20 carbon atoms, an alkenylene group having 2 to 20 carbon atoms, or an amino group. Examples of the arylene group having to 50 ring carbon atoms include a 1,4-phenylene group, a 1,2-phenylene group, a 1,3-phenylene group, a 1,4-naphthylene group, a 2,6-naphthylene group, a 1,5-naphthylene group, and a 9,10-anthranylene group, a 9,10-phenanthrenylene group, a 3,6-phenanthrenylene group, a 1,6-pyrenylene group, a 2,7-pyrenylene group, a 6,12-chrysenylene group, a 4,4'-biphenylene group, a 3,3'-biphenylene group, a 2,2'-biphenylene group, and a 2,7-fluorenylene group. Examples of the arylene group having 5 to 50 ring atoms include, a 2,5-thiophenylene group, a 2,5-silolylene group, and a 2,5-oxadiazolylene group. Of those, preferred are a 1,4-phenylene group, a 1,2-phenylene group, a 1,3-phenylene group, a 1,4-naphthylene group, a 9,10-anthranylene group, a 6,12-chrysenylene group, a 4,4'-biphenylene group, a 3,3'-biphenylene group, a 2,2'-biphenylene group, and a 2,7-fluorenylene group.

When L represents a linking group formed of two or more arylene groups or heteroarylene groups, adjacent arylene groups or heteroarylene groups may form another ring by binding each other with a divalent group. Examples of the divalent group for forming the ring include a tetramethylene group, a pentamethylene group, a hexamethylene group, a diphenylmethane-2,2'-diyl group, a diphenylethane-3,3'-diyl group, and a diphenylpropane-4,4'-diyl group.

Examples of the substituent represented by each of $Ar^1$ to $Ar^4$ and L include a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted heteroaryloxy group having 5 to 50 ring atoms, a substituted or unsubstituted arylthio group having 6 to 50 ring carbon atoms, a substituted or unsubstituted heteroarylthio group having 5 to 50 ring atoms, a substituted or unsubstituted alkoxycarbonyl group having 2 to 50 carbon atoms, an amino group substituted with a substituted or unsubstituted aryl group having 6 to 50 ring carbon atoms or a substituted or unsubstituted heterocyclic group having 5 to 50 ring atoms, a halogen group, a cyano group, a nitro group, and a hydroxyl group.

Examples of the substituted or unsubstituted aryl group having 6 to 50 ring carbon atoms include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, and a fluorenyl group.

Examples of the substituted or unsubstituted heterocyclic group having 5 to 50 ring atoms include a 1-pyrrolyl group, a 2-pyrrolyl group, a 3-pyrrolyl group, pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Examples of the substituted or unsubstituted alkyl group having 1 to 50 carbon atoms include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the substituted or unsubstituted cycloalkyl group having 3 to 50 carbon atoms include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

The substituted or unsubstituted alkoxy group having 1 to 50 carbon atoms is a group represented by —OY. Examples of the group represented by Y include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the substituted or unsubstituted aralkyl group having 7 to 50 carbon atoms include a benzyl group, a 1-phenylethyl group, a 2-phenylethyl group, a 1-phenylisopropyl group, a 2-phenylisopropyl group, a phenyl-t-butyl group, a α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, a m-nitrobenzyl group, an o-nitrobenzyl group, a p-cyanobenzyl group, a m-cyanobenzyl group, an o-cyanobenzyl group, a 1-hydroxy-2-phenylisopropyl group, and a 1-chloro-2-phenylisopropyl group.

The substituted or unsubstituted aryloxy group having 6 to 50 ring carbon atoms is represented as $-OY^1$, and examples of the group represented by Y' include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, am-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methyl biphenylyl group, and a 4"-t-butyl-p-terphenyl-4-yl group.

The substituted or unsubstituted heteroaryloxy group having 5 to 50 ring atoms is represented as —OZ', and examples of the group represented by Z' include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

The substituted or unsubstituted arylthio group having 6 to 50 ring carbon atoms is represented as —SY", and examples of the group represented by Y" include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, am-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group.

The substituted or unsubstituted heteroarylthio group having 5 to 50 ring atoms is represented as —SZ", and examples of the group represented by Z" include a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

The substituted or unsubstituted alkoxycarbonyl group having 2 to 50 carbon atoms is represented as —COOZ, and examples of the group represented by Z include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

The amino group substituted with a substituted or unsubstituted aryl group having 6 to 50 ring carbon atoms or a substituted or unsubstituted heterocyclic group having 5 to 50 ring atoms is represented as —NPQ, and examples of the groups represented by P and Q include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a 2-pyrrolyl group, a 3-pyrrolyl group, a pyrazinyl group, a 2-pyridinyl group, a 3-pyridinyl group, a 4-pyridinyl group, a 2-indolyl group, a 3-indolyl group, a 4-indolyl group, a 5-indolyl group, a 6-indolyl group, a 7-indolyl group, a 1-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 1-phenoxazinyl group, a 2-phenoxazinyl group, a 3-phenoxazinyl group, a 4-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Specific examples of the compound represented by the general formula (I) are shown below, however, the compound is not limited thereto.

[Chem. 63]

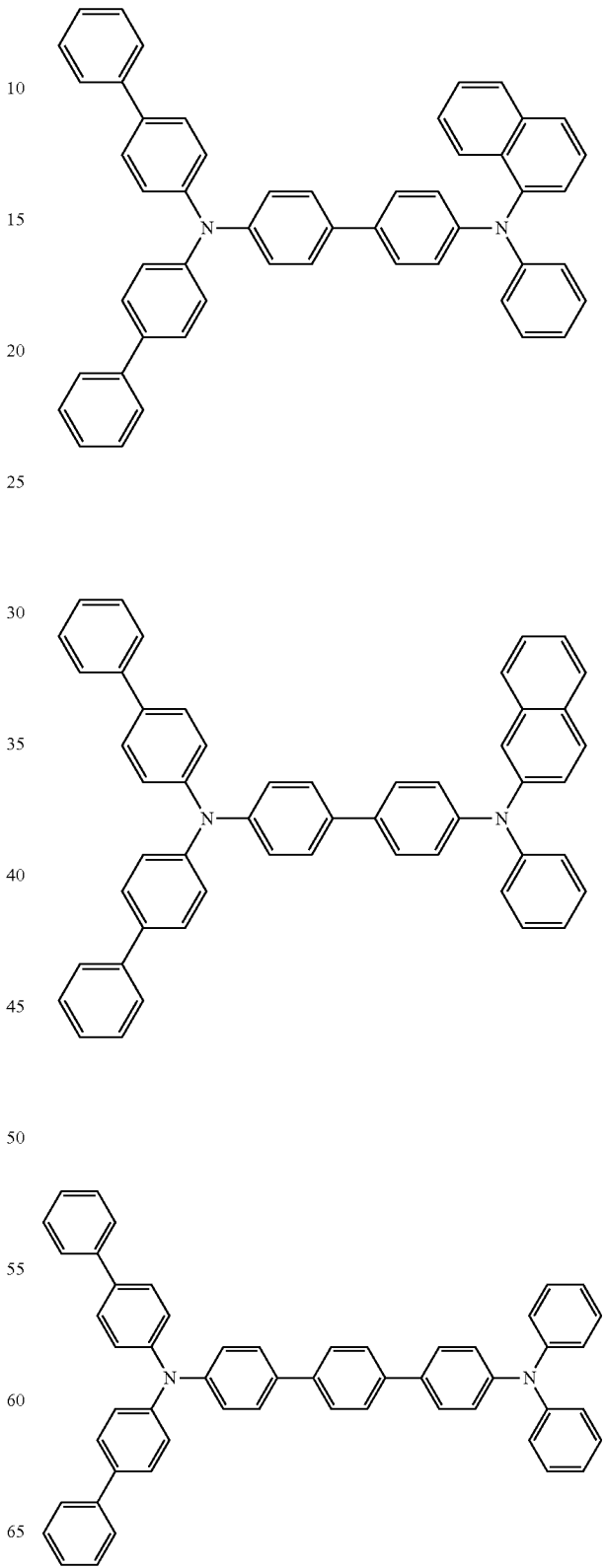

157
-continued
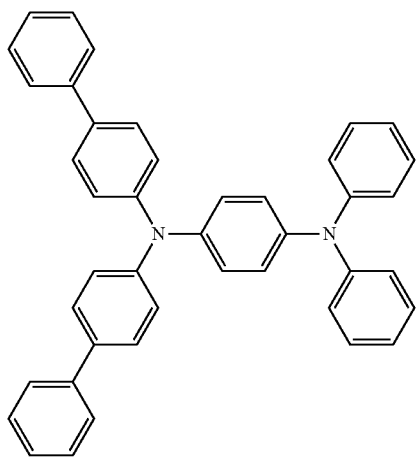
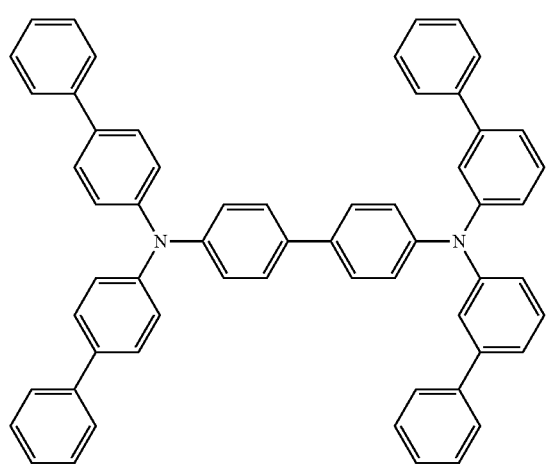
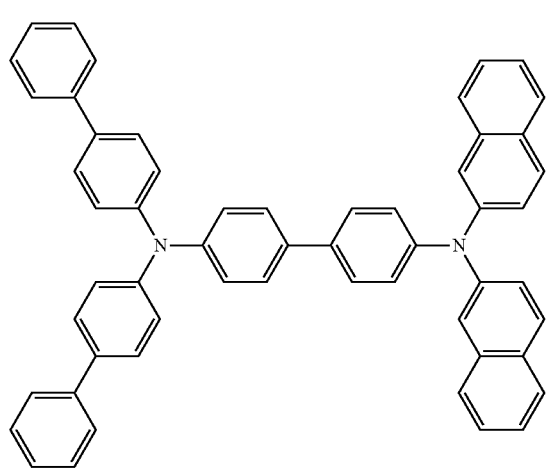
158
-continued
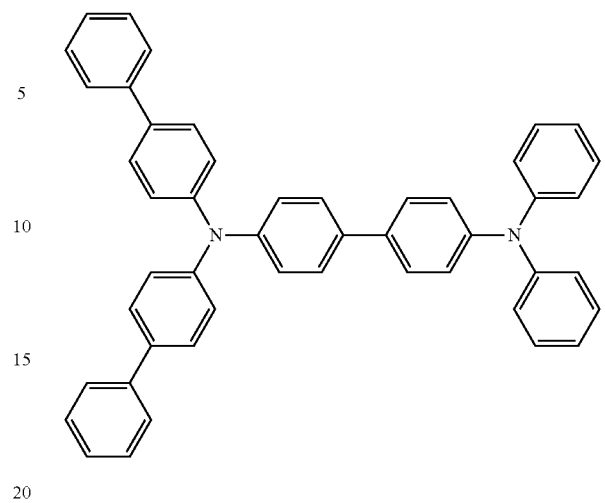
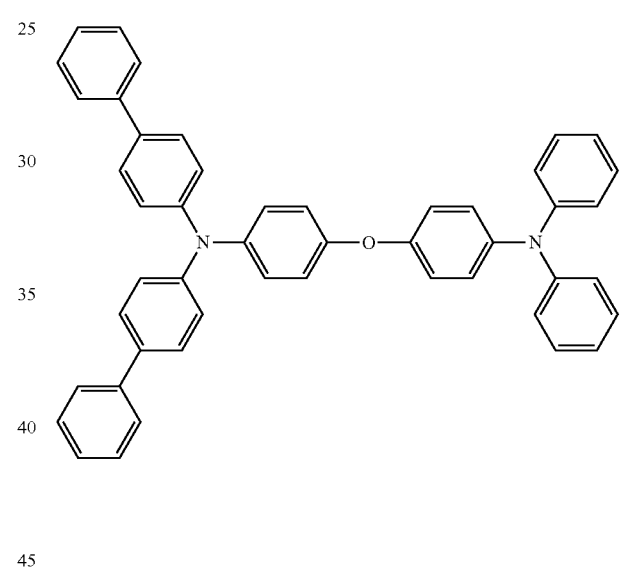
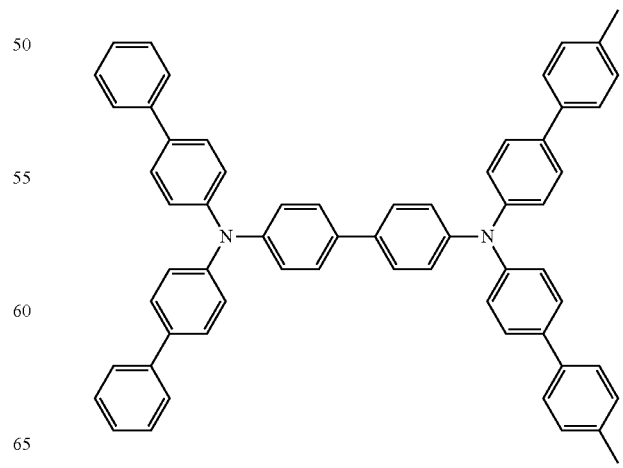

159
-continued
160
-continued
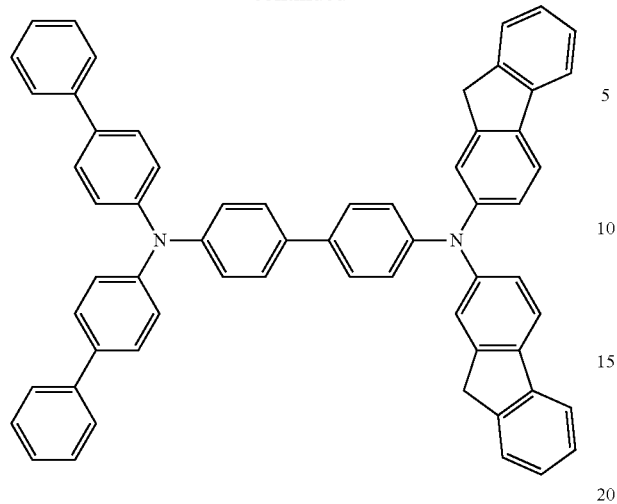
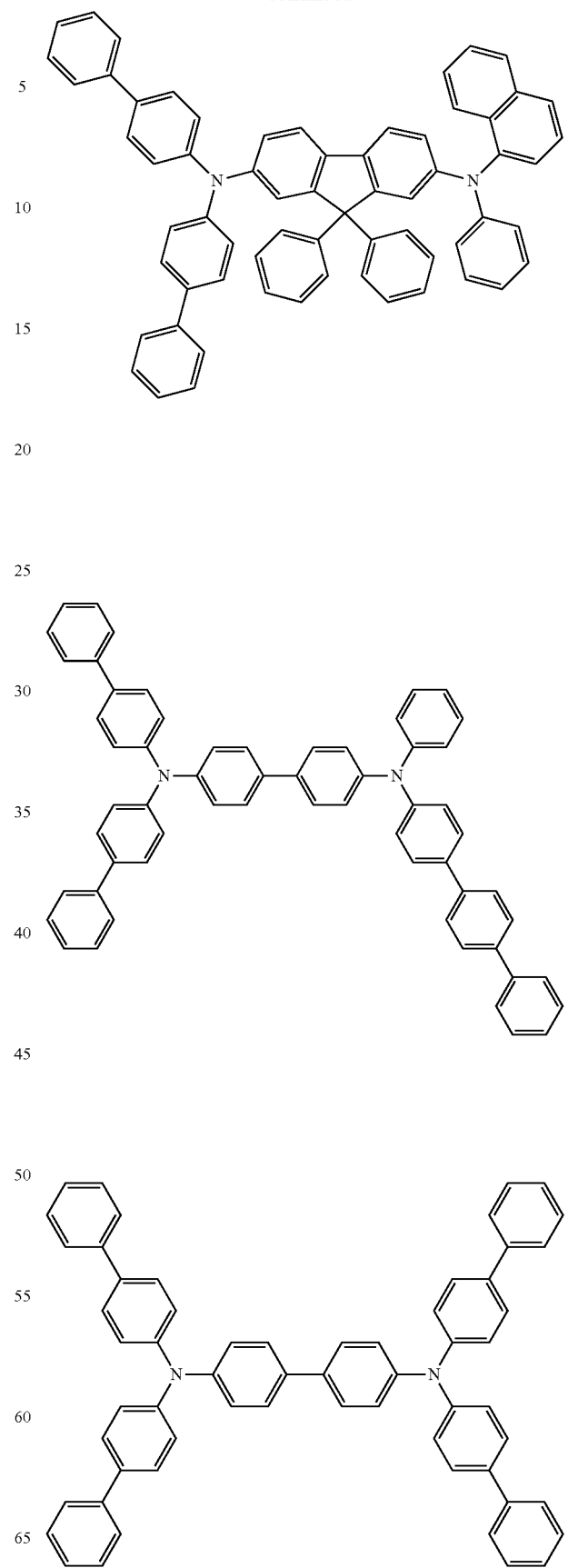

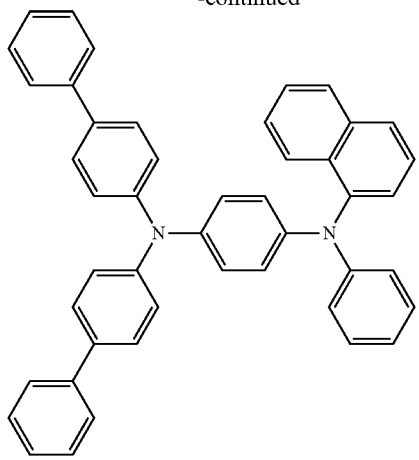
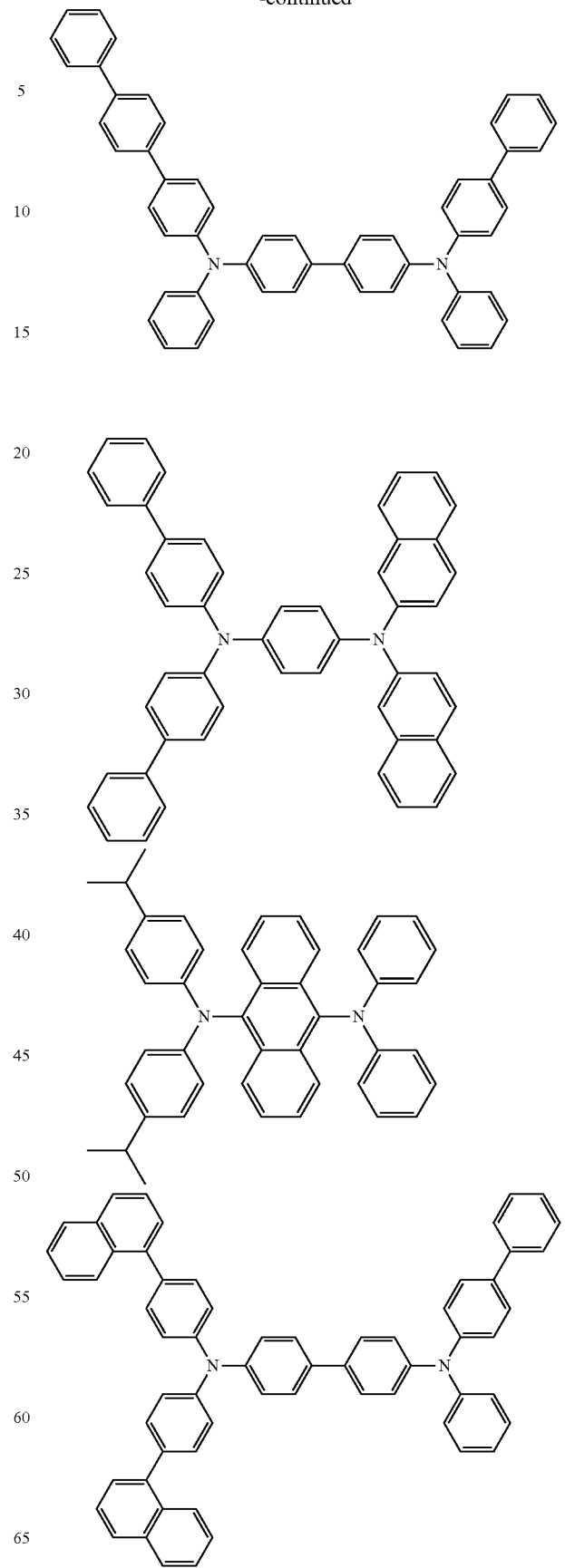

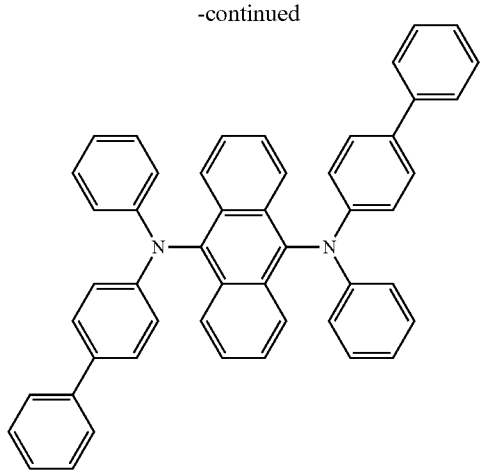

In addition, an aromatic amine represented by the following general formula (II) is also suitably used in the formation of the hole injecting layer or hole transporting layer.

[Chem. 64]

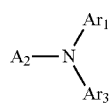

(II)

In the general formula (II), the definitions of $Ar_1$ to $Ar_3$ are the same as those of $Ar^1$ to $Ar^4$ in the general formula (1). Specific examples of the compound represented by the general formula (II) are shown below, but not limited thereto.

[Chem. 65]

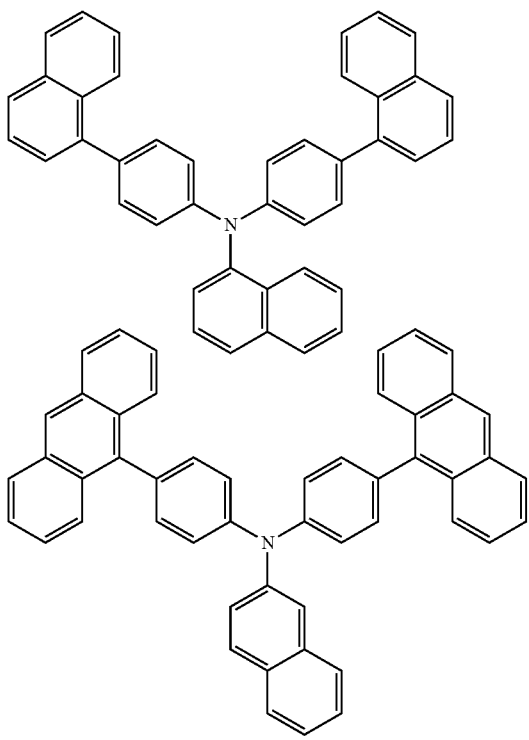

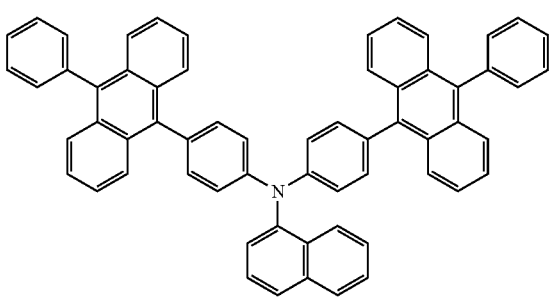

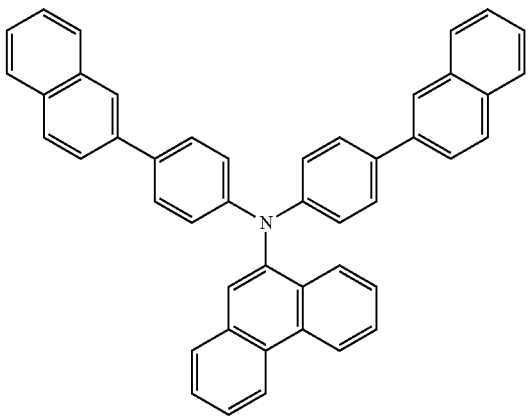

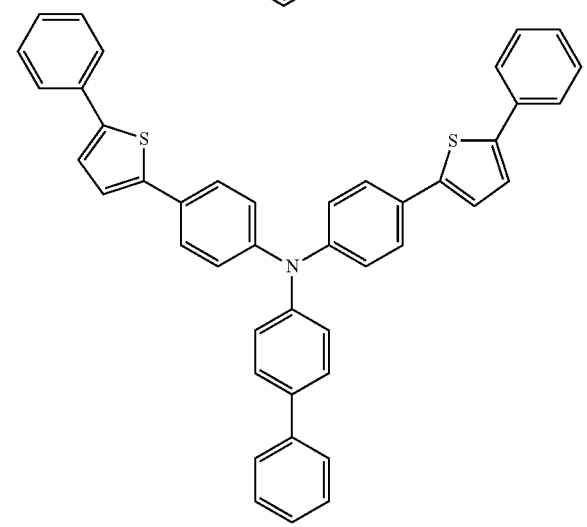

165
-continued
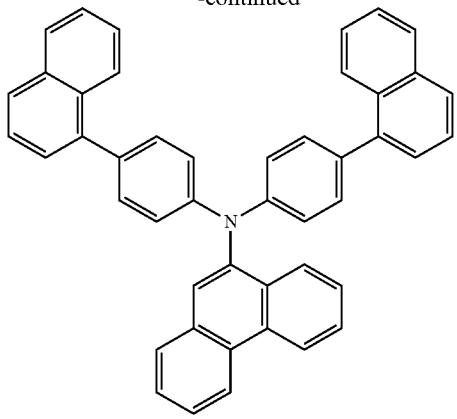
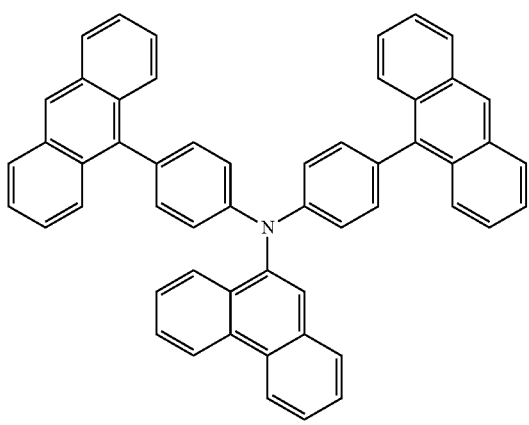
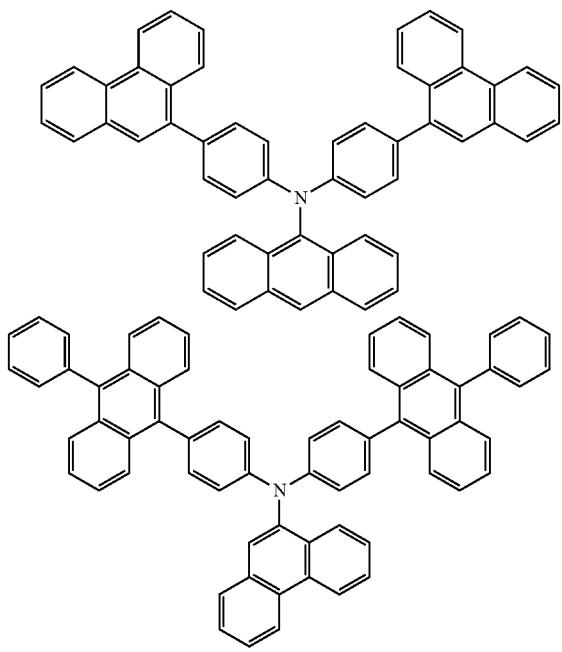
166
-continued
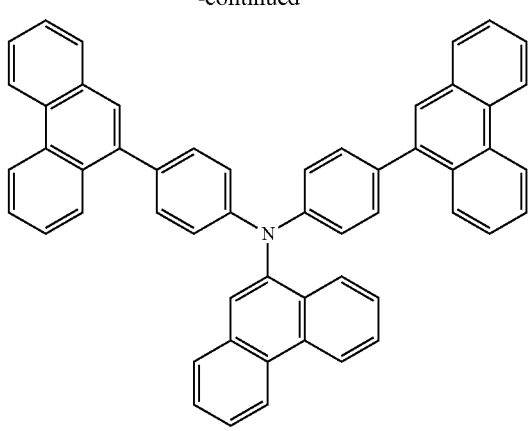
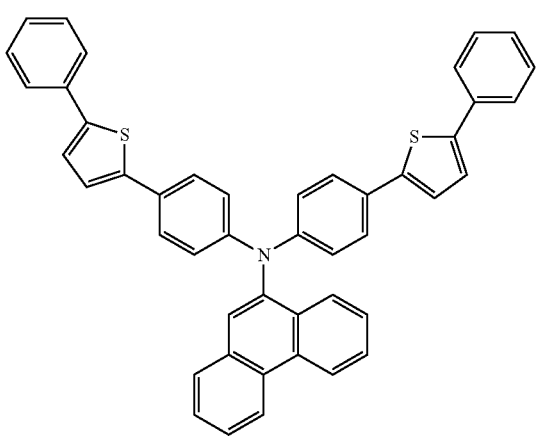
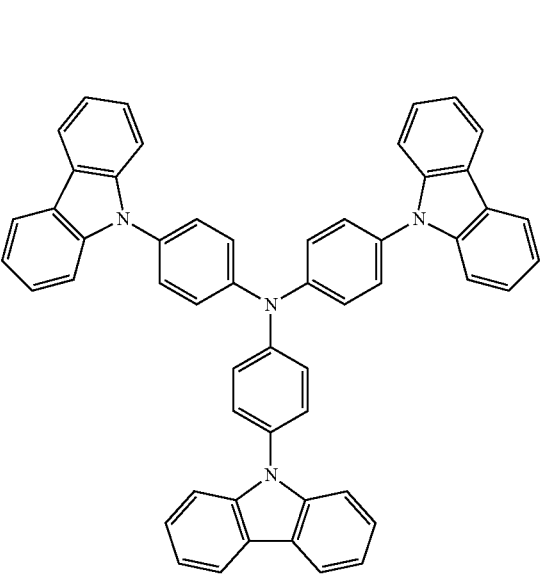

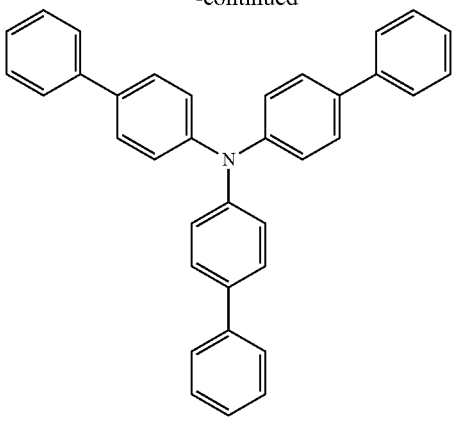

In the present invention, the anode in the organic EL device has the function of injecting holes into the hole transporting layer or the light emitting layer. It is effective that the anode has a work function of 4.5 eV or more. Specific examples of the material for the anode used in the present invention include indium tin oxide alloys (ITO), tin oxide (NESA), gold, silver, platinum, and copper. In addition, as the cathode, a material having a small work function is preferred in view to inject an electron into an electron injecting layer or a light emitting layer. The material for the cathode is not particularly limited, and specifically, indium, aluminum, magnesium, a magnesium-indium alloy, amagnesium-aluminum alloy, an aluminum-lithium alloy, an aluminum-scandium-lithium alloy, a magnesium-silver alloy, or the like may be used.

The method of forming each of the layers in the organic EL device of the present invention is not particularly limited. A conventionally known process such as a vacuum vapor deposition process or a spin coating process can be used for the formation method. The organic thin film layer which is used in the organic EL device of the present invention and which contain the compound represented by the formula (1) can be formed in accordance with a known process such as a vacuum vapor deposition process or a molecular beam epitaxy process (MBE process) or, using a solution prepared by dissolving the compounds into a solvent, in accordance with a coating process such as a dipping process, a spin coating process, a casting process, a bar coating process, or a roll coating process.

The thickness of each organic layer in the organic EL device of the present invention is not particularly limited. In general, an excessively thin layer tends to have defects such as pin holes, whereas an excessively thick layer requires a high applied voltage to decrease the efficiency. Therefore, a thickness in the range of several nanometers to 1 μm is typically preferred.

EXAMPLES

Next, the present invention is described in more detail by way of synthesis examples and examples. Note that the present invention is not limited to the following synthesis examples and examples.

Methods of evaluating an organic EL device are as described below.

(1) External Quantum Efficiency (%)

Its external quantum efficiency at a luminance of 1,000 cd/m$^2$ was measured with a luminance meter (spectral luminance radiometer CS-1000 manufactured by Minolta) at 23° C. under a dry nitrogen gas atmosphere.

(2) Half Lifetime (Hour(s))

A continuous energization test (direct current) was performed at an initial luminance of 1,000 cd/m$^2$ to measure a time period required for the initial luminance to reduce by half.

(3) Voltage (V)

A voltage was applied to the device, which had been subjected to electric wiring, with a KEITHLY 236 SOURCE MEASURE UNIT at 23° C. under a dry nitrogen gas atmosphere to cause the device to emit light, and then the voltage applied to the device was measured by subtracting a voltage applied to a wiring resistance except the device.

Synthesis Example 1

Synthesis of Compound (1)

(1) Synthesis of Compound (1-a)

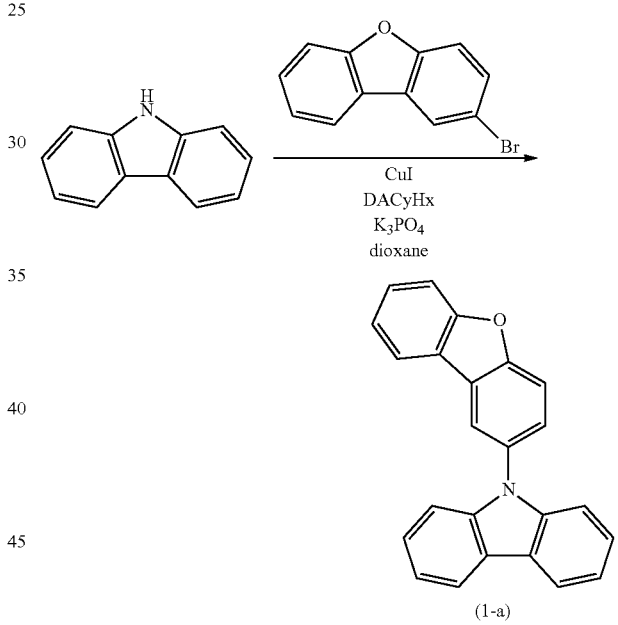

Under a nitrogen atmosphere, 40.1 g (240 mmol) of carbazole, 49.4 g (200 mmol) of 2-bromodibenzofuran, 3.81 g (20 mmol) of copper iodide, 84.91 g (400 mmol) of potassium phosphate, 7.21 ml (60 mmol) of trans-1,2-diaminocyclohexane, and 100 ml of 1,4-dioxane were loaded into a three-necked flask, and then the mixture was refluxed for 24 hours. After the completion of the reaction, the reaction product was cooled to room temperature and then diluted with 400 ml of toluene. An inorganic salt and the like were separated by filtration by subjecting the diluted solution to suction filtration. The filtrate was passed through a silica gel short column and concentrated. The concentrate was washed with a mixed solvent of ethyl acetate and methanol. Thus, a white solid (Compound (1-a)) was obtained (yield: 54.0 g, percent yield: 81%).

(2) Synthesis of Compound (1-b)

[Chem. 68]

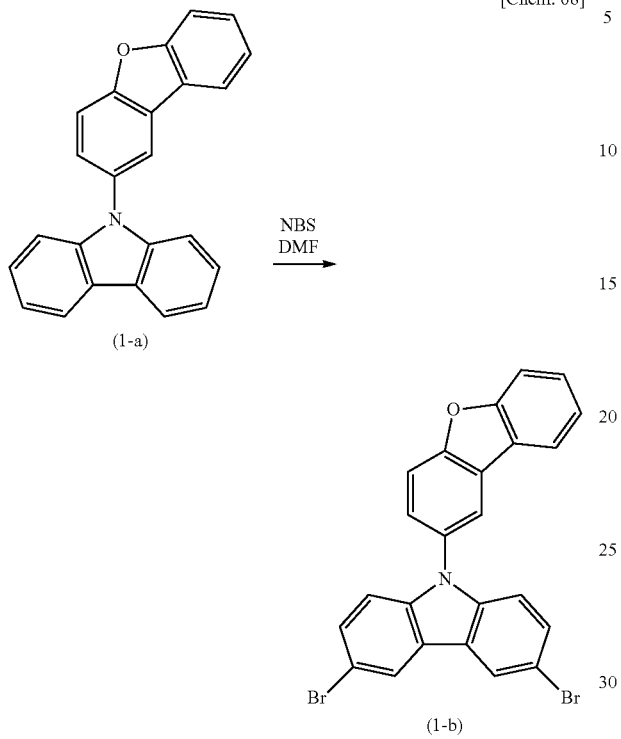

Under an air atmosphere, 7.9 g (19.3 mmol) of Compound (1-a) and 100 ml of N,N-dimethylformamide were loaded into a recovery flask to dissolve the sample, and then the solution was cooled to 0° C. with ice water. 7.04 Grams (39.6 mmol) of N-bromosuccinimide dissolved in 20 ml of N,N-dimethylformamide were slowly added dropwise to the solution over 10 minutes, and then the mixture was stirred at 0° C. for 3 hours. After that, the mixture was left to stand at room temperature for 1 day. After the completion of the reaction, 200 ml of toluene were added to the reaction product and then the mixture was subjected to water washing with a separating funnel twice. The washed product was dried with anhydrous magnesium sulfate, and was then filtered and concentrated. The concentrate was recrystallized from hexane. Thus, a white solid (Compound (1-b)) was obtained (yield: 9.30 g, percent yield: 8571).

(3) Synthesis of Compound (1)

[Chem. 69]

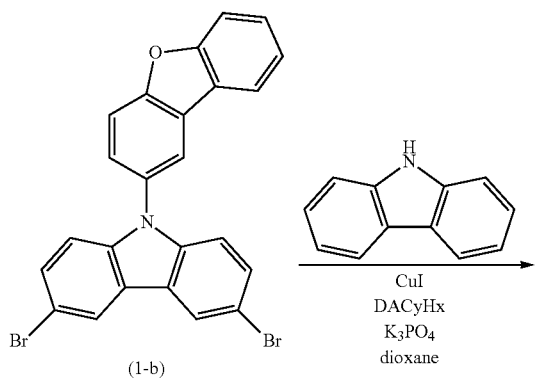

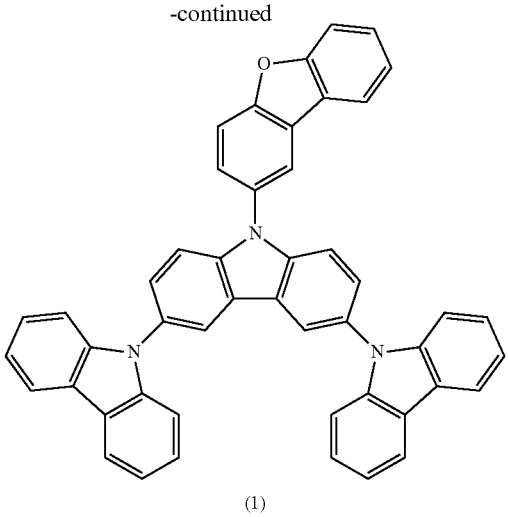

Under a nitrogen atmosphere, 6.55 g (39.2 mmol) of carbazole, 9.26 g (16.3 mmol) of Compound (1-b), 1.55 g (8.15 mmol) of copper iodide, 13.84 g (65.2 mmol) of potassium phosphate, 2.94 ml (24.5 mmol) of trans-1,2-diaminocyclohexane, and 32 ml of 1,4-dioxane were loaded into a three-necked flask, and then the mixture was refluxed for 24 hours. After the completion of the reaction, the reaction product was cooled to room temperature and then diluted with 200 ml of toluene. An inorganic salt and the like were separated by filtration by subjecting the diluted solution to suction filtration. The filtrate was passed through a silica gel short column and concentrated. The concentrate was washed with a mixed solvent of ethyl acetate and hexane. Thus, a white solid (Compound (1)) was obtained (yield: 8.10 g, percent yield: 75%).

Synthesis Example 2

Synthesis of Compound (2)

(1) Synthesis of Compound (2-a)

[Chem. 70]

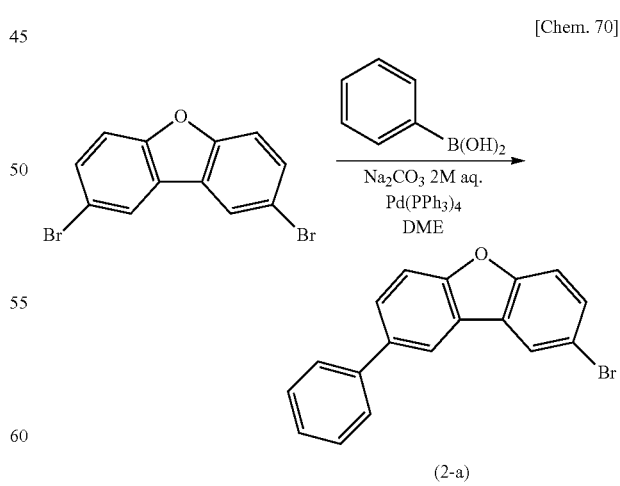

Under a nitrogen atmosphere, 32.6 g (100 mmol) of 2,7-dibromodibenzofuran, 12.2 g (100 mmol) of phenylboronic acid, 100 ml of a 2-M aqueous solution of sodium carbonate, and 100 ml of 1,2-dimethoxyethane were loaded into a three-necked flask, 1.16 g (1 mmol) of tetrakis(triphenylphosphine) palladium were added to the mixed solution, and then the whole was refluxed for 8 hours.

After the completion of the reaction, the reaction product was cooled to room temperature and then extracted with toluene by using a separating funnel. The extract was dried with anhydrous magnesium sulfate, and was then filtered and concentrated. The concentrate was purified by silica gel chromatography (developing solvent: hexane:toluene=8:2). The purified product was recrystallized from hexane. Thus, a white solid (Compound (2-a)) was obtained (yield: 17.8 g, percent yield: 55%).

(2) Synthesis of Compound (2)

[Chem. 71]

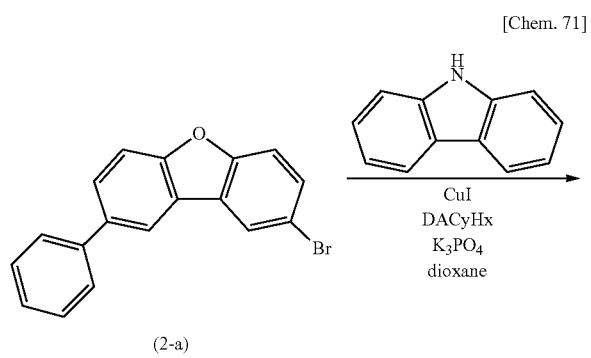

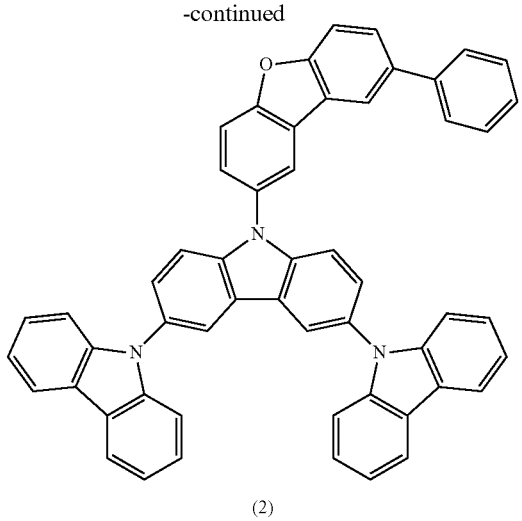

Compound (2) was synthesized in the same manner as in Compounds (1-a) to (1) except that 2-bromodibenzofuran as a raw material was changed to Compound (2-a).

Synthesis Example 3

Synthesis of Compound (15)

(1) Synthesis of Compound (15-a)

[Chem. 72]

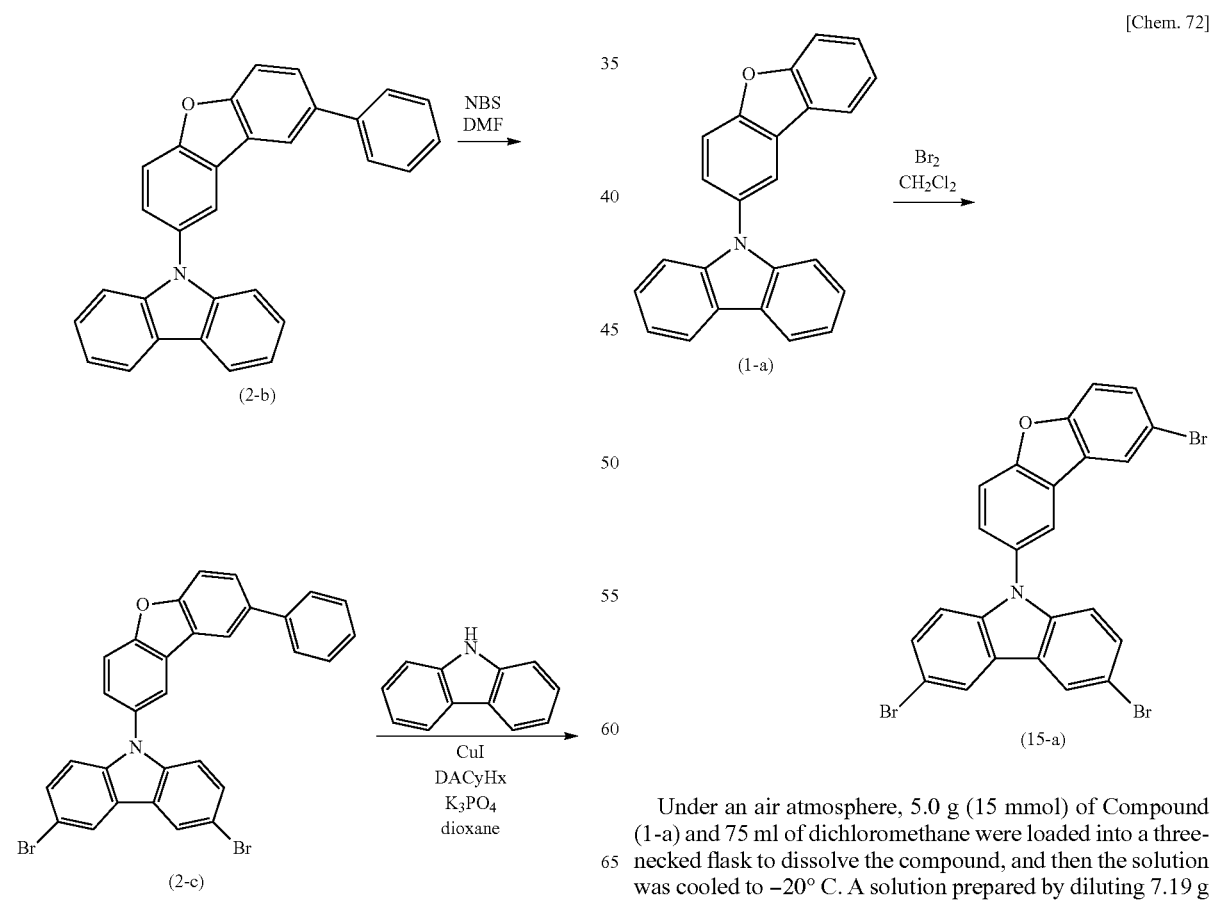

Under an air atmosphere, 5.0 g (15 mmol) of Compound (1-a) and 75 ml of dichloromethane were loaded into a three-necked flask to dissolve the compound, and then the solution was cooled to −20° C. A solution prepared by diluting 7.19 g (45 mmol) of bromine with 45 ml of dichloromethane was dropped to the solution over 10 minutes, and then the mixture was stirred at −20° C. for 1 hour. After that, the temperature of the mixture was returned to room temperature and then the mixture was stirred for 1 day. After the completion of the reaction, an aqueous solution of sodium thiosulfate was added to the reaction product to deactivate the remaining bromine and then the resultant was extracted with dichloromethane by using a separating funnel. The extract was dried with anhydrous magnesium sulfate, and was then filtered and concentrated. The concentrate was recrystallized from a mixed solvent of toluene and hexane twice. Thus, a light brown solid (Compound (15-a)) was obtained (yield: 6.26 g, percent yield: 73%).

(2) Synthesis of Compound (15)

[Chem. 73]

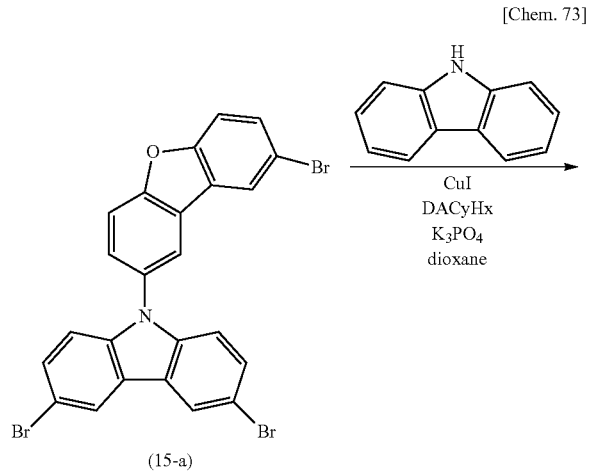

(15-a)

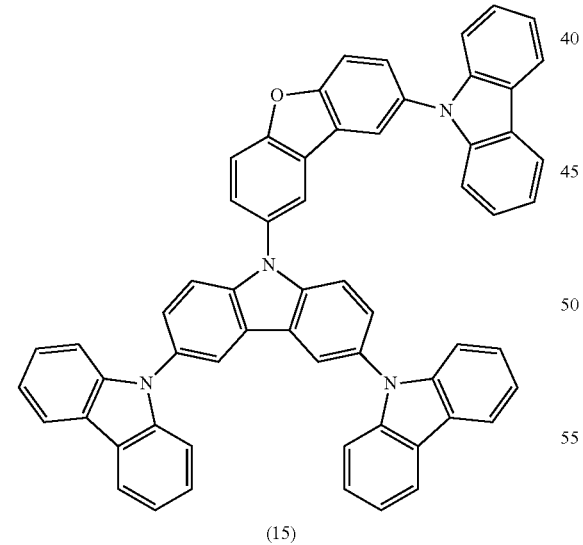

(15)

Under a nitrogen atmosphere, 7.36 g (44 mmol) of carbazole, 6.26 g (11 mmol) of Compound (15-a), 1.05 g (5.5 mmol) of copper iodide, 14.0 g (66 mmol) of potassium phosphate, 1.98 ml (16.5 mmol) of trans-1,2-diaminocyclohexane, and 22 ml of 1,4-dioxane were loaded into a three-necked flask, and then the mixture was refluxed for 24 hours.

After the completion of the reaction, the reaction product was cooled to room temperature and then diluted with 300 ml of toluene. An inorganic salt and the like were separated by filtration by subjecting the diluted solution to suction filtration. The filtrate was passed through a silica gel short column and concentrated. The concentrate was purified by silica gel chromatography (developing solvent: toluene:hexane=4:6). Then, the purified product was washed by being dispersed in a mixed solvent of ethyl acetate and hexane. Thus, a white solid (Compound (15)) was obtained (yield: 2.0 g, percent yield: 22%).

Synthesis Example 4

Synthesis of Compound (32)

(1) Synthesis of Compound (32-a)

[Chem. 74]

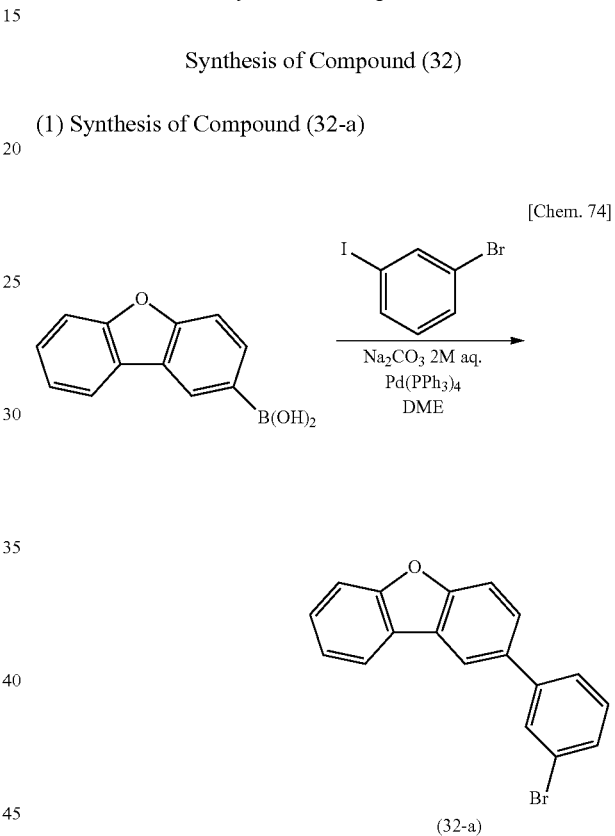

(32-a)

Under a nitrogen atmosphere, 21.2 g (100 mmol) of 2-dibenzofuranboronic acid, 31.1 g (110 mmol) of 1,3-bromoiodobenzene, 100 ml of a 2-M aqueous solution of sodium carbonate, and 100 ml of 1,2-dimethoxyethane were loaded into a three-necked flask, 1.16 g (1 mmol) of tetrakis(triphenylphosphine)palladium were added to the mixed solution, and then the whole was refluxed for 8 hours.

After the completion of the reaction, the reaction product was cooled to room temperature and then extracted with toluene by using a separating funnel. The extract was dried with anhydrous magnesium sulfate, and was then filtered and concentrated. The concentrate was purified by silica gel chromatography (developing solvent: hexane:toluene=8:2). The purified product was recrystallized from hexane. Thus, a white solid (Compound (32-a)) was obtained (yield: 25.6 g, percent yield: 79%).

(2) Synthesis of Compound (32)

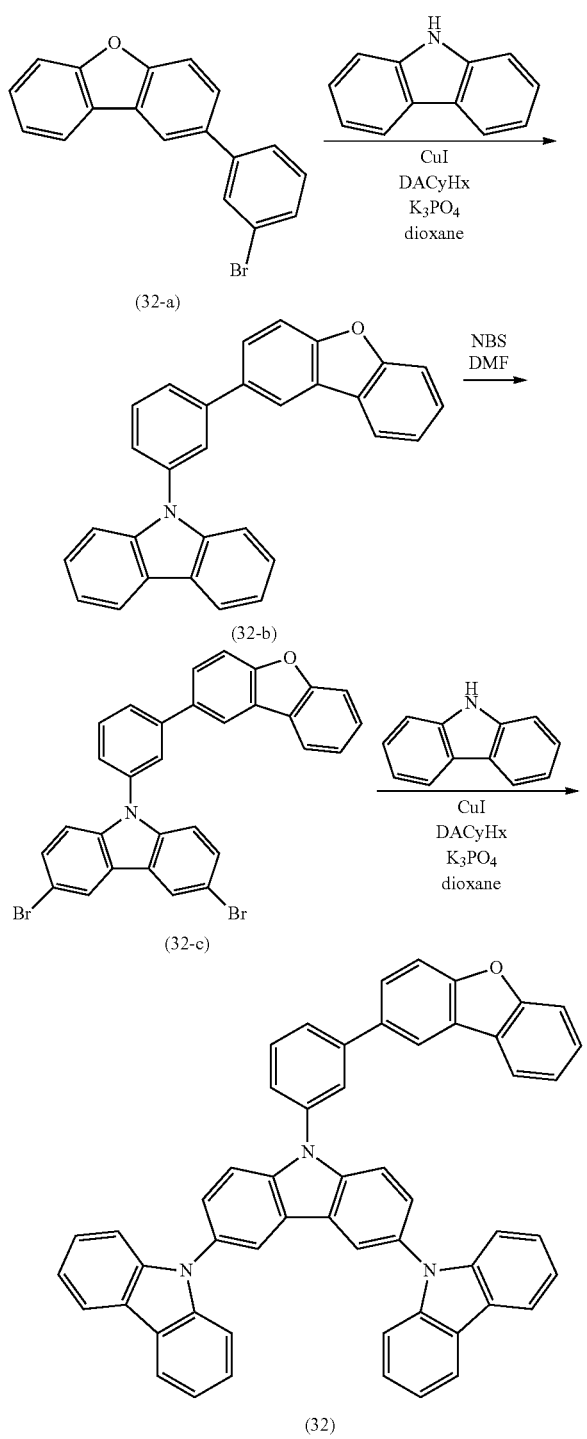

Compound (32) was synthesized in the same manner as in Compounds (1-a) to (1) except that 2-bromodibenzofuran as a raw material was changed to Compound (32-a).

Each of those compounds was identified by: subjecting the compound to FD/MS measurement; and judging whether the theoretical value for its molecular weight and the actual value coincided with each other.

Example 1

A glass substrate (manufactured by GEOMATEC Co., Ltd.) with an ITO transparent electrode measuring 25 mm wide by 75 mm long by 1.1 mm thick was subjected to ultrasonic cleaning in isopropyl alcohol for 5 minutes. After that, the substrate was subjected to UV/ozone cleaning for 30 minutes. The glass substrate with the transparent electrode line after the cleaning was mounted on the substrate holder of a vacuum deposition apparatus. First, Compound (HT) was deposited from the vapor onto the surface of the glass substrate on the side where the transparent electrode line was formed by resistance heating so as to cover the transparent electrode (to have a thickness of 60 mm). The film formation rate was set to 1 Å/s. The HT film functions as a hole injecting/transporting layer.

Next, Compound (1) (host compound) was deposited from the vapor onto the HT film by resistance heating to form a Compound (1) film having a thickness of 30 nm. At this time, the vapor deposition was performed so that amass ratio of Compound (BD) as a phosphorescent dopant with respect to Compound (1) was 10%. The film formation rates of Compound (1) and Compound (BD) were set to 1.0 Å/s and 0.11 Å/s, respectively. The thin film functions as a phosphorescent light emitting layer.

Next, Compound (HB) was deposited from the vapor onto the phosphorescent light emitting layer by resistance heating to form an HB film having a thickness of 10 nm. The film formation rate was 1 Å/s. The HB film functions as a hole blocking layer.

A tris(8-quinolinol)aluminum (Alq) complex was deposited from the vapor onto the film at a film formation rate of 1 Å/s (to have a thickness of 30 nm). The film functions as an electron injecting layer.

After that, LiF was deposited from the vapor onto the Alq film at a film formation rate of 0.1 Å/s (to have a thickness of 0.5 nm). Metal Al was deposited from the vapor onto the LiF film at a film formation rate of 1 Å/s to form a metal cathode (having a thickness of 100 nm). Thus, an organic EL device was obtained.

[Chem. 76]

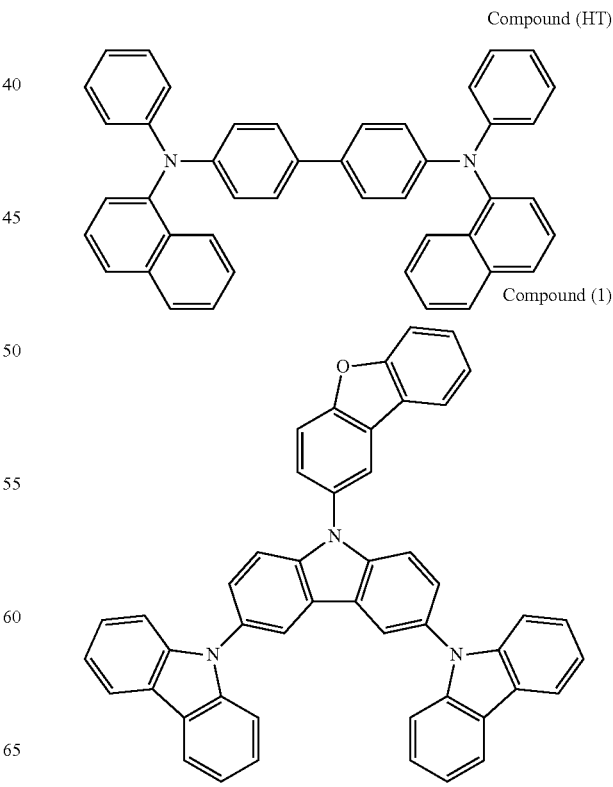

-continued
Compound BD)
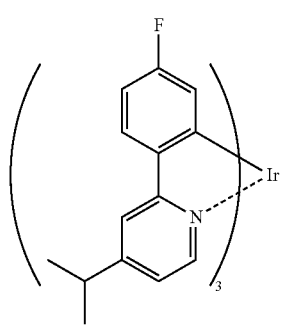
Compound (HB)
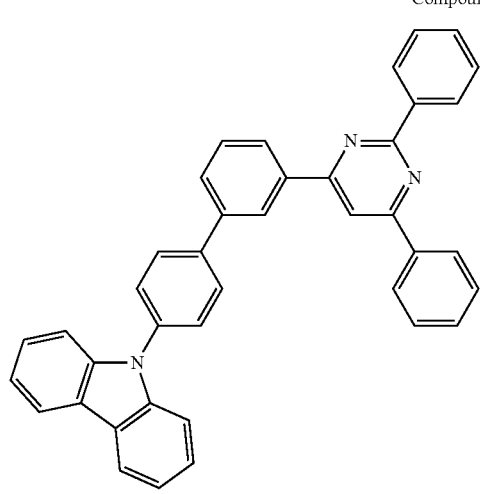
Alq
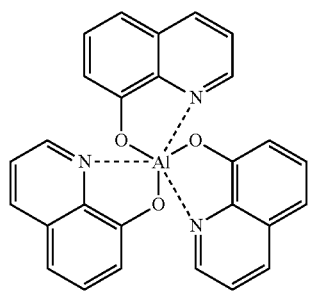
Examples 2 to 4
Organic EL devices were each produced in the same manner as in Example 1 except that a host material listed in Table 1 was used instead of Compound (1) in Example 1.
[Chem. 77]
Compound (32)
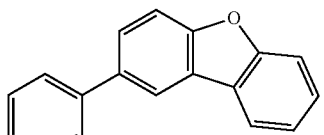
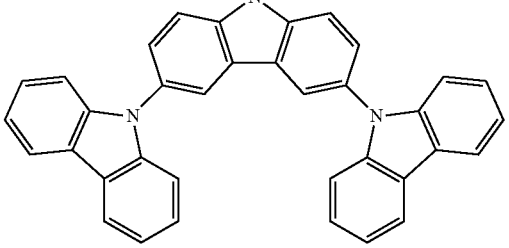
Compound (2)
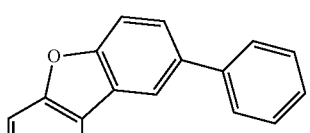
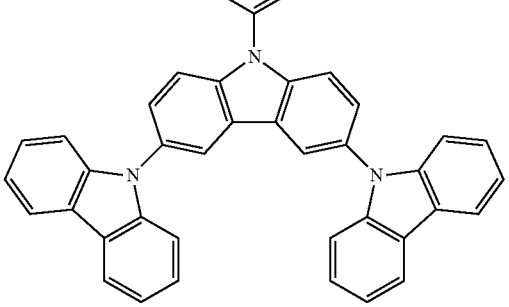
(Compound 15)
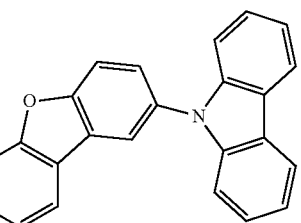
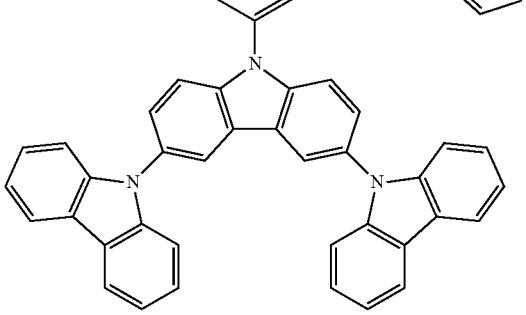

Comparative Examples 1 to 5
Organic EL devices were produced in the same manner as in Example 1 except that Compounds (H1) to (H6) shown below were used instead of Compound (1).
[Chem. 78]
Compound (H1)
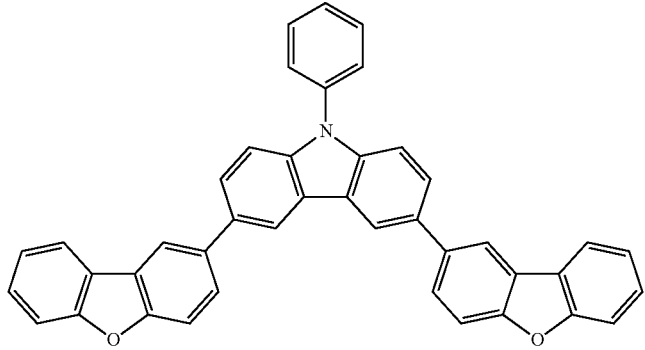
Compound (H2)
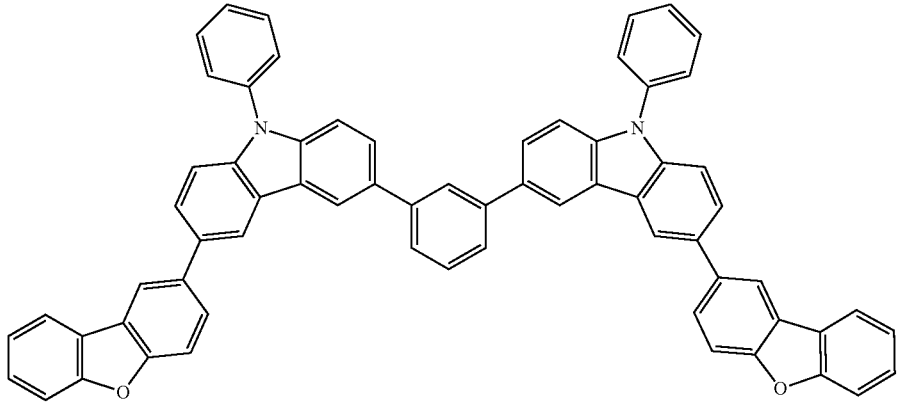
Compound (H4)
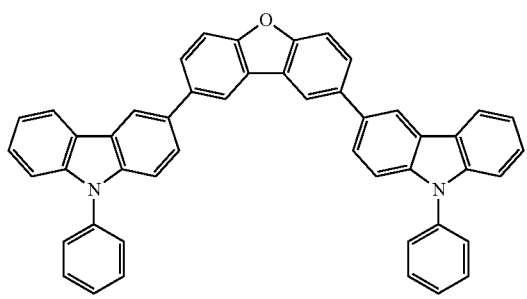
Compound (H5)
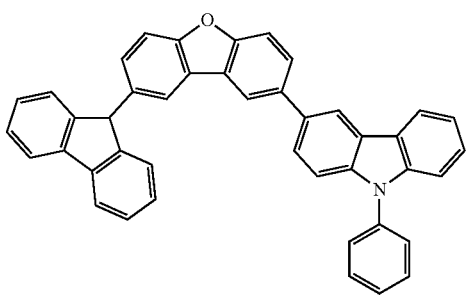
Compound (H-6)
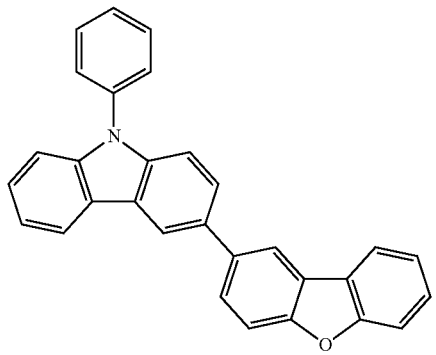

TABLE 1

| | Host | Voltage (V) | External quantum efficiency (%) | Half lifetime (hour(s)) |
|---|---|---|---|---|
| Example 1 | (1) | 8.5 | 9.2 | 1,270 |
| Example 2 | (32) | 8.9 | 8.4 | 1,330 |
| Example 3 | (2) | 8.7 | 8.2 | 1,000 |
| Example 4 | (15) | 8.4 | 8.1 | 1,160 |
| Comparative Example 1 | H1 | 8.8 | 7.0 | 700 |
| Comparative Example 2 | H2 | 8.8 | 7.1 | 650 |
| Comparative Example 3 | H4 | 9.3 | 6.4 | 450 |
| Comparative Example 4 | H5 | 9.5 | 6.9 | 480 |
| Comparative Example 5 | H6 | 9.3 | 6.9 | 250 |

It is understood from Table 1 that a device using any one of Compounds (1), (32), (2), and (15) of the present invention has higher efficiency and a longer lifetime than those of a device using any one of the compounds of the comparative examples. It is also understood that the device is an organic EL device whose power consumption has been reduced because the device can be driven at an additionally low voltage.

INDUSTRIAL APPLICABILITY

As described above in detail, the utilization of the material for an organic electroluminescence device of the present invention can provide an organic EL device which shows high luminous efficiency and has a long lifetime. Accordingly, the organic EL device of the present invention is extremely useful as, for example, a display and a light source for various electronic instruments.

The invention claimed is:

1. A material for an organic electroluminescence device of formula (1):

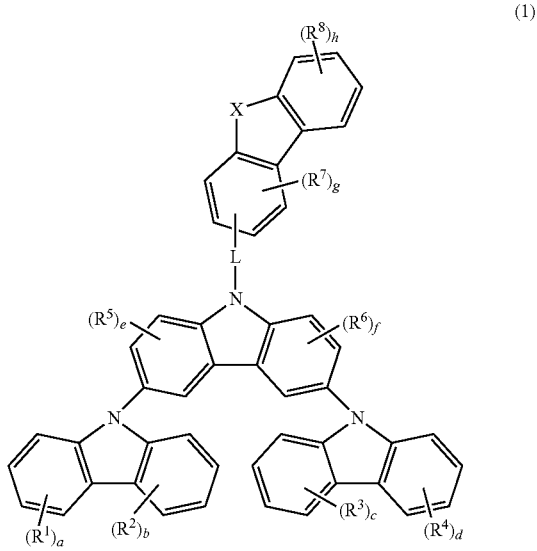

wherein X is an oxygen atom or a sulfur atom;
$R^1$ to $R^8$ are each independently an alkyl group having 1 to 20 carbon atoms, a cycloalkyl group having 3 to 20 ring carbon atoms, an alkoxy group having 1 to 20 carbon atoms, a cycloalkoxy group having 3 to 20 ring carbon atoms, an aryl group having 6 to 18 ring carbon atoms, an aryloxy group having 6 to 18 ring carbon atoms, a heteroaryl group having 5 to 18 ring atoms, an amino group, a silyl group, a fluoro group, or a cyano group, and each of $R^1$ to $R^8$ is independently optionally substituted;

each of a to d and h is independently an integer of from 0 to 4;

each of e to g is independently an integer of from 0 to 3;

a total of a to h is 6 or less; and

L is a single bond, an alkylene group having 1 to 20 carbon atoms, a cycloalkylene group having 3 to 20 ring carbon atoms, an arylene group having 6 to 18 ring carbon atoms, or a heteroarylene group having 5 to 18 ring atoms;

L is optionally substituted with an optionally substituted alkyl group having 1 to 20 carbon atoms, an optionally substituted cycloalkyl group having 3 to 20 ring carbon atoms, an optionally substituted alkoxy group having 1 to 20 carbon atoms, an optionally substituted cycloalkoxy group having 3 to 20 ring carbon atoms, an optionally substituted aryl group having 6 to 18 ring carbon atoms, an optionally substituted aryloxy group having 6 to 18 ring carbon atoms, an optionally substituted heteroaryl group having 5 to 18 ring atoms, an optionally substituted amino group, an optionally substituted silyl group, an optionally substituted fluoro group, or an optionally substituted cyano group, and the material is suitable for an organic electroluminescence device.

2. The material of claim 1, wherein the X is an oxygen atom.

3. An organic electroluminescence device, comprising:
one or more organic thin film layers,
wherein the one or more organic thin film layers comprise a light emitting layer between a cathode and an anode, and
a layer of the one or more organic thin film layers comprises the material for an organic electroluminescence device of claim 1.

4. The organic electroluminescence device of claim 3, wherein the light emitting layer comprises the material for an organic electroluminescence device as a host material.

5. The organic electroluminescence device of claim 3, wherein the light emitting layer comprises a host material and a phosphorescent material, and
the host material comprises the material for an organic electroluminescence device.

6. The organic electroluminescence device of claim 5, wherein the phosphorescent light emitting material comprises a compound comprising iridium (Ir), osmium (Os), or platinum (Pt).

7. The organic electroluminescence device of claim 6, wherein the compound comprises an orthometalated metal complex.

8. The organic electroluminescence device of claim 7, wherein the orthometalated metal complex is a complex of Ir or Pt.

9. The organic electroluminescence device of claim 3, further comprising a reductive dopant at an interfacial region between the cathode and the one or more organic thin film layers.

10. The organic electroluminescence device of claim 9, wherein the reductive dopant is an alkali metal, an alkali metal complex, an alkali metal compound, an alkaline earth metal, an alkaline earth metal complex, an alkaline earth metal compound, a rare earth metal, a rare earth metal complex, a rare earth metal compound, or any combination thereof.

11. The organic electroluminescence device of claim 3,
wherein a layer of the one or more organic thin film layers comprises an electron injecting layer between the light emitting layer and the cathode, and
the electron injecting layer comprises a nitrogen-comprising ring derivative as a main component.

12. The organic electroluminescence device claim 3,
wherein a layer of the one or more organic thin film layers comprises a hole transporting layer between the light emitting layer and the anode, and
the hole transporting layer comprises the material for an organic electroluminescence device.

13. The material of claim 1, wherein at least one of $R^1$ to $R^8$ is a phenyl group or a mesityl group.

14. The material of claim 1, wherein each of a to d and h is independently 0, 1, or 2.

15. The material of claim 1, wherein each of e to g is independently 0 or 1.

16. The material of claim 1,
wherein the material is of formula (2):

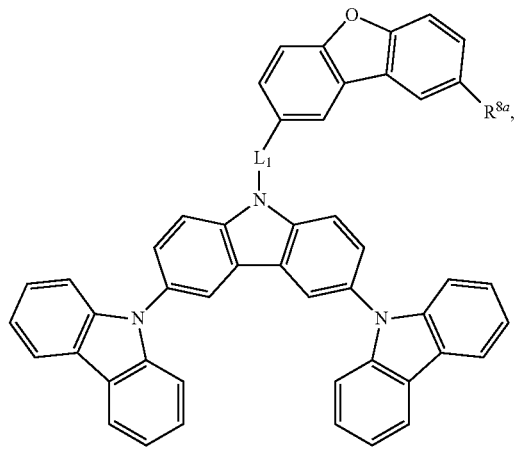

(2)

$L_1$ is a single bond or an arylene group having 6 to 18 ring carbon atoms, and
$R^{8a}$ is a hydrogen atom, an aryl group having 6 to 18 ring carbon atoms, or a heteroaryl group having 5 to 18 ring atoms.

17. The material of claim 16, wherein $L_1$ is a phenylene group.

18. The material of claim 16, wherein $R^{8a}$ is a phenyl group or a carbazolyl group.

19. The material of claim 1, wherein a triplet energy level of the material is 2.0 eV or more.

* * * * *